United States Patent [19]
Tsuchiya et al.

[11] Patent Number: 6,140,333
[45] Date of Patent: Oct. 31, 2000

[54] N-ACYL CYCLIC AMINE DERIVATIVES

[75] Inventors: Yoshimi Tsuchiya, Tsukuba; Takashi Nomoto, Menuma-machi; Hirokazu Ohsawa, Tsukuba; Kumiko Kawakami, Tsukuba; Kenji Ohwaki, Tsukuba; Masaru Nishikibe, Tsukuba, all of Japan

[73] Assignee: Banyu Pharmaceutical Co Ltd, Tokyo, Japan

[21] Appl. No.: 09/244,985

[22] Filed: Feb. 4, 1999

[30] Foreign Application Priority Data

Feb. 4, 1998 [JP] Japan ................................. 10-038063
Jul. 29, 1998 [JP] Japan ................................. 10-228726

[51] Int. Cl.$^7$ .................... A61K 31/505; A61K 31/445; C07D 409/00; C07D 219/00; C07D 211/30
[52] U.S. Cl. .......................... 514/258; 544/231; 544/279; 544/280; 544/238; 546/15; 546/16; 546/112; 546/113; 546/192; 546/225; 546/226; 514/278; 514/318; 514/320; 514/329; 514/330; 514/331
[58] Field of Search ................ 546/226, 15, 16, 546/112, 113, 192, 225; 544/230, 231, 279, 280; 514/258, 278, 318, 320, 329, 330, 331

[56] References Cited

U.S. PATENT DOCUMENTS 5,344,835  9/1994  Alker et al. ............................... 514/317

FOREIGN PATENT DOCUMENTS

| 2155320 | 8/1993 | Canada .................................. 546/225 |
| 0747355 | 12/1996 | European Pat. Off. ................ 546/225 |
| 5501560 | 3/1993 | Japan .................................... 546/225 |
| 7258250 | 10/1995 | Japan .................................... 546/225 |
| 8198751 | 8/1996 | Japan .................................... 546/225 |
| 8291141 | 11/1996 | Japan .................................... 546/225 |
| 9278749 | 10/1997 | Japan .................................... 546/225 |
| 9278751 | 10/1997 | Japan .................................... 546/225 |
| 9316048 | 8/1993 | WIPO ................................... 546/225 |
| 9521820 | 8/1995 | WIPO ................................... 546/225 |

OTHER PUBLICATIONS

Bertram G. Katzung, MD, PhD, "Basic and Clinical Pharmacology", 4th ed. Appleton & Lange, Chapter 8, pp. 83–92 (1989).

Henri N. Doods, "Selective Muscarinic Antagonists as Bronchodilators", Drug News & Perspective, 5(6), pp. 345–352.

*Primary Examiner*—Alan L. Rotman
*Assistant Examiner*—Raymond Covington

[57] ABSTRACT

The invention relates to compounds represented by the general formula [I]

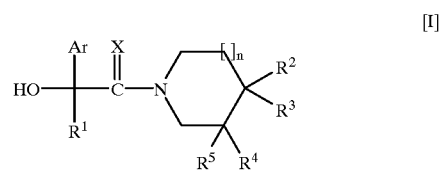

[wherein Ar means an aryl group or a heteroaryl group which may have a substitutive group selected from a group consisting of a halogen atom, a lower alkyl group and a lower alkoxy group; $R^1$ means a $C_3$–$C_6$ cycloalkyl group which is substitutable with a fluorine atom; $R^2$ and $R^4$ mean hydrogen atoms, groups represented by —$(A^1)_m$—NH—B or the like; $R^3$ and $R^5$ mean hydrogen atoms, $C_1$–$C_6$ aliphatic hydrocarbon groups or the like which are substitutable with a lower alkyl group(s); n means 0 or 1; and X means an oxygen atom or a sulfur atom].

Compounds according to the invention, since they not only have potent selective antagonistic activity against muscarinic $M_3$ receptors but also exhibit excellent oral activity, durability of action and pharmacokinetics, are very useful as safe and effective remedies against respiratory, urinary and digestive diseases with little adverse side effects.

27 Claims, No Drawings

N-ACYL CYCLIC AMINE DERIVATIVES

TECHNICAL FIELD

The present invention relates to novel N-acyl cyclic amine derivatives, processes for manufacturing them, pharmaceutics containing them and their use as medicines, especially in the treatment of various diseases of the respiratory, urinary and digestive systems.

BACKGROUND ART

Antagonism to muscarinic receptors is known to cause bronchodilation, gastrointestinal hypanakinesis, gastric hyposecretion, dry mouth, mydriasis, suppression of bladder contraction, hypohidrosis, tachycardia and the like ["Basic and Clinical Pharmacology", 4th ed., APPLETON & LANGE, pp. 83–92 (1989); *Drug News & Perspective*, 5(6), pp. 345–352 (1992)].

It has been made clear through recent studies that there are at least three subtypes of muscarinic receptors; the $M_1$ receptors being present mainly in the brain, the $M_2$ receptors mainly in the heart, and the $M_3$ receptors, on smooth muscles and glandular tissues. However, all of the large number of compounds heretofore known to exhibit antagonism to muscarinic receptors non-selectively antagonize the three subtypes of muscarinic receptors. Consequently, attempts to use these compounds as therapeutic or prophylactic agents for diseases of the respiratory system have caused undesirable side effects such as dry mouth, nausea and mydriasis. Still in addition, particularly serious side effects associated with the central nervous system, such as dementia, attributable to the $M_1$ receptors and those associated with the heart, such as tachycardia mediated by the $M_2$ receptors, pose problems, and their solution is strongly demanded.

Chemical compounds structurally similar to those of the present invention include, for instance, the compounds cited as Example 33 in the International Patent Publication WO 93/16048. The publication also discloses that the compounds exhibit anticholinergic activity. However, the compounds according to this invention are neither specifically disclosed nor suggested. Nor is there any mention at all of highly selective antagonism to muscarine $M_3$ receptors.

DISCLOSURE OF THE INVENTION

An object of the present invention is to provide a relatively side effect-free, safe and effective drug, exhibiting highly selective antagonism to muscarine $M_3$ receptors, for the treatment of diseases associated with muscarine $M_3$ receptors.

The inventors have discovered that compounds represented by the general formula [I]

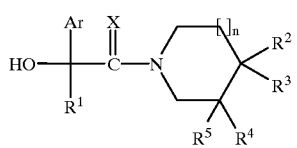

[wherein Ar means an aryl group or a heteroaryl group which may have a substitutive group selected from a group consisting of a halogen atom, a lower alkyl group and a lower alkoxy group; $R^1$ means a $C_3$–$C_6$ cycloalkyl group which is substitutable with a fluorine atom; $R^2$ means a hydrogen atom or a group represented by —$(A^1)_m$—NH—B; or, combined with $R^3$, means a group represented by =$A^2$—NH—B; or, together with the adjoining one of the carbon atoms on the ring, means a $C_2$–$C_8$ aliphatic nitrogen-containing heterocyclic group containing an imino group, which is substitutable with a lower alkyl group, or a $C_3$–$C_8$ aliphatic carbocyclic group having on the ring a group represented by —$(A^1)_m$—NH—B, which is substitutable with a lower alkyl group; or, combined with $R^4$, together with the adjoining two of the carbon atoms on the ring, means a $C_2$–$C_8$ aliphatic nitrogen-containing heterocyclic group containing an imino group, which is substitutable with a lower alkyl group; $R^3$ means a hydrogen atom or a $C_1$–$C_6$ aliphatic hydrocarbon group which is substitutable with a lower alkyl group; or, combined with $R^5$, means a single bond; or, combined with $R^2$, means the same as the foregoing; $R^4$ means a hydrogen atom or a group represented by —$(A^1)_m$—NH—B; or, combined with $R^5$, means a group represented by =$A^2$—NH—B; or, together with the adjoining one of the carbon atoms on the ring, means a $C_2$–$C_8$ aliphatic nitrogen-containing heterocyclic group containing an imino group, which is substitutable with a lower alkyl group, or a $C_3$–$C_8$ aliphatic carbocyclic group having on the ring a group represented by —$(A^1)_m$—NH—B, which is substitutable with a lower alkyl group; or, combined with $R^2$, means the same as the foregoing; $R^5$ means a hydrogen atom or a $C_1$–$C_6$ aliphatic hydrocarbon group which is substitutable with a lower alkyl group; or, combined with $R^3$ or $R^4$, means respectively the same as the foregoing; $A^1$ means a $C_1$–$C_8$ bivalent aliphatic hydrocarbon group which is substitutable with a lower alkyl group; $A^2$ means a $C_1$–$C_8$ trivalent aliphatic hydrocarbon group which is substitutable with a lower alkyl group; B means a hydrogen atom or a $C_1$–$C_6$ aliphatic hydrocarbon group which may have a substitutive group selected from a group consisting of a lower alkyl group and an aryl group; m and n mean identically or differently 0 or 1; and X means an oxygen atom or a sulfur atom (provided that (a) $R^2$ and $R^4$ do not mean a hydrogen atom at the same time, (b) when either $R^2$ or $R^4$ is a group represented by —$(A^1)_m$—NH—B, the other means a hydrogen atom, (c) when $R^2$ and $R^3$ combined means the same as the foregoing, $R^4$ means a hydrogen atom, and (d) when $R^4$ and $R^5$ combined means the same as the foregoing, $R^2$ means a hydrogen atom)] are relatively free from adverse side effects, safe and very useful as remedies for various diseases associated with muscarine $M_3$ receptors, including such respiratory diseases as chronic obstructive pulmonary diseases, chronic bronchitis, asthma, chronic respiratory obstruction, pulmonary fibrosis, pulmonary emphysema and rhinitis; such digestive diseases as irritable bowel syndrome, convulsive colitis, gastric and duodenal ulcers, convulsion or hyperkinesia of digestive canal, diverticulitis and pain accompanying contraction of smooth muscles of the digestive system; urinary diseases entailing dysuria such as urinary incontinence, urinary urgency and pollakiuria in nervous pollakiuria, neurogenic bladder, nocturnal enuresis, unstable bladder, cystospasm or chronic cystisis; and motion sickness, since they exhibit highly selective antagonism to muscarine $M_3$ receptors, high activity when orally administered, sustainable effects and excellent pharmacokinetics, and completed the present invention.

The invention relates to compounds represented by the general formula [I], their salts, processes for manufacturing them, and their use as medicines.

The invention further relates to intermediate products in the manufacture of the compounds represented by the general formula [I], i.e. compounds represented by the general formula [IV-a]

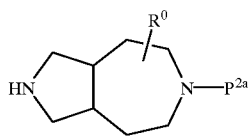

[IV-a]

[wherein $P^{2a}$ means a protective group for an imino group, and $R^0$ means a hydrogen atom or a lower alkyl group].

Hereinafter the meanings of the technical terms used in the present specification are stated, and the invention is explained in further detail.

The "halogen atom" means a fluorine atom, a chlorine atom, a bromine atom or an iodine atom.

The "lower alkyl group" means a straight chain or branched $C_1$–$C_6$ alkyl group, examples of which include methyl, ethyl, propyl, isopropyl, butyl, isobutyl, sec-butyl, t-butyl, pentyl, isopentyl, hexyl and isohexyl groups.

The "lower alkoxy" group means a straight chain or branched $C_1$–$C_6$ alkoxy group, examples of which include methoxy, ethoxy, propoxy, isopropoxy, butoxy, sec-butoxy, isobutoxy, t-butoxy, pentyloxy, isopentyloxy, hexyloxy and isohexyloxy groups.

The "aryl group" means a $C_6$–$C_{11}$ aryl group, examples of which phenyl and naphthyl groups.

The "heteroaryl group" means a 5-membered or 6-membered monocyclic heteroaryl group containing 1 or 2 hetero atoms selected, to be the same as or different from each other, out of a group consisting of nitrogen, oxygen and sulfur atoms, or a condensed ring type heteroaryl group resulting from the condensation of this monocyclic heteroaryl group and said aryl group or from the mutual condensation of the same or different such monocyclic heteroaryl groups, examples of which include 2-pyridyl, 3-pyridyl, 4-pyridyl, 2-thiazolyl, 4-thiazolyl, 2-thienyl, 3-thienyl, 1-imidazolyl, 2-imidazolyl, 4-imidazolyl, 3-pyrazolyl, 4-pyrazolyl, 2-furyl, 3-furyl, 2-pyrrolyl, 3-pyrrolyl, 2-pyrimidinyl, 4-pyrimidinyl, 5-pyrimidinyl, 2-pyrazinyl, 3-pyridazinyl, 4-pyridazinyl, 2-quinolinyl, 2-benzothienyl and 2-indolyl groups.

Examples of "$C_3$–$C_6$ cycloalkyl group" include cyclopropyl, cyclobutyl, cyclopentyl and cyclohexyl groups.

The "$C_2$–$C_8$ aliphatic nitrogen-containing heterocyclic group containing an imino group" in the phrase "together with the adjoining one of the carbon atoms on the ring, means a $C_2$–$C_8$ aliphatic nitrogen-containing heterocyclic group containing an imino group, which is substitutable with a lower alkyl group" means a group consisting of a saturated or unsaturated $C_2$–$C_8$ aliphatic nitrogen-containing heterocyclic ring containing an imino group, and this group combined with a cyclic group sharing a carbon atom on the ring constitutes a spiro cyclic group. Examples of this group include groups composed of aziridine, azetidine, pyrrolidine, piperidine, perhydroazepine, perhydroazocine, perhydroazonine, 3-pyrroline, 1,2,5,6-tetrahydropiridine, 1,5,6,7-tetrahydro-2H-azepine, and 1,2,5,6,7,8-hexahydroazocine rings, and preferable ones include a group composed of a pyrrolidine ring.

Therefore, the above "$C_2$–$C_8$ aliphatic nitrogen-containing heterocyclic group containing an imino group, which is substitutable with a lower alkyl group" means said aliphatic nitrogen-containing heterocyclic group in which any 1, 2 or more, the same as or different from each other, or more preferably 1 or 2, of the substitutable positions may have been substituted with said lower alkyl group, and preferable examples include methyl, ethyl, propyl and isopropyl groups.

The "$C_3$–$C_8$ aliphatic carbocyclic group having on the ring a group represented by —$(A^1)_m$—NH—B" in the phrase "together with the adjoining one of the carbon atoms on the ring, means a $C_3$–$C_8$ aliphatic carbocyclic group having on the ring a group represented by —$(A^1)_m$—NH—B, which is substitutable with a lower alkyl group" means a group consisting of a saturated or unsaturated $C_3$–$C_8$ aliphatic carbocyclic ring having on the ring a group represented by —$(A^1)_m$—NH—B, and this group combined with a cyclic group sharing a carbon atom on the ring constitutes a spiro cyclic group. Examples of this group include groups having on the ring a group represented by —$(A^1)_m$—NH—B, for instance groups composed of cyclopropane, cyclobutane, cyclopentane, cyclohexane, cycloheptane, cyclooctane, cyclopropene, cycrobutene, cyclopentene, cyclohexene, cycloheptene, cyclooctene and 1,3-cyclohexadiene rings.

Therefore, the above "$C_3$–$C_8$ aliphatic carbocyclic group having on the ring a group represented by —$(A^1)_m$—NH—B, which is substitutable with a lower alkyl group" means said aliphatic carbocyclic group in which any 1, 2 or more, the same as or different from each other, or more preferably 1 or 2, of the substitutable positions may have been substituted with said lower alkyl group, and preferable examples include methyl, ethyl, propyl and isopropyl groups.

The "$C_2$–$C_8$ aliphatic nitrogen-containing heterocyclic group containing an imino group" in the phrase "together with the adjoining two of the carbon atoms on the ring, means a $C_2$–$C_8$ aliphatic nitrogen-containing heterocyclic group containing an imino group, which is substitutable with a lower alkyl group" means a group consisting of a saturated or unsaturated $C_2$–$C_8$ aliphatic nitrogen-containing heterocyclic ring containing an imino group, and this group combined with a cyclic group sharing carbon atoms on the ring constitutes a bicyclic group. Examples of this group include groups composed of aziridine, azetidine, pyrrolidine, piperidine, perhydroazepine, perhydroazocine, perhydroazonine, 1,2,5,6-tetrahydropiridine, 1,5,6,7-tetrahydro-2H-azepine, and 1,2,5,6,7,8-hexahydroazocine rings, and preferable ones include a group composed of a perhydroazepine ring.

Therefore, the above "$C_2$–$C_8$ aliphatic nitrogen-containing heterocyclic group containing an imino group, which is substitutable with a lower alkyl group" means said aliphatic nitrogen-containing heterocyclic group in which any 1, 2 or more, the same as or different from each other, or more preferably 1 or 2, of the substitutable positions may have been substituted with said lower alkyl group, and preferable examples include methyl, ethyl, propyl and isopropyl groups.

The "$C_1$–$C_6$ aliphatic hydrocarbon group" means a straight chain saturated or unsaturated $C_1$–$C_6$ aliphatic hydrocarbon group.

Examples of saturated aliphatic hydrocarbon group include methyl, ethyl, propyl, butyl, pentyl and hexyl groups.

The unsaturated aliphatic hydrocarbon group means an aliphatic hydrocarbon group having 1, 2 or more, or more preferably 1 or 2, double bonds or triple bonds in any position(s) on the carbon chain, and examples include 2-propenyl, 2-butenyl, 3-butenyl, 2-pentenyl, 3-pentenyl, 4-pentenyl, ethynyl, 2-propynyl and 2-pentene-4-ynyl groups.

The "$C_1$–$C_8$ bivalent aliphatic hydrocarbon group" means a straight chain saturated or unsaturated $C_1$–$C_8$ bivalent aliphatic hydrocarbon group.

Examples of saturated bivalent hydrocarbon group include methylene, ethylene, trimethylene, tetramethlene, pentamethylene, hexamethylene, heptamethylene and octamethylene groups.

The unsaturated bivalent aliphatic hydrocarbon group means a bivalent aliphatic hydrocarbon group having 1, 2 or more, or more preferably 1 or 2, double bonds or triple bonds in any position(s) on the carbon chain, and examples include propenylene, 1-butenylene, 2-butenylene, 1-pentenylene, 2-pentenylene, 1,3-pentadienylene, 1,4-pentadienylene, 1-hexenylene, 2-hexenylene, 3-hexenylene, 1,3-hexadienylene, 1,4-hexadienylene, 1-heptenylene, 2-heptenylene, 3-heptenylene, 1,3-heptadienylene, 1,4-heptadienylene, 1,5-heptadienylene, 1,6-heptadienylene, 1,3,5-heptatrienylene, 1-octenylene, 2-octenylene, 3-octenylene, 4-octenylene, 1,3-octadienylene, 1,4-octadienylene, 1,5-octadienylene, 1,6-octadienylene, 1,7-octadienylene, 2,4-octadienylene, 2,5-octadienylene, 2,6-octadienylene, 3,5-octadienylene, 1,3,5-octatrienylene, 2,4,6-octatrienylene, 1,3,5,7-octatetraenylene, ethynylene, propynylene, 1-buthynylene and 2-buthynylene groups.

The "$C_1$–$C_8$ trivalent aliphatic hydrocarbon group" means a straight chain saturated or unsaturated $C_1$–$C_8$ trivalent aliphatic hydrocarbon group.

Examples of saturated aliphatic hydrocarbon group include methyne, 1-ethanyl-2-ylidene, 1-propanyl-3-ylidene, 1-butanyl-4-ylidene, 1-pentanyl-5-ylidene, 1-hexanyl-6-ylidene, 1-heptanyl-7-ylidene and 1-octanyl-8-ylidene groups.

The unsaturated trivalent aliphatic hydrocarbon group means a trivalent aliphatic hydrocarbon group having 1, 2 or more, or more preferably 1 or 2, double bonds or triple bonds in any position(s) on the carbon chain, and examples include 2-butene-1-yl-4-ylidene, 2-pentene-1-yl-5-ylidene, 2-hexene-1-yl-6-ylidene, 3-hexene-1-yl-6-ylidene, 2,4-hexadiene-1-yl-6-ylidene, 2-heptene-1-yl-7-ylidene, 3-heptene-1-yl-7-ylidene, 2,4-heptadiene-1-yl-7-ylidene, 2,5-heptadiene-1-yl-7-ylidene, 3,5-heptadiene-1-yl-7-ylidene, 2-octene-1-yl-8-ylidene, 3-octene-1-yl-8-ylidene, 4-octene-1-yl-8-ylidene, 2,4-octadien-1-yl-8-ylidene, 2,5-octadien-1-yl-8-ylidene, 2,6-octadien-1-yl-8-ylidene, 3,5-octadien-1-yl-8-ylidene, 2,4,6-octatrien-1-yl-8-ylidene, 1-pro-pynyl-3-ylidene, 1-butynyl-4-ylidene and 2-butin-1-yl-4-ylidene groups.

The salts of compounds represented by the general formula [I] mean salts which are acceptable as medicines in customary use, of which examples include inorganic acid salts such as hydrochlorides, sulfates, nitrates, phosphates and perchlorates; organic carboxylic acid salts such as benzoates, maleates, fumarates, succinates, tartrates, citrates and ascorbates; and organic sulfonic acid salts such as methanesulfonates, ethanesulfonates, isethionates, benzenesulfonates and p-toluenesulfonates.

Examples of "protective group for an amino or imino group" include aralkyl groups, such as benzyl, p-methoxybenzyl, p-nitrobenzyl, benzhydryl and trityl groups; lower alkanoyl groups, such as formyl, acetyl and propionyl groups; arylalkanoyl groups, such as phenylacetyl and phenoxyacetyl groups; lower alkoxycarbonyl groups, such as methoxycarbonyl, ethoxycarbonyl, isobutoxycarbonyl and t-butoxycarbonyl groups; alkenyloxycarbonyl groups, such as a 2-propenyloxycarbonyl group; aralkyloxycarbonyl groups, such as benzyloxycarbonyl, p-methoxybenzyloxycarbonyl and p-nitrobenzyloxycarbonyl groups; and lower alkylsilyl groups, such as trimethylsilyl and t-butyldimethylsilyl groups. Preferable ones include benzyl, t-butoxycarbonyl and benzyloxycarbonyl groups.

Examples of "hydroxyl group-protective group" include acyl groups, such as an acetyl group; alkylsilyl groups, such as trimethylsilyl and t-butyidimethylsilyl groups; aralkyl groups, such as benzyl and trityl groups; ether groups, such as a methoxymethyl group; and alkylidene ketal groups, such as an isopropylidene ketal group.

Example of "oxo group-protective group" include acetals and ketals, such as ethylene ketal and trimethylene ketal.

Examples of "leaving group" include halogen atoms, such as chlorine, bromine and iodine atoms; lower alkylsulfonyloxy groups, such as a methanesulfonyoxy group, and arylsulfonyloxy groups, such as a p-toluene-sulfonyloxy group.

The "lower alkoxycarbonyl group" means a straight or branched $C_2$–$C_7$ alkoxycarbonyl group, examples of which include methoxycarbonyl, ethoxycarbonyl, propoxycarbonyl, isopropoxycarbonyl, butoxycarbonyl, sec-butoxycarbonyl, isobutoxycarbonyl, t-butoxycarbonyl, pentyloxycarbonyl, isopentyloxycarbonyl, hexyloxycarbonyl, isohexyloxycarbonyl groups.

The "aralkyloxycarbonyl group" means a $C_7$–$C_{10}$ aralkyloxycarbonyl group, examples of which include benzyloxycarbonyl and phenethyloxycarbonyl groups.

The "remedies" mean pharmaceuticals administered for the purpose of treatment and/or prophylaxis of diseases.

Whereas stereoisomers such as optical isomers, diastereomers and geometrical isomers to any compound according to the present invention may exist, depending upon the form of its substituents, compounds according to the invention include all these stereoisomers and mixtures thereof.

To disclose compounds represented by the foregoing general formula [I] more specifically, various signs used in the formula [I] are explained in further detail below, with preferred specific examples cited for each.

Ar means an aryl group or a heteroaryl group which may have a substitutive group selected from a group consisting of a halogen atom, a lower alkyl group and a lower alkoxy group.

"An aryl group or a heteroaryl group which may have a substitutive group selected from a group consisting of a halogen atom, a lower alkyl group and a lower alkoxy group" means said aryl group or said heteroaryl group having undergone no substitution or said aryl group or said heteroaryl group having a substitutive group(s) in a position where substitution is possible, and 1, 2 or more, or preferably 1 or 2, which may be either the same as or different from each other, can be selected from a group consisting of a halogen atom, a lower alkyl group and a lower alkoxy group as said substitutive group(s).

Preferable examples of halogen atom for the substitutive group include fluorine, chlorine and bromine atoms.

Preferable examples of lower alkyl group for the substitutive group include methyl, ethyl, propyl and isopropyl groups.

Preferable examples of lower alkoxy group for the substitutive group include methoxy, ethoxy, propoxy and isopropoxy groups.

A halogen atom or the like is preferable as the substitutive group.

An unsubstituted phenyl group is preferable as Ar.

$R^1$ means a $C_3$–$C_6$ cycloalkyl group which is substitutable with a fluorine atom.

The "$C_3$–$C_6$ cycloalkyl group which is substitutable with a fluorine atom" means said $C_3$–$C_6$ cycloalkyl group having undergone no substitution or said $C_3$–$C_6$ cycloalkyl group having a fluorine atom(s) in any substitutable position, wherein 1, 2 or more, or preferably 1 or 2, of the fluorine atom(s) is substitutable on the cycloalkyl group.

Preferable examples of cycloalkyl group include a cycloalkyl group, more preferably a cyclopentyl group, having undergone substitution with a fluorine atom(s), of which a cyclopentyl group having undergone substitution with 2 fluorine atoms is particularly preferable.

Therefore, preferable examples of $R^1$ include cyclopropyl, cyclobutyl, cyclopentyl, cyclohexyl, 1-fluorocyclopropyl, 1-fluorocyclobutyl, 1-fluorocyclopentyl, 1-fluorocyclohexyl, 2-fluorocyclopropyl, 2-fluorocyclobutyl, 2-fluorocyclopentyl, 2-fluorocyclohexyl, 3-fluorocyclobutyl, 3-fluorocyclopentyl, 3-fluorocyclohexyl, 4-fluorocyclohexyl, 2,2-difluorocyclopropyl, 2,2-difluorocyclobutyl, 2,2-difluorocyclopentyl, 2,2-difluorocyclohexyl, 3,3-difluorocyclobutyl, 3,3-difluorocyclopentyl, 3,3-difluorocyclohexyl, 4,4-difluorocyclohexyl, 3,3,4,4-tetrafluorocyclopentyl, 3,3,4,4-tetrafluorocyclohexyl, 2,3-difluorocyclobutyl, 2,3-difluorocyclopentyl, 3,4-difluorocyclopentyl, 2,3-difluorocyclohexyl, 3,4-difluorocyclohexyl, 2,2,3,3-tetrafluorocyclobutyl and 2,2,3,3-tetrafluorocyclopentyl groups, of which more preferable ones include 2-fluorocyclobutyl, 2-fluorocyclopentyl, 2-fluorocyclohexyl, 3-fluorocyclobutyl, 3-fluorocyclopentyl, 3-fluorocyclohexyl, 4-fluorocyclohexyl, 2,2-difluorocyclobutyl, 2,2-difluorocyclopentyl, 2,2-difluorocyclohexyl, 3,3-difluorocyclobutyl, 3,3-difluorocyclopentyl, 3,3-difluorocyclohexyl, 4,4-difluorocyclohexyl, 3,3,4,4-tetrafluorocyclopentyl and 2,2,3,3-tetrafluorocyclopentyl groups, above all a 3,3-difluorocyclopentyl group.

$R^2$ means a hydrogen atom or a group represented by $-(A^1)_m-NH-B$; or, combined with $R^3$, means a group represented by $=A^2-NH-B$; or, together with the adjoining one of the carbon atoms on the ring, means a $C_2-C_8$ aliphatic nitrogen-containing heterocyclic group containing an imino group, which is substitutable with a lower alkyl group, or a $C_3-C_8$ aliphatic carbocyclic group having on the ring a group represented by $-(A^1)_m-NH-B$, which is substitutable with a lower alkyl group; or, combined with $R^4$, together with the adjoining two of the carbon atoms on the ring, means a $C_2-C_8$ aliphatic nitrogen-containing heterocyclic group containing an imino group, which is substitutable with a lower alkyl group.

$A^1$ means a $C_1-C_8$ bivalent aliphatic hydrocarbon group which is substitutable with a lower alkyl group.

The "$C_1-C_8$ bivalent aliphatic hydrocarbon group which is substitutable with a lower alkyl group" means said $C_1-C_8$ bivalent aliphatic hydrocarbon group having undergone no substitution or said $C_1-C_8$ bivalent aliphatic hydrocarbon group having a lower alkyl group(s) in any substitutable position, wherein 1, 2 or more, or preferably 1 or 2, which may be either the same as or different from each other, of the lower alkyl group(s) is substitutable on the aliphatic hydrocarbon group.

Preferable examples of lower alkyl group as the substitutive group include methyl, ethyl, propyl and isopropyl groups.

Preferable examples of $A^1$ in $R^2$ include a $C_2$ saturated bivalent aliphatic hydrocarbon group.

Therefore, preferable examples of $A^1$ in $R^2$ include methylene, ethylene, trimethylene, tetramethylene, propenylene, ethylidene, propylidene, isopropylidene, 1-methylethylene, 1-ethylethylene, 1-propylethylene, 1,1-dimethylethylene, 1,2-dimethylethylene, 1-methyltrimethylene, 2-methyltrimethylene, 1-ethyltrimethylene, 2-ethyltrimethylene, 1,1-dimethyltrimethylene, 2,2-dimethyltrimethylene, 1-methyltetramethylene, 2-methyltetramethylene, 1-ethyltetramethylene, 2-ethyltetramethylene, 1,1-dimethyltetramethylene and 2,2-dimethyltetramethylene groups, of which ethylene, 1-methylethylene and 1-ethylethylene groups are particularly preferable.

B means a hydrogen atom or a $C_1-C_6$ aliphatic hydrocarbon group which may have a substitutive group selected from a group consisting of a lower alkyl group and an aryl group.

The "$C_1-C_6$ aliphatic hydrocarbon group which may have a substitutive group selected from a group consisting of a lower alkyl group and an aryl group" means said $C_1-C_6$ aliphatic hydrocarbon group having undergone no substitution or said $C_1-C_6$ aliphatic hydrocarbon group having a substitutive group(s) in any substitutable position, wherein the substitutive group(s) can be selected from a group consisting of a lower alkyl group and an aryl group, 1, 2 or more, or preferably 1 or 2, which may be either the same as or different from each other, of the substitutive group(s) may be selected.

Preferable examples of lower alkyl group as the substitutive group include methyl, ethyl, propyl and isopropyl groups.

Preferable examples of aryl group include a phenyl group.

Therefore, examples of B of a group represented by $-(A^1)_m-NH-B$ in $R^2$ include a hydrogen atom and methyl, ethyl, propyl, isopropyl, 2-propenyl, 2-butenyl, 2-propynyl, 1-methyl-2-propenyl, 2-methyl-2-propenyl, benzyl and 2-phenylethyl groups, of which more preferable ones include a hydrogen atom and methyl, ethyl, 2-propenyl and benzyl groups, above all a hydrogen atom.

Sign m stands for either 0 or 1, and 1 is preferable for m in $R^2$.

Therefore, examples of the group represented by $-(A^1)_m-NH-B$ in $R^2$ include amino, aminomethyl, 1-aminoethyl, 2-aminoethyl, 1-aminomethylethyl, 1-aminomethylpropyl, 2-aminopropyl, 2-aminobutyl, 2-aminopentyl and 2-amino-2-methylpropyl groups, of which more preferable ones include 2-aminoehtyl and 1-aminomethylethyl groups.

$A^2$ means a $C_1-C_8$ trivalent aliphatic hydrocarbon group which is substitutable with a lower alkyl group.

The "$C_1-C_8$ trivalent aliphatic hydrocarbon group which is substitutable with a lower alkyl group" means said $C_1-C_8$ trivalent aliphatic hydrocarbon group having undergone no substitution or said $C_1-C_8$ trivalent aliphatic hydrocarbon group having a lower alkyl group(s) in any substitutable position, wherein 1, 2 or more, or preferably 1 or 2, which may be either the same as or different from each other, of the lower alkyl group(s) can be substituted.

Preferable examples of lower alkyl group as the substitutive group include methyl, ethyl, propyl and isopropyl groups.

Preferable examples of A in a group represented by $=A^2-NH-B$ meant by $R^2$ and $R^3$ combined include a saturated $C_2$ trivalent aliphatic hydrocarbon.

Therefore, preferable examples of $A^2$ in a group represented by $=A^2-NH-B$ meant by $R^2$ and $R^3$ combined include 1-ethanyl-2-ylidene, 1-propanyl-3-ylidene, 1-butanyl-4-ylidene, 2-buten-1-yl-4-ylidene, 1-methyl-1-ethanyl-2-ylidene, 2-methyl-1-ethanyl-2-ylidene, 1,1-dimethyl-1-ethanyl-2-ylidene, 1-ethyl-1-ethanyl-2-ylidene, 1-methyl-l-propanyl-3-ylidene, 2-methyl-1-pro-panyl-3-ylidene, 3-methyl-1-propanyl-3-ylidene, 1,1-dimethyl-l-propanyl-3-ylidene and 1-ethyl-1-propanyl-3-ylidene groups, of which a 1-ethanyl-2-ylidene group is more preferable.

Examples of B in a group represented by =A²—NH—B meant by R² and R³ combined include similar groups cited earlier with respect to B in a group represented by —(A¹)$_m$—NH—B in R², and the same is true with more preferable examples.

Therefore, examples of the group represented by =A²—NH—B meant by R² and R³ combined include 2-aminoethylidene, 2-aminopropylidene, 3-aminopropylidene, 4-aminobutylidene and 4-amino-2-butenylidene groups, of which a 2-aminoethylidene group is more preferable.

The "$C_2$–$C_8$ aliphatic nitrogen-containing heterocyclic group containing an imino group, which is substitutable with a lower alkyl group" meant by R² and R³ combined, together with the adjoining one cyclic carbon atom, constitutes, together with a cyclic group sharing a carbon atom on the ring, a spiro cyclic group which is substitutable with a lower alkyl group(s) in any substitutable position. Examples of the spiro cyclic group include, where n=0, 1,5-diazaspiro[2.4]hept-5-yl, 1,6-diazaspiro[3.4]oct-6-yl, 2,6-diazaspiro[3.4]oct-6-yl, 1,7-diazaspiro[4.4]non-7-yl, 2,7-diazaspiro[4.4]non-2-yl, 2,6-diazaspiro[4.5]dec-2-yl, 2,7-diazaspiro[4.5]dec-2-yl, 2,8-diazaspiro[4.5]dec-2-yl, 2,6-diazaspiro[4.6]undec-2-yl, 2,7-diazaspiro[4.6]undec-2-yl, 2, 8-diazaspiro[4.6]undec-2-yl, 2,6-diazaspiro[4.7]dodec-2-yl, 2,7-diazaspiro[4.7]dodec-2-yl, 2,8-diazaspiro[4.7]dodec-2-yl, 2, 9-diazaspiro[4.7]dodec-2-yl, 1,7-diazaspiro[4.4]non-3-en-7-yl, 2,6-diazaspiro[4.5]dec-8-en-2-yl, 2,6-diazaspiro[4.5]dec-9-en-2-yl and 2,7-diazaspiro[4.5]dec-9-en-2-yl groups, of which 2,7-diazaspiro[4.4]non-2-yl and 2,8-diazaspiro[4.5]dec-2-yl groups are more preferable; where n=1, examples include 1,6-diazaspiro[2.5]oct-6-yl, 1,7-diazaspiro[3.5]non-7-yl, 2,7-diazaspiro[3.5]non-7-yl, 1,8-diazaspiro[4.5]dec-8-yl, 2,8-diazaspiro[4.5]dec-8-yl, 1,9-diazaspiro[5.5]undec-9-yl, 2,9-diazaspiro[5.5]undec-9-yl, 3,9-diazaspiro[5.5]undec-3-yl, 3,7-diazaspiro[5.6]dodec-3-yl, 3,8-diazaspiro[5.6]dodec-3-yl, 3,9-diazaspiro[5.6]dodec-3-yl, 3,7-diazaspiro[5.7]tridec-3-yl, 3,8-diazaspiro[5.7]tridec-3-yl, 3, 9-diazaspiro-[5.7]tridec-3-yl, 3,10-diazaspiro[5.7]tridec-3-yl, 1,8-diazaspiro[4.5]dec-3-en-8-yl, 1, 9-diazaspiro[5.5]undec-3-en-9-yl, 1,9-diazaspiro[5.5]undec-4-en-9-yl and 2,9-diazaspiro[5.5]undec-4-en-9-yl groups, of which more preferable ones include 2,8-diazaspiro[4.5]dec-8-yl and 3,9-diazaspiro[5.5]undec-3-yl groups.

The "$C_3$–$C_8$ aliphatic carbocyclic group having on the ring a group represented by —(A¹)$_m$—NH—B, which is substitutable with a lower alkyl group" meant by R² and R³ combined, together with the adjoining one of the carbon atoms on the ring, constitutes, together with a cyclic group sharing a carbon atom on the ring, a spiro cyclic group which is substitutable with a group represented by —(A¹)$_m$—NH—B in any substitutable position on the aliphatic carbon ring, which is substitutable with a lower alkyl group(s) in any substitutable position on the aliphatic carbon ring. Examples of the spiro cyclic group include, where n=0, groups having a group that can be represented by —(A¹)$_m$—NH—B on its aliphatic carbon ring, such as 5-azaspiro[2.4]hept-5-yl, 6-azaspiro [3.4]oct-6-yl, 2-azaspiro[4.4]non-2-yl, 2-azaspiro [4.5]dec-2-yl, 2-azaspiro[4.6]undec-2-yl, 2-azaspiro [4.7]dodec-2-yl, 5-azaspiro[2.4]hepten-5-yl, 6-azaspiro[3.4]octen-6-yl, 2-azaspiro[4.4]non-6-en-2-yl and 2-azaspiro[4.5]dec-6-en-2-yl groups, of which 5-azaspiro[2.4]hept-5-yl and 2-azaspiro[4.4]non-2-yl groups are more preferable; where n=1, examples include groups having a group that can be represented by —(A¹)$_m$NH—B on its aliphatic carbon ring, such as 6-azaspiro [2.5]oct-6-yl, 7-azaspiro[3.5]non-7-yl, 8-azaspiro [4.5]dec-8-yl, 3-azaspiro[5.5]undec-3-yl, 3-azaspiro [5.6]dodec-3-yl, 3-azaspiro[5.7]tridec-3-yl, 6-azaspiro[2.5]octen-6-yl, 7-azaspiro[3.5]nonen-7-yl, 8-azaspiro[4.5]decen-8-yl and 3-azaspiro[5.5]undec-7-en-3-yl groups, of which more preferable ones include 6-azaspiro[2.5]oct-6-yl and 8-azaspiro [4.5]dec-8-yl groups.

Examples of A¹ in a group represented by —(A¹)$_m$—NH—B on the ring include similar groups cited earlier with respect to A¹ in R², of which more preferable ones include methylene and ethylene groups.

Examples of B in a group represented by —(A¹)$_m$—NH—B on the ring include similar groups cited earlier with respect to B in the group represented by —(A¹)$_m$—NH—B in R², and the same is true with more preferable examples.

For m in the group represented by —(A¹)$_m$—NH—B on the ring, 0 is preferable.

Therefore, preferable examples of the group represented by —(A¹)$_m$—NH—B on the ring include amino, aminomethyl and aminoethyl groups, of which more preferable ones include an amino group.

The "$C_2$–$C_8$ aliphatic nitrogen-containing heterocyclic group containing an imino group, which is substitutable with a lower alkyl group" meant by R² and R⁴ combined, together with the adjoining two of the carbon atoms on the ring, constitutes, together with a cyclic group sharing carbon atoms on the ring, a bicyclo cyclic group which is substitutable with a lower alkyl group(s) in any substitutable position. Examples of the bicyclo groups include, where n=0, 3,6-diazabicyclo [3.1.0]hex-3-yl, 3,6-diazabicyclo [3.2.0]hept-3-yl, 3,6-diazabicyclo[3.3.0]oct-3-yl, 3,7-diazabicyclo [3.3.0]oct-3-yl, 2,8-diazabicyclo[4.3.0]non-8-yl, 3,8-diazabicyclo[4.3.0]non-8-yl, 2,9-diazabicyclo [5.3.0]dec-9-yl, 3,9-diazabicyclo[5.3.0]dec-9-yl, 4,9-diazabicyclo [5.3.0]dec-9-yl and 2,8-diazabicyclo [4.3.0]non-4-en-8-yl groups, of which more preferable ones include 3,7-diazabicyclo[3.3.0]oct-3-yl, 4,9-diazabicyclo[5.3.0]dec-9-yl and 3,8-diazabicyclo[4.3.0]non-8-yl groups; for n=1, examples include 3,7-diazabicyclo[4.1.0]hept-3-yl, 3,7-diazabicyclo[4.2.0]oct-3-yl, 3,8-diazabicyclo[4.2.0]oct-3-yl, 3,7-diazabicyclo[4.3.0]non-3-yl, 3,8-diazabicyclo[4.3.0]non-3-yl, 4,7-diazabicyclo[4.3.0]non-4-yl, 3,7-diazabicyclo [4.4.0]dec-3-yl, 3,8-diazabicyclo[4.4.0]dec-3-yl, 3,9-diazabicyclo[4.4.0]dec-3-yl, 4,7-diazabicyclo[4.4.0]dec-4-yl, 2,9-diazabicyclo[5.4.0]undec-9-yl, 3,9-diazabicyclo [5.4.0]undec-9-yl, 4,9-diazabicyclo[5.4.0]undec-9-yl, 3,10-diazabicyclo[5.4.0]undec-10-yl, 2,10-diazabicyclo[5.4.0] undec-10-yl, 3,7-diazabicyclo[4.4.0]dec-9-en-3-yl and 4,7-diazabicyclo [4.4.0]dec-9-en-4-yl groups, of which more preferable ones include 3,7-diazabicyclo[4.4.0]dec-3-yl, 3,8-diazabicyclo[4.4.0]dec-3-yl and 3,9-diazabicyclo[4.4.0] dec-3-yl groups.

Preferable examples of R² include a group which can be represented by —(A¹)$_m$—NH—B; a $C_2$–$C_8$ aliphatic nitrogen-containing heterocyclic group containing an imino group, which is substitutable with a lower alkyl group meant by R² and R³ combined, together with the adjoining one of the carbon atoms on the ring and a $C_2$–$C_8$ aliphatic nitrogen-containing heterocyclic group containing an imino group, which is substitutable with a lower alkyl group meant by R² and R⁴ combined, together with the adjoining two of the carbon atoms on the ring.

R³ means a hydrogen atom or a $C_1$–$C_6$ aliphatic hydrocarbon group which is substitutable with a lower alkyl group; or, combined with R⁵, means a single bond; or, combined with R², means the same as the foregoing.

The "$C_1$–$C_6$ aliphatic hydrocarbon group which is substitutable with a lower alkyl group" means said $C_1$–$C_6$ aliphatic hydrocarbon group having undergone no substitution or said $C_1$–$C_6$ aliphatic hydrocarbon group having a lower alkyl group(s) in any substitutable position, wherein 1, 2 or more, or preferably 1 or 2, which may be either the same as or different from each other, of the lower alkyl group(s) is substitutable on the aliphatic hydrocarbon group.

Preferable examples of lower alkyl group as the substitutive group include methyl, ethyl, propyl and isopropyl groups.

Therefore, examples of $C_1$–$C_6$ aliphatic hydrocarbon group which is substitutable with a lower alkyl group of $R^3$ include methyl, ethyl, propyl, isopropyl, 1-propenyl, isopropenyl and ethynyl groups, of which more preferable ones include methyl and ethyl groups.

That $R^3$ and $R^5$ combined mean a single bond means that they, together with an existing bond, forms a double bond on the ring.

Preferable examples of $R^3$ include a hydrogen atom, and methyl and ethyl groups; and a $C_2$–$C_8$ aliphatic nitrogen-containing heterocyclic group containing an imino group, which is substitutable with a lower alkyl group meant by $R^2$ and $R^3$ combined, together with the adjoining one of the carbon atoms on the ring.

$R^4$ means a hydrogen atom or a group represented by —$(A^1)_m$—NH—B; or, combined with $R^5$ means a group represented by =$A^2$—NH—B; or, together with the adjoining one of the carbon atoms on the ring, means a $C_2$–$C_8$ aliphatic nitrogen-containing heterocyclic group containing an imino group, which is substitutable with a lower alkyl group, or a $C_3$–$C_8$ aliphatic carbocyclic group having on the ring a group represented by —$(A^1)_m$—NH—B, which is substitutable with a lower alkyl group; or, combined with $R^2$, means the same as the foregoing.

Examples of $A^1$, B and m in the group represented by —$(A^1)_m$—NH—B of $R^4$ include similar groups cited earlier with respect to $A^1$, B and m in the group represented by —$(A^1)_m$—NH—B in $R^2$, and the same is true with more preferable examples.

Therefore, examples of the group represented by —$(A^1)_m$—NH—B of $R^4$ include similar groups cited earlier with respect to the group represented by —$(A^1)_m$—NH—B in $R^2$, and the same is true with more preferable examples.

Examples of $A^2$ and B in a group represented by =$A^2$—NH—B meant by $R^4$ and $R^5$ combined include similar groups cited earlier with respect to $A^2$ and B in a group represented by =$A^2$—NH—B meant by $R^2$ and $R^3$ combined, and the same is true with more preferable examples.

Therefore, examples of the group represented by =$A^2$—NH—B meant by $R^4$ and $R^5$ combined include similar groups cited earlier with respect to the group represented by =$A^2$—NH—B meant by $R^2$ and $R^3$ combined, and the same is true with more preferable examples.

The "$C_2$–$C_8$ aliphatic nitrogen-containing heterocyclic group containing an imino group, which is substitutable with a lower alkyl group" meant by $R^4$ and $R^5$ combined, together with the adjoining one of the carbon atoms on the ring, constitutes, together with a cyclic group sharing a carbon atom on the ring, a spiro cyclic group which is substitutable with a lower alkyl group(s) in any substitutable position. Examples of the spiro cyclic group include, where n=0, similar groups cited earlier with respect to the spiro cyclic group formed by said $R^2$ and $R^3$ combined where n=0, and the same is true with more preferable examples. Where n=1, examples include 1,5-diazaspiro[2.5]oct-5-yl, 1,6-diazaspiro[3.5]non-6-yl, 2,6-diazaspiro[3.5]non-6-yl, 1,7-diazaspiro[4.5]dec-7-yl, 2,7-diazaspiro[4.5]dec-7-yl, 1,8-diazaspiro[5.5]undec-8-yl, 2,8-diazaspiro[5.5]undec-2-yl, 2,9-diazaspiro[5.5]undec-2-yl, 2,7-diazaspiro[5.6]dodec-2-yl, 2,8-diazaspiro[5.6]dodec-2-yl, 2,9-diazaspiro[5.6]dodec-2-yl, 2,7-diazaspiro[5.7]tridec-2-yl, 2,8-diazaspiro[5.7]tridec-2-yl, 2,9-diazaspiro[5.7]tridec-2-yl, 2,10-diazaspiro[5.7]tridec-2-yl, 1,7-diazaspiro[4.5]dec-3-en-7-yl, 1,8-diazaspiro[5.5]undec-3-en-8-yl, 1,8-diazaspiro [5.5]undec-4-en-8-yl and 2,8-diazaspiro[5.5]undec-4-ene-8-yl groups, of which more preferable ones include 2,7-diazaspiro[4.5]dec-7-yl and 2,9-diazaspiro[5.5]undec-2-yl groups.

The "$C_3$–$C_8$ aliphatic carbocyclic group having on the ring a group represented by —$(A^1)_m$—NH—B, which is substitutable with a lower alkyl group" meant by $R^4$ and $R^5$ combined, together with the adjoining one of the carbon atoms on the ring, constitutes, together with a cyclic group sharing a carbon atom on the ring, a spiro cyclic group having a group represented by —$(A^1)_m$—NH—B in any substitutable position on the aliphatic carbon ring, which is substitutable with a lower alkyl group(s) in any substitutable position on the aliphatic carbon ring. Examples of the spiro cyclic group include, where n=0, similar groups cited earlier with respect to the spiro cyclic group formed by said $R^2$ and $R^3$ combined where n=0, and the same is true with more preferable examples. Where n=1, examples include groups having on the aliphatic carbon ring a group represented by —$(A^1)_m$—NH—B, such as 5-azaspiro[2.5]oct-5-yl, 6-azaspiro[3.5]non-6-yl, 7-azaspiro[4.5]dec-7-yl, 2-azaspiro[5.5]undec-2-yl, 2-azaspiro[5.6]dodec-2-yl, 2-azaspiro[5.7]tridec-2-yl, 5-azaspiro[2.5]octen-5-yl, 6-azaspiro[3.5]nonen-6-yl, 7-azaspiro[4.5]decene-7-yl and 2-azaspiro[5.5]undec-7-en-2-yl groups, of which more preferable ones include 5-azaspiro[2.5]oct-5-yl and 7-azaspiro[4.5]dec-7-yl groups.

Examples of the group represented by —$(A^1)_m$—NH—B on the ring include similar groups cited earlier with respect to the group represented by —$(A^1)_m$—NH—B on the spiro cyclic group formed by $R^2$ and $R^3$ combined, and the same is true with more preferable examples.

$R^5$ means a hydrogen atom or a $C_1$–$C_6$ aliphatic hydrocarbon group which is substitutable with a lower alkyl group, or, combined with $R^3$ or $R^4$, means respectively the same as the foregoing.

Examples of the "$C_1$–$C_6$ aliphatic hydrocarbon group which is substitutable with a lower alkyl group" of $R^5$ include similar groups cited earlier with respect to the "$C_1$–$C_6$ aliphatic hydrocarbon group which is substitutable with a lower alkyl group" of $R^3$, and the same is true with more preferable examples.

Preferable examples of $R^5$ include a hydrogen atom, and methyl and ethyl groups.

In preferable modes of $R^2$, $R^3$, $R^4$ and $R^5$ include, for instance, either $R^2$ or $R^4$ is a group represented by —$(A^1)_m$—NH—B, $R^2$ and $R^3$ combined, together with the adjoining one of the carbon atoms on the ring, constitute a $C_2$–$C_8$ aliphatic nitrogen-containing heterocyclic group containing an imino group, which is substitutable with a lower alkyl group, or $R^2$ and $R^4$ combined, together with the adjoining two of the carbon atoms on the ring, constitute a $C_2$–$C_8$ aliphatic nitrogen-containing heterocyclic group containing an imino group, which is substitutable with a lower alkyl group.

Sign n means either 0 or 1.

X means an oxygen or a sulfur atom, of which an oxygen atom is preferable.

According to the present invention, (a) $R^2$ and $R^4$ do not mean a hydrogen atom at the same time, (b) when either $R^2$ or $R^4$ is a group represented by —$(A^1)_m$—NH—B, the other means a hydrogen atom, (c) when $R^2$ and $R^3$ combined means the same as the foregoing, $R^4$ means a hydrogen atom, and (d) when $R^4$ and $R^5$ combined means the same as the foregoing, $R^2$ means a hydrogen atom.

Therefore, specific examples of compounds represented by the general formula [I] include:

4-amino-1-{(2R)-2-((1R)-3, 3-difluorocyclopentyl)-2-hydroxy-2-phenylacetyl}piperidine, 4-amino-1-{(2R)-2-cyclopentyl-2-hydroxy-2-phenylacetyl}piperidine, 4-amino-1-{(2R)-2-((1R)-3, 3-difluorocyclopentyl)-2-hydroxy-2-phenylacetyl}-4-methylpiperidine, 4-amino-1-{(2R)-2-cyclopentyl-2-hydroxy-2-phenylacetyl}-4-methylpiperidine, 4-amino-1-{(2R)-2-((1R)-3, 3-difluorocyclopentyl)-2-hydroxy-2-phenylacetyl}-4-ethylpiperidine, 4-amino-1-((2R)-2-cyclopentyl-2-hydroxy-2-phenylacetyl)-4-ethylpiperidine, 4-aminomethyl-1-{(2R)-2-((1R)- 3,3-difluorocyclopentyl) -2-hydroxy-2-phenylacetyl}piperidine, 4-aminomethy -1-((2R) -2-cyclopentyl-2-hydroxy-2-phenylacetyl)piperidine, 4-aminomethyl-1-{(2R)-2-((1R)-3, 3-difluorocyclopentyl)-2-hydroxy-2-phenylacetyl}-4-methylpiperidine, 4-aminomethyl-1-{(2R)-2-((1R)-3, 3-difluorocyclopentyl)-2-hydroxy-2-phenylacetyl}-4-ethylpiperidine, 4-(1-aminoethyl)-1-{(2R)-2-((1R)-3, 3-difluorocyclopentyl)-2-hydroxy-2-phenylacetyl}piperidine, 4-(1-aminoethyl)-1-((2R)-2-cyclopentyl-2-hydroxy-2-phenylacetyl)piperidine 4-(2-aminoethyl)-1-{(2R)-2-((1R)-3, 3-difluorocyclopentyl)-2-hydroxy-2-phenylacetyl}piperidine, 4-(2-aminoethyl)-1-((2R)-2-cyclopentyl-2-hydroxy-2-phenylacetyl)piperidine, 4-(2-aminoethyl)-1-{(2R)-2-((1R)-3, 3-difluorocyclopentyl)-2-hydroxy-2-phenylacetyl}-4-methylpiperidine, 4-(2-amino-1-methylethyl)-1-(2R)-2-((1R)-3,3-difluorocyclopentyl)-2-hydroxy-2-phenylacetyl]piperidine, 4-(2-amino-1-methylethyl)-1-((2R)-2-cyclopentyl-2-hydroxy-2-phenylacetyl)piperidine, 4-(1-aminomethylpropyl)-1-{(2R)-2-((1R)-3,3-difluorocyclopentyl)-2-hydroxy-2-phenylacetyl}piperidine, 4-(2-aminopropyl)-1-{(2R)-2-((1R)-3,3-difluorocyclopentyl)-2-hydroxy-2-phenylacetyl}piperidine, 4-(2-aminopropyl)-1-((2R)-2-cyclopentyl-2-hydroxy-2-phenylacetyl)piperidine, 4-(2-aminobutyl)-1-{(2R)-2-((1R)-3, 3-difluoroycyclopentyl)-2-hydroxy-2-phenylacetyl}piperidine, 4-(2-aminopentyl)-1-{(2R)-2-((1R)-3,3-diflurocyclopentyl)-2-hydroxy-2-phenylacetyl}piperidine, 4-(2-amino-2-methylpropyl)-1-{(2R)-2-((1R)-3,3-difluorocyclopentyl)-2-hydroxy-2-phenylacetyl}-piperidine, 4-(2-aminoethylidene)-1-{(2R)-2-((1R)-3,3-difluorocyclopentyl)-2-hydroxy-2-phenylacetyl}piperidine, 4-(2-aminoethyl)-1-{(2R)-2-((1R)-3, 3-difluorocyclopentyl)-2-hydroxy-2-phenylacetyl}-1,2, 3,6-tetrahydropyridine, 8-{(2R)-2-((1R)-3,3-difluorocyclopentyl)-2-hydroxy)-2-phenylacetyl}-2,8-diazaspiro[4.5]decane, 1-aminomethyl-6-{(2R)-2-((1R)-3, 3-difluorocyclopentyl)-2-hydroxy-2-phenylacetyl}-6-azaspiro[2.5]-octane, 2-{(2R)-2-((1R)-3,3-difluorocyclopentyl)-2-hydroxy-2-phenylacetyl}-2,8-diazaspiro[4.5]decane, 9-{(2R)-2-((1R)-3,3-difluorocyclopentyl)-2-hydroxy-2-phenylacetyl}-cis-4,9-diazabicyclo[5.3.0]-decane, 3-{(2R)-2-((1R)-3,3-difluorocyclopentyl)-2-hydroxy-2-phenylacetyl}-3,7-diazabicyclo[3.3.0]octane, 7-{(2R)-2-((1R)-3,3-difluorocyclopentyl)-2-hydroxy-2-phenylacetyl}-2,7-diazaspiro[4.5]decane, 3-{(2R)-2-((1R)-3,3-difluorocyclopentyl)-2-hydroxy-2-phenylacetyl}-3,9-diazaspiro[5.5]undecane, 9-{(2R)-2-((1R)-3,3-difluorocyclopentyl)-2-hydroxy-2-phenylacetyl}-2,9-diazaspiro[5.5]undecane, 2-{(2R)-2-((1R)-3,3-difluorocyclopentyl)-2-hydroxy-2-phenylacetyl}-2,7-diazaspiro[4.4]nonane, 3-{(2R)-2-((1R)-3,3-difluorocyclopentyl)-2 -hydroxy-2-phenylacetyl}-3,7-diazabicyclo[3.3.0]oct-1(5)-ene, 2-{(2R)-2-((1R)-3,3-difluorocyclopentyl)-2-hydroxy-2-phenylacetyl}-4-methyl-2,8-diazaspiro[4.5]-decane, 8-{(2R)-2-((1R)-3,3-difluorocyclopentyl)-2-hydroxy-2-phenylacetyl}-3-methyl-2,8-diazaspiro[4.5]-decane, 8-{(2R)-2-((1R)-3,3-difluorocyclopentyl)-2-hydroxy-2-phenylacetyl}-4-methyl-2,8-diazaspiro[4.5]-decane, 5 7-{(2R)-2-((1R)-3,3-difluorocyclopentyl)-2-hydroxy-2-phenylacetyl}-2,7-diazaspiro[3.5]nonane, 3-{(2R) -2-((1R)-3,3-difluorocyclopentyl)-2-hydroxy-2-phenylacetyl}-3,8-diazabicyclo[4.3.0]nonane, 8-{(2R)-2-((1R)-3,3-difluorocyclopentyl)-2-hydroxy-2-phenylacetyl}-3,8-diazabicyclo[4.3.0]nonane, 9-{(2R)-2-((1R)-3,3-difluorocyclopentyl)-2-hydroxy-2-phenylacetyl}-3,9-diazabicyclo[5.3.0]decane, 8-{(2R)-2-((1R)-3,3-difluorocyclopentyl)-2-hydroxy-2-phenylacetyl}-1-methyl-2,8-diazaspiro[4.5]-decane, 2-{(2R)-2-((1R)-3,3-difluorocyclopentyl)-2-hydroxy-2-phenylacetyl}-2,7-diazaspiro[4.5]decane, 9-{(2R)-2-((1R)-3,3-difluorocyclopentyl)-2-hydroxy-2-phenylacetyl}-4,9-diazabicyclo[5.3.0]decane, 8-{(2R)-2-((1R)-3,3-difluorocyclopentyl)-2-hydroxy-2-phenylacetyl}-1-ethyl-2,8-diazaspiro[4.5]-decane, 9-{(2R)-2-((1R)-3,3-difluorocyclopentyl)-2-hydroxy-2-phenylacetyl}-3-methyl-cis-4,9-diazabicyclo[5.3.0] decane, 4-aminomethyl-1-{(2R)-2-((1R)-3,3-difluorocyclopentyl)-2-hydroxy-2-phenylacetyl}-1,2, 3,6-tetrahydropyridine, and 2-{(2R)-2-((1R)-3,3-difluorocyclopentyl)-2-hydroxy-2-phenylacetyl}-2,7-diazaspiro[4.5]decane, of which more preferable ones include:

4-amino-1-{(2R)-2-((1R)-3,3-difluorocyclopentyl)-2-hydroxy-2-phenylacetyl}piperidine, 4-(2-aminoethyl)-1-{(2R)-2-((1R)-3,3-difluorocyclopentyl)-2-hydroxy-2-phenylacetyl}piperidine, 8-{(2R)-2-((1R)-3,3-difluorocyclopentyl)-2-hydroxy-2-phenylacetyl}-2,8-diazaspiro[4.5]decane, 9-{(2R)-2-((1R)-3,3-difluorocyclopentyl)-2-hydroxy-2-phenylacetyl}-cis-4,9-diazabicyclo[5.3.0]-decane, 3-{(2R)-2-((1R)-3,3-difluorocyclopentyl)-2-hydroxy-2-phenylacetyl}-3,7-diazabicyclo[3.3.0]oct-1(5)-ene, and 8-{(2R)-2-((1R)-3,3-difluorocyclopentyl)-2-hydroxy-2-phenylacetyl}-1-methyl-2,8-diazaspiro[4.5]-decane.

Next will be described manufacturing processes for compounds according to the invention.

Compounds [I] of the present invention can be produced by manufacturing processes described below, methods stated in preferred embodiments or the like.

However, manufacturing methods for compounds [I] according to the invention are not confined to these examples of reaction.

Manufacturing Process 1

A compound represented by the general formula [I] can be produced by reacting a compound represented by the general formula [III]

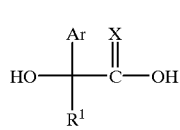

[III]

or reactive derivatives thereof [wherein Ar, $R^1$ and X have the respective meanings stated earlier] with a compound represented by the general formula [IV]

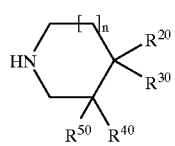

[IV]

[wherein $R^{20}$ means a hydrogen atom or a group represented by —$(A^1)_m$—$N(P^1)$—$B^p$; or, combined with $R^{30}$, means a group represented by =$A^2$—N ($P^1$)—$B^p$, or, together with the adjoining one of the carbon atoms on the ring, means a $C_2$–$C_8$ aliphatic nitrogen-containing heterocyclic group containing a protectable imino group, which is substitutable with a lower alkyl group, or a $C_3$–$C_8$ aliphatic carbocyclic group having on the ring a group represented by —$(A^1)_m$—$N(P^1)$—$B^p$, which is substitutable with a lower alkyl group; or, combined with $R^{40}$, together with the adjoining two of the carbon atoms on the ring, means a $C_2$–$C_8$ aliphatic nitrogen-containing heterocyclic group containing a protectable imino group, which is substitutable with a lower alkyl group; $R^{30}$ means a hydrogen atom or a $C_1$–$C_6$ aliphatic hydrocarbon group which is substitutable with a lower alkyl group, or, combined with $R^{50}$, means a single bond, or, combined with $R^{20}$, means the same as the foregoing; $R^{40}$ means a hydrogen atom or a group represented by —$(A^1)_m$—$N(P^1)$—$B^p$, or, combined with $R^{50}$, means a group represented by =$A^2$—$N(P^1)$—$B^p$, or, together with the adjoining one of the carbon atoms on the ring, means a $C_2$–$C_8$ aliphatic nitrogen-containing heterocyclic group containing a protectable imino group, which is substitutable with a lower alkyl group, or a $C_3$–$C_8$ aliphatic carbocyclic group having on the ring a group represented by —$(A^1)_m$—$N(P^1)$—$B^p$, which is substitutable with a lower alkyl group; or, combined with $R^{20}$, means the same as the foregoing; $R^{50}$ means a hydrogen atom or a $C_1$–$C_6$ aliphatic hydrocarbon group which is substitutable with a lower alkyl group, or, combined with $R^{30}$ or $R^{40}$, means respectively the same as the foregoing; $B^p$ means a hydrogen atom or a $C_1$–$C_6$ aliphatic hydrocarbon group which may have a substitutive group selected from a group consisting of a lower alkyl group and an aryl group, or, combined with $P^1$, means an amino group-protective group; $P^1$ means a hydrogen atom or a protective group for an amino group or an imino group, or, combined with $B^p$, means the same as the foregoing; and $A^1$, $A^2$, m and n mean the same as the foregoing (provided that (a) $R^{20}$ and $R^{40}$ do not mean a hydrogen atom at the same time, (b) when either $R^\circ$ or $R^{40}$ is a group represented by —$(A^1)_m$—$N(P^1)$—$B^p$, the other means a hydrogen atom, (c) when $R^{20}$ and $R^{30}$ combined mean the same as the foregoing, $R^{40}$ means a hydrogen atom, and (d) when $R^{40}$ and $R^{50}$ combined mean the same as the foregoing, $R^{20}$ means a hydrogen atom)] or a salt thereof to remove a protective group for an amino or imino group; after, as required, (a) a reductive amination with an aldehyde or a ketone represented by the general formula [V]

$$O=B^{10} \qquad [V]$$

[wherein $B^{10}$ means a $C_1$–$C_6$ aliphatic hydrocarbon group, which may have a substitutive group selected from a group consisting of a lower alkyl group and an aryl group] or (b) removal of any protective group for an amino or imino group involved in the reaction while protecting a hydroxyl or oxo group not involved in the reaction, carrying out a reaction with a compound represented by the general formula [V'] in the presence of a base $$L—B \qquad [V']$$

[wherein L means a leaving group, and B means the same as the foregoing], and then removing, as required, any protective group for an amino, imino, hydroxyl or oxo group.

In this manufacturing process, the compound represented by the general formula [III] is reacted in the presence of the compound represented by the general formula [IV] or a salt thereof and a suitable condensing agent, with the result that the a coupling compound represented by the following general formula [VII]

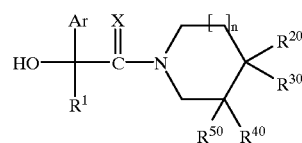

[VII]

[wherein Ar, n, $R^1$, $R^{20}$, $R^{30}$, $R^{40}$, $R^{50}$ and X mean respectively the same as the foregoing].

Preferable condensing agents for use in the above-mentioned reaction include those usually employed in the field of organic synthetic chemistry for condensing reactions between a carboxyl group and a hydroxyl or amino group, such as N,N'-dicyclohexylcarbodimide, 1-ethyl-3-(3-dimethylaminopropyl) carbodimide, diphenylphosphorylazide and dipyridyldisulfide-triphenylphosphine, of which 1-ethyl-3-(3-dimethylaminopropyl) carbodimide is particularly preferable.

The amount of any of these condensing agents, though not strictly limited, can usually be 1 to 5 equivalents, more particularly within the range of 1 to 2 equivalents, to 1 unit of the compound represented by the formula [III].

Also, the aforementioned condensing reaction may be carried out, if required, in the presence of a base, and usable bases including aliphatic tertiary amines such as triethylamine and disopropylethylamine, and aromatic amines such as pyridine, 4-dimethylaminopyridine and quinoline, of which particularly preferable ones include 4-dimethylaminopyridine.

The condensing reaction should preferably be carried out in an inactive solvent, and examples of such inactive organic solvents include diethyl ether, tetrahydrofuran, N,N-dimethylformamide, dioxane, benzene, toluene, chlorobenzene, methylene chloride, chloroform, carbon tetrachloride, dichloroethane and trichloroethylene or mixtures thereof, of which particularly preferable ones include diethyl ether, tetrahydrofuran, N,N-dimethylformamide and dioxane.

The reaction temperature can usually be −70° C. to the boiling of the solvent used in the reaction, preferably within the range of −20° C. to 100° C., and the reaction under this condition can usually be completed in 5 minutes to 7 days, preferably in 10 minutes to 24 hours.

Whereas the ratio of any compound of the formula [IV] or a salt thereof to be used to any compound of [III] is nothing to be strictly limited, but can be varied with the kinds of these compounds and/or the reaction conditions used, a compound of the formula [IV] or a salt thereof can be used in 1 to 5 mols, preferably within the range of 1 to 2 mols, per mol of a compound of the formula [III].

Further, the aforementioned coupling compound of the formula [VII] can as well be obtained by condensing a reactive derivative, into which a compound of the formula [III] has been converted, with a compound of the formula [IV] or a salt thereof.

Examples of reactive derivative of a compound of the formula [III] include what are commonly used in the field of organic synthetic chemistry for the activation of a carboxyl group in esterification or amidation, such as mixed acid anhydrides, active esters and active amides.

A mixed acid anhydride of a compound of the formula [Ill] can be obtained by reacting the compound of the formula [III] by a conventional method with, for example, an alkyl chloroformate such as ethyl chloroformate or an alkanoyl chloride such as acetyl chloride or pivaloyl chloride; an active ester can be obtained by reacting the compound of the formula [III] by a conventional method with, for example, an N-hydroxy compound such as N-hydroxysuccineimide, N-hydroxyphthal imide or 1-hydroxybenzotriazole, or a phenol compound such as 4-nitrophenol, 2,4-dinitrophenol, 2,4,5-trichlorophenol or pentachlorophenol in the presence of a condensing agent such as N,N'-dicyclohexylcarbodimide, 1-ethyl-3-(3-dimethylaminopropyl) carbodimide, diphenylphosphorylazide or dipyridyidisulfide-triphenylphosphine; and an active amide can be obtained by reacting the compound of the formula [III] by a conventional method with, for example, 1,1'-carbonyldi imidazole or 1,1'-carbonylbis (2-metholimidazole).

The condensing reaction between a reactive derivative of a compound of the formula [III] and a compound of the formula [IV] or a salt thereof should preferably be carried out in an inactive solvent, and examples of such inactive organic solvents include diethyl ether, tetrahydrofuran, N,N-dimethylformamide, dioxane, benzene, toluene, chlorobenzene, methylene chloride, chloroform, carbon tetrachloride, dichloroethane and trichloroethylene or mixtures thereof, of which particularly preferable ones include diethyl ether, chloroform, tetrahydrofuran, N,N-dimethylformamide and dioxane.

The reaction temperature can usually be −70° C. to the boiling point of the solvent used in the reaction, preferably within the range of −20° C. to 100° C.

Whereas the ratio of any compound of the formula [IV] or a salt thereof to be used to any ractive derivative of a compound of [III] is nothing to be strictly limited, but can be varied with the kinds of these compounds and the like, a compound of the formula [IV] or a salt thereof can be used in 1 to 5 mols, preferably within the range of 1 to 2 mols, per mol of a ractive derivative of a compound of the formula [III].

The reductive amination reaction with a ketone or an aldehyde in step (a) is usually carried out in an inactive solvent, which would have no adverse effect on the reaction.

Such inactive solvents include alcohols such as methanol and ethanol; and ethers such as diethyl ether, tetrahydrofuran and dioxane, aromatic hydrocarbons such as benzene and toluene or mixtures thereof, of which more preferable ones include methanol, ethanol, tetrahydrofuran and toluene.

The reaction temperature can usually be about −30° C. to about 200° C., preferably from about 0° C. to about 100° C., and the reaction under this condition can usually be completed in 10 minutes to 7 days, preferably in 10 minutes to 24 hours.

The aforementioned reductive amination can be carried out by using a metal hydride complex such as sodium borohydride, sodium cyanoborohydride or sodium triacetoxyborohydride or catalytic reduction using a palladium-carbon catalyst or a Raney nickel catalyst.

Where a metal hydride complex is used as the reducing agent, the dose of the reducing agent can usually be 1 mol to excessive mols, preferably from 1 to 10 mols per mol of the starting compound, i.e. the compound of the formula [VII] cleared of any protective group.

The reaction with a compound represented by the general formula [V'] in step (b) is usually carried out in an inactive solvent, which would have no adverse effect on the reaction, in the presence of a base.

Examples of the base include hydrogen carbonates of alkaline metals such as sodium hydrogen carbonate and potassium hydrogen carbonate; carbonates of alkaline metals such as sodium carbonate and potassium carbonate; tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo [5.4.0]undec-7-ene (DBU) and 1,5-diazabicyclo[4.3.0]non-5-ene (DBN); and aromatic amines such as pyridine, 4-dimethylaminopyridine, picoline, lutidine, quinoline and isoquinoline, of which preferable ones include N,N-diiopropylethylamine and potassium carbonate.

The amount of the base can usually be 1 mol to excessive mols, preferably from 1 to 10 mols per mol of the starting compound, i.e. the compound of the formula [VII] removed any protective group from.

Such inactive solvents include ethers such as diethyl ether, tetrahydrofuran and dioxane, aromatic hydrocarbons such as benzene, toluene, chlorobenzene and xylene, and nonprotonic polar solvents such as dimethyl sulfoxide, N,N-dimethylformamide, acetonitrile and hexamethylphosphoric triamide or mixtures thereof.

The reaction temperature is usually about 0° C. to the boiling point of the solvent, and the reaction time can be 10 minutes to 48 hours, but conditions either above or below these may be used as required.

In this manufacturing process, the introduction or removal of protective groups for amino, imino, hydroxyl and oxo groups can be accomplished by a method known in itself, for instance the method described in T. W. Greene, *Protective Groups in Organic Synthesis*, John Wiley & Sons (1981), or a method similar thereto.

Applicable methods to remove said protective groups include, for instance, solvolysis using an acid or an alkali, chemical reduction using a metal hydride complex or the like, or catalytic reduction using a palladium-carbon catalyst or a Raney nickel catalyst.

Solvolysis with an acid can usually be accomplished using an acid such as formic acid, trifluoroacetic acid, hydrochloric acid or sulfuric acid in a solvent such as methylene chloride, anisole, tetrahydrofuran, dioxane, methanol or ethanol or a mixture thereof with water or in the absence of any solvent by treatment for 10 minutes to 24 hours preferably in a temperature range of about 0° C. to about 100° C.

Solvolysis with a base is usually accomplished by an alkaline metal hydroxide such as lithium hydroxide, sodium hydroxide or potassium hydroxide, or a carbonate of an alkaline metal such as sodium carbonate or potassium carbonate to act in a solvent such as methanol, ethanol, isopropanol, tetrahydrofuran or dioxane or a mixture thereof with water for 10 minutes to 24 hours preferably in a temperature range of about −20° C. to about 80° C.

Catalytic reduction is usually accomplished by using a catalyst such as a palladium-carbon, palladium hydroxide, Raney nickel or platinum oxide catalyst in a solvent such as methanol, ethanol, water or acetic acid or a mixture thereof, preferably under a hydrogen pressure of about 1 to about 20 kg/cm, for 10 minutes to 24 hours preferably in a temperature of about 0° C. to about 40° C.

Manufacturing Process 2

A compound represented by the general formula [I1]

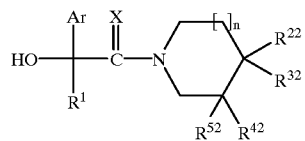

[I-1]

[wherein $R^{22}$ means a hydrogen atom or a group represented by $-(A^1)_m-NH-B$; or, combined with $R^{32}$, means a group represented by $=A^2-NH-B$, or, together with the adjoining one of the carbon atoms on the ring, means a $C_3-C_8$ aliphatic carbocyclic group having on the ring a group represented by $-(A^1)_m-NH-B$, which is substitutable with a lower alkyl group; $R^{32}$ means a hydrogen atom or a $C_1-C_6$ aliphatic hydrocarbon group which is substitutable with a lower alkyl group, or, combined with $R^{52}$, means a single bond, or, combined with $R^{22}$, means the same as the foregoing; $R^{42}$ means a hydrogen atom or a group represented by $-(A^1)_m-NH-B$, or, combined with $R^{52}$, means a group represented by $=A^2-NH-B$, or, together with the adjoining one of the carbon atoms on the ring, means a $C_3-C_8$ aliphatic carbocyclic group having on the ring a group represented by $-(A^1)_m-NH-B$, which is substitutable with a lower alkyl group; $R^{52}$ means a hydrogen atom or a $C_1-C_6$ aliphatic hydrocarbon group which is substitutable with a lower alkyl group, or, combined with $R^{32}$ or $R^{42}$, means respectively the same as the foregoing; and Ar, $R^1$, $A^1$, $A^2$, B, m, n and X mean respectively the same as the foregoing (provided that (a) $R^{22}$ and $R^{42}$ do not mean a hydrogen atom at the same time, (b) when either $R^{22}$ or $R^{42}$ is a group represented by $-(A^1)_m-NH-B$, the other means a hydrogen atom, (c) when $R^{22}$ and $R^{32}$ combined mean the same as the foregoing, $R^{42}$ means a hydrogen atom, and (d) when $R^{42}$ and $R^{52}$ combined mean the same as the foregoing, $R^{22}$ means a hydrogen atom)] can be produced by reacting a compound represented by the above-cited general formula [III] or a reactive derivative thereof with a compound represented by the general formula [VI]

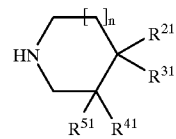

[VI]

[wherein $R^{21}$ means a hydrogen atom or a group represented by $-(A^{1a})_m-Q$; or, combined with $R^{31}$, means an oxo group or a group represented by $=A^{2a}-Q$, or, together with the adjoining one of the carbon atoms on the ring, means a $C_3-C_8$ aliphatic carbocyclic group having on the ring a group represented by $-(A^{1a})_m-Q$, which is substitutable with a lower alkyl group; $R^{31}$ means a hydrogen atom or a $C_1-C_6$ aliphatic hydrocarbon group which is substitutable with a lower alkyl group, or, combined with $R^{51}$, means a single bond, or, combined with $R^{21}$, means the same as the foregoing; $R^{41}$ means a hydrogen atom or a group represented by $-(A^{1a})_m-Q$, or, combined with $R^{51}$, means an oxo group or a group represented by $=A^{2a}_m-Q$, or, together with the adjoining one of the carbon atoms on the ring, means a $C_3-C_8$ aliphatic carbocyclic group having on the ring a group represented by $-(A^{1a})_m-Q$, which is substitutable with a lower alkyl group; $R^{51}$ means a hydrogen atom or a $C_1-C_6$ aliphatic hydrocarbon group which is substitutable with a lower alkyl group, or, combined with $R^{31}$ or $R^{41}$, means respectively the same as the foregoing; $A^{1a}$ means a $C_1-C_8$ bivalent aliphatic hydrocarbon group which is substitutable with a lower alkyl group; $A^{2a}$ means a $C1-C_8$ trivalent aliphatic hydrocarbon group which is substitutable with a lower alkyl group; Q means an azide, nitro, cyano, hydroxyl, oxo, lower alkoxycarbonyl or aralkyloxycarobonyl group or a halogen atom; and m and n mean the same as the foregoing (provided that (a) $R^{21}$ and $R^{41}$ do not mean a hydrogen atom at the same time, (b) when either $R^{21}$ or $R^{41}$ is a group represented by $-(A^{1a})_m-Q$, the other means a hydrogen atom, (c) when $R^{21}$ and $R^3$ combined mean the same as the foregoing, $R^{41}$ means a hydrogen atom, and (d) when $R^{41}$ and $R^{51}$ combined mean the same as the foregoing, $R^{21}$ means a hydrogen atom)] or a salt thereof, then, as required, protecting a hydroxyl or oxo group not involved in the reaction; subjecting the reaction product to a reaction to elongate the carbon atoms, reduction of any multiple bond, isomerization or oxidative cleavage, and reaction to add to, or eliminate from, the multiple bond water, ammonia, hydrogen halide, carbonyl, hydrogen cyanide or hydrogen azide in $R^{21}$, $R^{31}$, $R^{41}$ and $R^{51}$; then converting the azide, nitro, cyano, hydroxyl, oxo, lower alkoxylcarbonyl or aralkyloxycarbonyl group or halogen atom of the compound into amino groups; after, as required, (a) reductive amination with an aldehyde or a ketone represented by the above-cited general formula [V] or (b) removing any amino or imino group involved in the reaction while protecting any hydroxyl or oxo group not involved in the reaction; carrying out a reaction with a compound represented by the above-cited general formula [V'] in the presence of a base; and then removing, as required any protective group for an amino, imino, hydroxyl or oxo group.

The reaction between a compound of the general formula [III] or a reactive derivative thereof with a compound of the general formula [VI] can be carried out in the same manner as the reaction between a compound of the general formula [III] or a reactive derivative thereof with a compound of the general formula [IV] of the above-described manufacturing process 1. Therefore, similar reaction conditions can be applied, too.

Further, where there is any multiple bond in the hydrocarbon group of a compound of the general formula [VI], it is possible to introduce a group corresponding to Q by adding water, ammonia, hydrogen halide, carbonyl, hydrogen cyanide or hydrogen azide to the multiple bond in that compound, after reacting the compound whose Q is a hydrogen atom, which is a compound having no azide, nitro, cyano, hydroxyl, oxo, lower alkoxycarbonyl or aralkyloxycarbonyl group or halogen atom with a compound of the general formula [III].

The reaction to elongate the carbon atoms can be accomplished by a carbon-carbon bond forming reaction, a well known technique in the field of organic chemistry, and this carbon-carbon bond forming reaction includes, for example, substitution or addition reactions carried out in the presence of a base; addition reactions by using an organo-metallic reagent; Michael type addition, reaction with phosphonium salt or phosphonate in the presence of a base; Wittig-like reaction using a Tebbe type reagent, a Nozaki-Lombardo type reagent, a metal alkylydenecarbene complex or the like; addition reactions through the generation of anion seeds by performing halogen-metal exchange or the like after conversion into a halide, or by using an alkaline metal base or the like, such as n-butyllithium after conversion into tosylhydrazone, and the Simmons-Smith reaction.

Reduction of a multiple bond can be usually accomplished by a method well known in the field of organic chemistry, for instance by catalytic reduction using a metal catalyst such as a palladium-carbon catalyst or by reduction using a metal hydride complex.

Isomerization of a multiple bond can be usually accomplished by a method well known in the field of organic chemistry, for example by using a base or an acid under heating, or at low or high temperature, or by using an organic transition metal.

Oxidative cleavage of a multiple bond can be usually accomplished by a method well known in the field of organic chemistry, for instance by using sodium periodate and osmium tetraoxide, or sodium periodate and potassium permanganate, or by ozonolysis, a carbon-carbon double bond can be converted into two carbonyl groups.

Addition of water, ammonia, hydrogen halide, carbonyl, hydrogen cyanide or hydrogen azide to a multiple bond can usually be accomplished by a method well known in the field of organic chemistry.

Addition of water to a multiple bond can be achieved, for instance, by hydroboration, oxymercuration or the like.

Addition of ammonia to a multiple bond can be carried out, for example, by hydroamination or the like in the presence of an organic metal catalyst.

Addition of hydrogen halide to a multiple bond can be accomplished, for instance, by directly using hydrogen halide or reacting with halogen molecules after hydroboration.

Addition of a carbonyl group to a multiple bond can be carried out, for example, by hydroformylation or the like in the presence of an organo-metal catalyst.

Addition of hydrogen cyanide to a multiple bond can be achieved, for instance, by hydrocyanation in the presence of an organo-metal catalyst.

Addition of hydrazoic acid to a multiple bond can be performed, for example, by azidomercuration or the like.

Elimination can usually be accomplished by a method well known in the field of organic chemistry, for instance, by treating a sulfonate or a halide with a base.

Conversion of an azide, nitro, cyano, hydroxyl, oxo, lower alkoxycarbonyl or aralkyloxycarbonyl group or a halogen atom into an amino group can usually be accomplished by a method well known in the field of organic chemistry.

Conversion of an azide or a nitro group into an amino group can be carried out, for instance by catalytic reduction using a metal catalyst such as a palladium-carbon catalyst, phosphine reduction, reduction using a metal hydride complex, or otherwise.

Conversion of a halogen atom into an amino group can be achieved, for instance, by substitution with an amino group, or applying the above-described method after conversion into an azide group.

Conversion of a cyano group into an amino group can be carried out, for example, by reduction using a metal hydride complex or otherwise.

Conversion of a hydroxyl group to an amino group can be performed, for example, via a halogen atom, an azide group or the like.

Conversion of an oxo group into an amino group can be accomplished, for instance, by reductive amination, by substitution via hydroxyl group after reduction, or otherwise.

Conversion of a lower alkoxycarbonl group or an aralkyloxycarbonyl group into an amino group can be carried out, for example, the so-called Curtius, Schmidt or Hofmann dislocation, i.e. conversion into an acid azide after hydrolysis into carboxylic acid as required, followed by rearrangement and hydrolysis, or using the above-stated method via a hydroxyl group or an oxo group.

Reactions in steps (a) and (b), which are performed as required, can be carried out in the same manners as steps (a) and (b) in the manufacturing process 1. Accordingly, the same reaction conditions can be applied.

Introduction or removal of a protective group for an amino, imino, hydroxyl or oxo group can be carried out in the same manner as the method stated in the manufacturing process 1.

Any compound of the formula [I] or [I-1] obtained by one or the other of the manufacturing processes so far described can be purified and isolated by a method known in itself, including conventionally used separating methods, such as column chromatography, using silica gel or adsorptive resin, liquid chromatography, thin layer chromatography, extraction with solvent or recrystallization and retrituation.

Whereas any compound according to the invention, or any intermediate product thereof, may have stereoisomers including optical isomers, diastereomers and regio isomers, depending upon the form of its substituents, compounds according to the invention include substances in any stereoisomerically pure form or mixtures thereof.

Optical resolution of any compound according to the invention or any intermediate thereof which is a racemic compound can be accomplished by usual manners including high performance liquid chromatography using a chiral carrier or fractional crystallization of diastereomeric salt.

These compounds can be converted by usual methods into pharmaceutically acceptable salts, and conversely conversion from salts to free amines can also be accomplished by usual method.

Compounds represented by the general formulas [III], [IV], [V], [V'] or [VI] for use in the invention can either be procured in the market or produced by known methods, methods described in literature [see *Journal of Medicinal Chemistry* (J. Med. Chem.), vol. 25, p. 1103 (1982) or the International Laid-open WO 96/33973 Publication], methods substantially conforming thereto, the following methods, or methods stated in the description of embodiments and referential examples.

Any compound represented by the general formula [III] can be manufactured by subjecting, for example, a compound represented by the general formula [VIII]

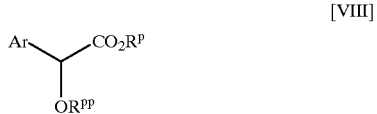

[wherein $R^P$ and $R^{PP}$ mean a carboxyl group-protective group and a hydroxyl group-protective group, respectively, and $R^P$ and $R^{PP}$ may as well be combined to constitute an acetal or a ketal; and Ar means the same as the foregoing], and a compound represented by the general formula [IX]

[wherein $R^{10}$ means a $C_3$–$C_{20}$ saturated or unsaturated aliphatic hydrocarbon group, which is substitutable with a leaving group or a protected hydroxyl or oxo group] to a conjugated addition or substitution in the presence of a base to give a compound represented by the general formula [X]

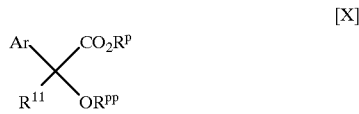

[wherein $R^{11}$ means a $C_3$–$C_{20}$ saturated or unsaturated aliphatic hydrocarbon group, which is substitutable with an unprotected or a protected hydroxyl or oxo group; and Ar, $R^P$ and $R^{PP}$ respectively mean the same as the foregoing], which is subjected, as required, to Retro-Deals Alder reaction, reduction of any multiple bond, deprotection of a hydroxyl or oxo group on $R^{11}$, reduction of an oxo group, or deoxygenation of a hydroxyl or oxo group, and further subjected, as required, to conversion of an unprotected or protected hydroxyl or oxo group into a fluorine atom, followed by deprotection of $R^P$ and $R^{PP}$.

As examples of $R^P$ and $R^{PP}$, the aforementioned protective groups can be cited, and they may be combined to constitute an acetal or a ketal, such as a t-butylydene acetal or an isopropylidene ketal.

As examples of compounds represented by the general formula [IX], for example 2-cyclopenten-1-one, 3-chloro-2-cyclopenten-1-one, 3-boromo-2-cyclopenten-1-one, 3-methoxy-2-cyclopenten-1-one, 3-ethoxy-2-cyclopenten-1-one, 3-acetoxy-2-cyclopenten-1-one and tricyclo [5.2.1.0$^{2,6}$]dec-4,8-dien-3-one can be cited.

Conjugated addition or substitution between any compound represented by the general formula [VIII] and any compound represented by the general formula [IX] can be accomplished by a method well known in the field of organic chemistry, and usually carried out by using a base, such as sodium hydride or lithium diisopropylamide, in an inactive solvent such as diethyl ether, tetrahydrofuran, N,N-dimethylformamide, dioxane, benzene, toluene, chlorobenzene or methylene chloride.

The Retro-Deals Alder reaction, reduction of any multiple bond, deprotection of any hydroxyl or oxo group on $R^{11}$, reduction of any oxo group or deoxygenation of any hydroxyl or oxo group can be usually accomplished by a method well known in the field of organic chemistry.

The Retro-Deals Alder reaction can be carried, for instance by direct heating, or treatment in the presence of Lewis acid as required, in an inactive solvent, such as toluene or dichlorobenzene, or in the absence of any solvent.

Deprotection of any hydroxyl or oxo group on $R^{11}$ can be achieved by the method described in the reference mentioned in the foregoing manufacturing process 1.

Reduction of any oxo group can be performed by using, for example, a metal hydride complex such as sodium borohydride or lithium aluminiumhydride.

Conversion of any unprotected or protected hydroxyl or oxo group into a fluorine atom can be accomplished by the method described in the Journal of the (Japanese) Society of Organic Synthetic Chemistry, vol. 51, p.22 (1993): for example, the compound is either directly, or after conversion of its hydroxyl or oxo group into dithioacetal, oxime, hydrazone or the like, is subjected to reaction for 10 minutes to 72 hours in a temperature range of preferably –80° C. to 180° C. in an inactive solvent having no adverse effect on the reaction, such as methylene chloride, chloroform, tetrahydrofuran, methanol, acetonitril, dimethyl sulfoxide or pyridine or in the absence of any solvent by using 1 to excessive equivalents, preferably 1 to 2 equivalents, of fluorinating agent, such as sulfur tetrafluoride, diethylaminosulfur trifluoride, cesium fluorosulfide, tetrabutyl ammonium fluoride, tris (dimethylamino) sulfoniumdifluorotrimetylsilicate, hydrogen fluoride or tosyl fluoride.

To add, compounds represented by the general formula [VIII] or [IX] are either commercially available or can be produced by appropriately combining, as required, known methods or methods similar thereto.

Any compound represented by the general formula [IV] can be produced, for instance, by subjecting a compound represented by the general formula [XI]

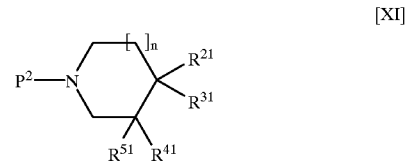

[wherein $P^2$ means an imino group-protective group; and $R^{21}$, $R^{31}$, $R^{41}$, $R^{51}$ and n respectively mean the same as the foregoing (though $R^{21}$ and $R^{41}$ here may mean a group represented by —$(A^{1a})_m$—Q at the same time)] to, as required, protection of a hydroxyl or oxo group not involved in the reaction, a reaction to elongate the carbon atoms, reduction of any multiple bond, isomerization or oxidative cleavage, and reaction to add to, or eliminate from, the multiple bond water, ammonia, hydrogen halide, carbonyl, hydrogen cyanide or hydrogen azide in $R^{21}$, $R^{31}$, $R^{41}$ and $R^{51}$; then converting the azide, nitro, cyano, hydroxyl, oxo, lower alkoxylcarbonyl or aralkyloxycarbonyl group or halogen atom of the compound into amino groups; after, as required, (a) reductive amination with an aldehyde or a ketone represented by the above-cited general formula [V] or (b) carrying out a reaction with a compound represented by the above-cited general formula [V'] in the presence of a base; protecting any amino or imino group; and finally removing imino protective group $P^2$.

Especially, at the step to convert an azide, nitro, cyano, hydroxyl, oxo, lower alkoxycarbonyl or aralkyloxycarbonyl group or halogen atom into an amino group in the above described manufacturing process, if there are two groups to be converted into amino groups in the compound, an intramolecular ring forming reaction will proceed between the amino group generated by that step and a carbon atom, which is attached to the other amino group or a group prior to conversion into the amino group, thereby making it possible to, together with the adjoining one or two of the carbon atoms on the ring, form on the compound a $C_2$–$C_8$ aliphatic nitrogen-containing heterocyclic group containing an imino group, which is substitutable with a lower alkyl group.

The carbon elongation reaction, reduction of any multiple bond, isomerization or oxidative cleavage, and addition or elimination reaction to the multiple bond of water, ammonia, hydrogen halide, carbonyl, hydrogen cyanide or hydrogen azide can be accomplished in the same manners as described above in the manufacturing method 2.

Conversion of an azide, nitro, cyano, hydroxyl, oxo, lower alkoxylcarbonyl or aralkyloxycarbonyl group or halogen atom of the compound into amino groups can be achieved in the same manner as described above in the manufacturing method 2.

The reductive amination with an aldehyde or a ketone represented by the general formula [V] and the reaction with any compound represented by the general formula [V'] can be performed in the same manner as described above in the manufacturing method 1.

The introduction or removal of any protective group for an amino, imino, hydroxyl or oxo group can be carried out in the same manner as described above in the manufacturing method 1.

Any compound represented by the general formula [VI] can be produced, for instance, by removing the imino protective group $P^2$ of a compound represented by the general formula [XI], or a compound obtained by subjecting the compound of the formula [XI] to a carbon elongation reaction, reduction of any multiple bond, isomerization or oxidative cleavage, and addition or elimination reaction to the multiple bond of water, ammonia, hydrogen halide, carbonyl, hydrogen cyanide or hydrogen azide.

To add, compounds represented by the general formula [XI] are either commercially available or can be produced by appropriately combining, as required, known methods or methods similar thereto.

Any compound represented by the general formula [IV-a]

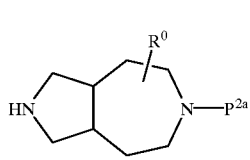

[IV-a]

[wherein $P^{2a}$ means a protective group for an imino group; and $R^0$ means a hydrogen atom or a lower alkyl group] is an essential intermediate for manufacturing compounds represented by the general formula [I], and is a novel compound referred to in no literature.

The present invention also relates to any compound represented by the general formula [IV-a].

In the general formula [IV-a], $P^{2a}$ means an imino group-protective group, an example of which is the aforementioned imino group-protective group.

The imino group-protective group should preferably permit catalytic reduction or deprotection under an acidic condition, and its more specific preferred examples include an aralkyl group, such as a benzyl, p-methoxybenzyl, p-nitrobenzyl, benzhydryl or trityl group; a lower alkoxy carbonyl group, such as a methoxycarbonyl, ethoxycarbonyl group, isobutoxycarbonyl or t-butoxycarbonyl group, an alkekenyloxycarbonyl group, such as a 2-propenyloxycarbonyl group, an aralkyloxycarbonyl group, such as a benzyloxycarbonyl group, p-methoxybenzyloxycarbonyl group or p-nitrobenzyloxycarbonyl group, and a lower alkylsilyl group, such a trimethylsilyl or t-butyldimethylsilyl group, of which more preferable ones include benzyl, t-butoxycarbonyl and benzyloxycarbonyl groups.

$R^0$ means a hydrogen atom or a lower alkyl group, and when $R^0$ is a lower alkyl group, the lower alkyl group can be substituted in any substitutable position on the perhydroazepine ring.

Preferable examples of lower alkyl group for $R^0$ include a methyl group.

Preferable examples of $R^0$ include a hydrgen atom.

Preferable examples of compound represented by the general formula [IV-a] include compounds having a configuration represented by the general formula [IV-a']

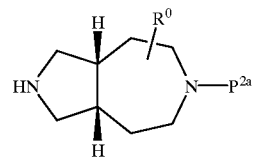

[IV-a']

[wherein $P^{2a}$ and $R^0$ mean respectively the same as the foregoing].

Compounds represented by the general formula [IV-a] are included in the compounds represented by the general formula [IV] cited above. Therefore, any desired compound represented by the general formula [I] can be produced by reacting one of the compounds represented by the general formula [IV-a] with a compound represented by the general formula [III] or a reactive derivative thereof by the manufacturing process 1 described above.

Further, whereas compounds represented by the general formula [IV-a] can be produced by the manufacturing process for compounds represented by the general formula [IV] stated above, the manufacturing process for these compounds is described below in more detail.

By converting the hydroxyl groups of a compound represented by the general formula [XI-a]

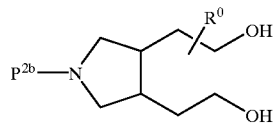

[XI-a]

[wherein $P^{2b}$ means an imino group-protective group, and $R^0$ means the same as the foregoing] into leaving groups, reacting the resultant compound with a compound represented by the general formula [XII]

$H_2N$—$P^{2ap}$ [XII]

[wherein $P^{2ap}$ means a hydrogen atom or a group which, out of an imino group-protective group, does not obstruct the progress of this reaction] into a compound represented by the general formula [XIII]

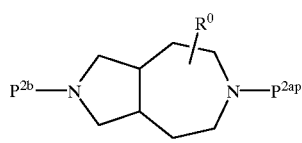

[where P$^{2ap}$, P$^{2b}$ and R$^0$ means respectively the same as the foregoing] and, after converting, where P$^{2ap}$ of the compound is a hydrogen atom, the hydrogen atom into an imino group-protective group represented by P$^{2a}$, removing an imino group-protective group represented by P$^{2b}$, a compound represented by the general formula [IV-a] can be produced.

The step to convert hydroxyl groups into leaving groups in the foregoing reaction can be usually accomplished by using 2 to excessive mols, more preferably 2 to 5 mols, of a sulfonating agent such as methanesulfonyl chloride and a base such as triethylamine, or 2 to excessive mols, more preferably 2 to 5 mols, of a halogenating agent such as thionyl chloride or phosphorus tribromide, upon 1 mol of a compound represented by the general formula [XI-a] in an inactive solvent such as methylene chloride, chloroform, benzene, tetrahydrofuran or ethyl acetate.

The reaction temperature is usually −70° C. to the boiling point of the solvent used in the reaction, more preferably −20° C. to 80° C., and the reaction time is usually 5 minutes to 48 hours, more preferably 30 minutes to 24 hours.

The step in the reaction of a compound represented by the general formula [XII] with the compound after the introduction of leaving groups, obtained by the foregoing reaction, can be usually accomplished by using 1 to excessive mols, more preferably 1 to 50 mols, of the compound [XII] per mol of the starting compound having leaving groups in an inactive solvent such as methylene chloride, chloroform, benzene, ethyl ether or tetrahydrofuran.

Further, this reaction can as well be carried out, as required, in the presence of some other base than that for compounds represented by the general formula [XII].

Examples of such alternative base include inorganic bases such as sodium hydroxide, potassium hydroxide, calcium hydroxide, sodium carbonate, potassium carbonate and sodium hydrogencarbonate, and organic bases such as triethylamine, N-ethyidiisopropylamine, pyridine and N,N-dimethylaniline.

The amount of the base can usually be 2 mol to excessive mols, preferably from 2 to 5 mols per mol of the starting compound.

The reaction temperature is usually −50° C. to 150° C., more preferably −20° C. to 100° C., and the duration of the reaction is usually 5 minutes to 7 days, more preferably 10 minutes to 24 hours.

Where P$^{2ap}$ is a hydrogen atom, the step to convert the hydrogen atom into an imino group-protective group represented by P$^{2a}$ can be accomplished in the same manner as the introduction of the amino group-protective group described earlier in the manufacturing process 1.

Removal of any imino group-protective group represented by P$^{2b}$ usually should be accomplished selectively, to distinguish from any imino group-protective group represented by P$^{2a}$. Therefore, where an imino group-protective group represented by P$^{2b}$ is to be removed by catalytic reduction, what is represented by P$^{2b}$ should preferably be an imino group-protective group that can be readily removed by catalytic reduction, such as an aralkyl or aralkyloxycarbonyl group as mentioned above and, on the other hand, P$^{2a}$ should preferably an imino group-protective group that can be readily removed under an acid condition, such as a lower alkoxycarbonyl, alkenyloxycarbonyl or lower alkylsilyl group as mentioned above. To the contrary, where an imino group-protective group represented by P$^{2b}$ is to be removed under an acid condition, what is represented by p$^{2b}$ should preferably be an imino group-protective group that can be readily removed under an acid condition, such as a lower alkoxycarbonyl, alkenyloxycarbonyl or lower alkylsilyl group as mentioned above and, on the other hand, P$^{2a}$ should preferably an imino group-protective group that can be readily removed by catalytic reduction, such as an aralkyl or aralkyloxycarbonyl group as mentioned above.

To add, compounds represented by the general formulas [XI-a] and [XII] are either commercially available or can be produced by appropriately combining, as required, known methods or methods similar thereto.

The utility of compounds of the present invention is demonstrated by tests on inhibition of binding to muscarinic receptors and on antagonism to various muscarinic receptors.

Tests on Inhibition of Binding to Muscarinic Receptors

These tests were performed according to a modification of the method of Hargreaves et al. (Br. J. Pharmacol. 107: pp. 494–501, 1992). Thus, CHO cells expressing m2 and m3 muscarinic acetylcholine receptors (Receptor Biology Inc.) were incubated with 0.2 nM [$^3$H]-N-methylscopolamine (84Ci/mmol, New England Nuclear, Inc.) and each compound of the present invention to be tested in 0.5 ml of 50 mM tris-HCl—10 mM MgCl$_2$—1 mM EDTA (pH 7.4) for 120 minutes at room temperature (about 20 to 25° C.), followed by suction filtration with a glass filter (Uni-Filter plate GF/C; Packard Instruments Co., Ind.) and washing four times with 1 ml of ice-cold Tris-HCl buffer. After the filter was dried for 1 hour at 50° C., a scintillator (Miroscinti 0; Packard Instruments Co., Inc.) was added, and the radioactivity of [$^3$H]-N-methylscopolamine adsorbed by the filter was counted by a liquid scintillation counter (TopCount™; Packard Instruments Co., Inc.). Non-specific binding of [$^3$H]-N-methylscopolamine was measured in the presence of 1 μM N-methylscopolamine, which was added. According to the method of Cheng and Prusoff (Biochem. Pharmacol. 22: pp. 3099–3108, 1973), the binding affinity (K$_i$ value) of the compound of the present invention for muscarinic receptors was calculated from the concentration (IC$_{50}$) of the test compound which achieved 50% inhibition of the binding of [$^3$H]-N-methylscopolamine, labeled ligand.

TABLE 1

Inhibitory Effects on Binding to Muscarinic m2 and m3 Receptors

| | K$_i$ (nM) | | |
| --- | --- | --- | --- |
| | m2 | m3 | m2/m3 |
| Compound of Example 13 | 630 | 3.7 | 170 |
| Compound of Example 26 | 27 | 0.44 | 60 |
| Compound of Example 29 | 230 | 1.2 | 190 |
| Compound of Example 35 | 670 | 4.2 | 160 |
| Compound of Example 43 ((IS*)-substance) | 21 | 0.26 | 80 |

As is clear from the results shown in Table 1 above, those compounds of the present invention exhibited far greater binding-inhibitory activity to the m3 receptor than to the m2 receptor.

Tests on Antagonism to Muscarinic Receptors (in vitro)

1) Tests for Antagonism to $M_2$ Receptor in an Isolated Rat Right Atrium

These tests were performed according to a conventional method. A male SD strain rat (weighing 300–500 g) was killed by exsanguination, and the right atrium was isolated. This preparation was isometrically suspended in organ bath filled with 20 ml of Krebs-Hanseleit solution (gassed with 95% $O_2$-5% $CO_2$ and kept at 32° C.) with an initial tension of 0.5 g. The heart rate was recorded with a heart rate counter. After the preparation was equilibrated for 30 minutes, carbachol ($10^{-9}$ to $10^{-6}$ M) was cumulatively administered in three-fold increasing doses. Thus, a decrease in heart rate was measured to obtain a dose-response curve for the control experiment. After the preparation was washed with fresh solution to restore the heart rate, a test compound was administered thereto. Ten minutes later, carbachol was cumulatively administered again. Responses to carbachol were expressed as percentages based on the heart rate before the administration of carbachol as 100%. The antagonistic potency ($K_B$ value) of the test compound was determined from the degree of shift of the dose-response curve obtained by treatment with individual test compound of the present invention.

2) Tests for Antagonism to the Airway $M_3$ Receptor in an Isolated Rat Right Trachea These tests were performed according to a conventional method. A male SD strain rat (weighing 300–500 g) was killed by exsanguination, and the trachea was isolated. Annular segments (2 mm wide) were cut out from the trachea and cut transversely at the anterior cartilage part to make an open ring preparation. The preparation was suspended in a Magnus tube filled with 5 ml of Krebs-Hanseleit solution (gassed with 95% $O_2$-5% $CO_2$ and kept at 32° C.) with an initial tension of 1.0 g and a resting tension of 0.6 g. The tension of the preparation was recorded isometrically. After the preparation was equilibrated for an hour, the preparation was caused to contract twice with $10^{-4}$ M carbachol, and the second contraction induced by carbachol was used as the reference contraction. After the preparation was washed with fresh solution to be restored to the base line, a test compound was administered thereto (or no treatment was given). Ten minutes later, carbachol ($10^{-8}$ to $10^{-3}$ M) was cumulatively administered in three-fold increasing doses to obtain a dose-response curve. The dose-response curve was plotted by expressing responses as percentages based on the reference contraction of the preparation as 100%. The antagonistic potency ($K_B$ value) of the test compound was determined from the degree of shift of the dose-response curve obtained by treatment with the test compound.

TABLE 2

Antagonism to Muscarinic Receptors (in vitro)

| | $K_B$ (nM) | | |
|---|---|---|---|
| | Right atrium $M_2$ | Trachea $M_3$ | $M_2/M_3$ |
| Compound of Example 1 | 730 | 20 | 37 |
| Compound of Example 26 | 75 | 0.83 | 75 |
| Compound of Example 29 | 230 | 1.6 | 140 |

TABLE 2-continued

Antagonism to Muscarinic Receptors (in vitro)

| | $K_B$ (nM) | | |
|---|---|---|---|
| | Right atrium $M_2$ | Trachea $M_3$ | $M_2/M_3$ |
| Compound of Example 35 | 2400 | 8.0 | 300 |

As is evident from the results indicated in Table 2 above, the compounds of the present invention exhibited far stronger antagonism to the trachea $M_3$ receptor than to the right atrium $M_2$ receptor. Therefore, the compounds of the present invention are more selective for the trachea $M_3$ receptor.

Tests for Antagonism Against Muscarinic $M_3$ Receptor (in vivo)

Tests for Bronchodilation in Dogs (oral administration)

Male beagles of 12 to 24 months of age, weight 10 to 15 kg, were anesthetized with pentobarbital (30 mg/kg, iv.), and the trachea of each dog was intubated. The sensitivity of the airway (methacoline reaction threshold value) was measured at least twice at two weeks' intervals by a methacoline provocation test, and dogs manifesting a reproducible methacoline reaction threshold value[1] were selected. To those dogs whose methacholine reaction threshold value was established, the test compound was orally administered (0.1 mg/kg). Four hours after the administration, a methacoline provocation test was again conducted, and the methacholine reaction threshold value[2] after the administration of the test compound was measured. The brochodilator activity of the test compound was determined by the following equation:

$$\text{Shift value} = \frac{\text{methacholine reaction threshold value}^{2)} \text{ after drug administration}}{\text{methacoline reaction threshold value}^{1)} \text{ without drug administration}}$$

The methacholine provocation test was conducted using an Astograph TCK-6100H model (Chest). Methacholine chloride was used as brochoconstritor, which was diluted with isotonic sodium chloride solution in 10 grade concentration levels from 40,000 μg/ml to 20,000, 10,000, 5,000, 2,500, 1,250, 625, 312.5, 156 and 78 μg/ml. The test animals were caused to inhale these methacoline aerosols for 1 min. at a time, starting with the lowest concentration upward, and the respiratory resistance was continuously recorded. The concentration of methacoline at which the respiratory resistance reached a value twice its initial level was deemed to be the methacholine threshold value.

TABLE 3

Brochodilation Activity in Dogs (Oral Administration)

| | Methacoline Provocation Test (0.1 mg/Kg, P.O.) Shift value (4 hrs. Later) |
|---|---|
| Compound of Example 26 | 7.1 |
| Compound of Example 29 | 22 |
| Compound of Example 35 | 5.8 |

TABLE 3-continued

Brochodilation Activity in Dogs
(Oral Administration)

Methacoline Provocation Test (0.1 mg/Kg, P.O.)
Shift value (4 hrs. Later)

| | |
|---|---|
| Compound of Example 43 ((IS*)-substance) | 22 |

As clearly demonstrated in Table 3 above, the compounds of the present invention exhibited powerful and highly durable brochodilator actions.

As stated above, the compounds of the formula [I] of the present invention exhibit potent and selective antagonistic activity against muscarinic $M_3$ receptors, and manifest excellent oral activity, duration of action and pharmacokinetics. Hence, they can be administered to patients orally or parenterally as safe pharmaceutics exhibiting little side effects, especially in the treatment and/or prophylaxis of diseases include such respiratory diseases as chronic obstructive pulmonary diseases, chronic bronchitis, asthma, chronic respiratory obstruction, pulmonary fibrosis, pulmonary emphysema and rhinitis; such digestive diseases as irritable bowel syndrome, convulsive colitis, gastric and duodenal ulcers, convulsion or hyperkinesia of digestive canal, diverticulitis and pain accompanying contraction of smooth muscles of the digestive system; urinary diseases entailing dysuria such as urinary incontinence, urinary urgency and pollakiuria in nervous pollakiuria, neurogenic bladder, nocturnal enuresis, unstable bladder, cystospasm or chronic cystisis; and motion sickness.

In practically using the compounds of the present invention for the treatment or prophylaxis of such diseases, they may be combined with pharmaceutically acceptable adjuvants in the usual manner to prepare pharmaceutical compositions suitable for administration. For this purpose, a variety of adjuvants which are commonly used in the pharmaceutics can be applied. Examples of such adjuvants include gelatin, lactose, sucrose, titanium oxide, starch, crystalline cellulose, hydroxypropylmethylcellulose, carboxymethylcellulose, corn starch, microcrystalline wax, white petrolatum, magnesium aluminate metasilicate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinyl pyrrolidone, magnesium stearate, light anhydrous silicic acid, talc, vegetable oil, benzyl alcohol, acacia, propylene glycol, polyalkylene glycol, cyclodextrin and hydroxypropylcyclodextrin.

The dosage forms of pharmaceutical compositions prepared by using these adjuvants include solid preparations such as tablets, capsules, granules, powders and suppositories; and liquid preparations such as syrups, elixirs and injections. These preparations may be formulated according to conventional techniques well known in the field of pharmaceutics. Liquid preparations may be in a form which is dissolved or suspended in water or other suitable medium prior to use. In particular, injections may be in the form of a solution or suspension in physiological saline solution or a glucose solution, or in powder form for reconstitution by dissolution or suspension in physiological saline solution or a glucose solution prior to use. If desired, such injections may contain buffer agents and/or preservatives.

As preparations for oral administration, such formulation forms, besides ordinary tablets, capsules, granules, powders and the like, aerosols or dry powders for inhalation, elixirs containing spices or coloring agents or suspensions may be employed.

In these pharmaceutical compositions, a compound in accordance with the present invention may be present in a ratio of from 1.0 to 100% by weight, preferably 1.0 to 60% by weight, based on the total weight of the composition. These pharmaceutical compositions may additionally contain other therapeutically effective compounds.

When the compounds of the present invention are used as drugs, their dosage level and dosage schedule may vary according to the sex, age and body weight of the patient, the relative severity of symptoms, the type and range of the desired therapeutic effect, and the like. Generally for oral administration, they should preferably be administered in a daily dose of 0.1 to 100 mg/kg for adults, and this daily dose may be given at a time or in several divided doses. For parenteral administration, they should preferably be administered in a daily dose of 0.001 to 10 mg/kg for adults, and this daily dose may be given at a time or in several divided doses.

BEST MODES FOR CARRYING OUT THE INVENTION

Hereinafter the present invention is described more specifically with reference to working examples, it being understood that the examples are in no way limitative of the scope of the invention.

EXAMPLE 1

4-Amino-1-{(2R)-2-((1R)-3,3-difluorocyclopentyl)-2-hydroxy-2-Phenylacetyl}piperidine monohydrochloride Step 1. Synthesis of 1-benzyl-4-t-butoxycarbonylaminopiperidine To a solution of 25 g of 4-amino-1-benzylpiperidine in 150 ml of chloroform, 31.4 g of di-t-butyl dicarbonate was added under cooling with ice, followed by stirring for 2 hours at room temperature. The reaction mixture was diluted over chloroform and washed with water, followed by drying over anhydrous magnesium sulfate. The solvent was distilled off under reduced pressure, and 35.65 g of the title compound was obtained by recrystallizing the resultant residue from hexane/diisopropyl ether.

Step 2. Synthesis of 4-t-butoxycarbonylaminopiperidine

To a solution of 59 g of 1-benzyl-4-t-butoxycarbonylaminopiperidine in a mixture of 550 ml of methanol and 24 ml of acetic acid, 5 g of 10% palladium-carbon catalyst was added, followed by stirring for 20 hours in a hydrogen atmosphere. After filtering the catalyst off, the solvent was concentrated under reduced pressure, followed by dilution with chloroform, washing with sodium hydrogencarbonate-added brine and drying over anhydrous magnesium sulfate. The solvent was distilled off under reduced pressure, and 53.7 g of the title compound obtained by washing the resulting residue with diisopropyl ether.

Step 3. Synthesis of 4-t-butoxycarbonylamino-1-{(2R)-2—((1R)-3,3-difluorocyclopentyl)-2-hydroxy-2-phenylacetyl}piperidine To a solution of 220 mg of 4-t-butoxycarbonylaminopiperidine and 256 mg of (2R)-2-((1R)-3, 3-difluorocyclopentyl)-2-hydroxy-2-phenylacetic acid in 8 ml of chloroform, 203 mg of 1-hydroxybenzotriazole and 201 mg of 1-ethyl-3-(3-dimethylaminopropyl)carbodiimide were added sequentially at room temperature, followed by stirring for 3 hours at the same temperature. The reaction mixture was diluted with ethyl acetate and, after sequential washing with an aqueous solution of 1N sodium hydroxide and brine, dried over anhydrous sodium sulfate. The solvent was distilled off under reduced pressure, and 314 mg of the title compound was obtained by purifying the resultant residue by silica gel column chromatography (eluting solvent: hexane/ethyl acetate=2/1).

Step 4. Synthesis of 4-amino-1-{(2R)-2-((1R)-3,3-difluorocyclopentyl)-2-hydroxy-2-phenylacetyl}piperidine monohydrochloride In 2 ml of 10% HCl-methanol, 84 mg of 4-t-butoxycarbonylamino-1-{(2R)-2-((1R)-3,3-difluorocyclopentyl)-2-hydroxy-2-phenylacetyl}piperidine was dissolved, and stirred for 3 hours at room temperature. The solvent was distilled off under reduced pressure, and 60 mg of the title compound was obtained as a colorless solid by recrystallizing the resulting residue from ethyl acetate/hexane.

$^1$H-NMR (CD$_3$OD, δ ppm): 1.15–2.10(12H, m), 2.50–2.70(1H, m), 2.75–3.00(1H, m), 3.00–3.10(1H, m), 3.10–3.24(1H, m), 7.25–7.45(5H, m); Low resolution FAB-MS (m/e, C$_{18}$H$_{24}$F$_2$N$_2$O$_2$+H)$^+$: 339.

EXAMPLE 2

4-Amino-1-((2R)-2-cyclopentyl-2-hydroxy-2-phenylacetyl)piperidine monohydrochloride The title compound was prepared by procedures similar to those for Example 1 using (2R)-2-cyclopentyl-2-hydroxy-2-phenylacetic acid, and obtained as a colorless solid.

$^1$H-NMR (CD$_3$OD, δ ppm): 1.20–1.60(10H, m), 1.75–1.93 (2H, m), 2.50–2.67(1H, m), 2.78–2.95 (3H, m), 3.12–3.25(2H, m), 7.21–7.45(5H, m); Low resolution FAB-MS (m/e, C$_{18}$H$_{26}$N$_2$O$_2$+H)$^+$: 303.

EXAMPLE 3

4-Amino-1-{(2R)-2-((1R)-3,3-difluorocyclopentyl)-2-hydroxy-2-phenylacetyl}-4-methylpiperidine Step 1. Synthesis of ethyl N-t-butoxycarbonylisonipecotate The title compound was prepared by a method similar to Step 1 for Example 1, using ethyl isonipecotate.

Step 2. Synthesis of ethyl N-t-butoxycarbonyl-4-methylpiperidine-4-carboxylate

To a solution of 5.0 g of ethyl N-t-butoxycarbonylisonipecotate in a mixture of 100 ml of tetrahydrofuran and 7.4 ml of hexamethylphosphoric triamide, 15.5 ml of a 1.5 M lithium diisopropylamide/cyclohexane was added dropwise at −78° C., and the mixture was stirred for 1 hour, after the temperature being raised to −40° C. The reaction mixture was cooled to −78° C. and, with 3.6 ml of methyl iodide being added dropwise to it, stirred for 1 hour while being raised to room temperature. The reaction mixture was diluted with ethyl acetate and, after sequential washing with a saturated aqueous solution of ammonium chloride, water and brine, dried over anhydrous magnesium sulfate. The solvent was distilled off under reduced pressure, and 4.0 g of the title compound was obtained by purifying the resulting residue by silica gel column chromatography (eluting solvent: hexane~hexane/ethyl acetate=17/1).

Step 3. Synthesis of N-t-butoxycarbonyl-4-methylpiperidine-4-carboxylic acid

To a 75% aqueous methanol solution of 1.5 g of ethyl N-t-butoxycarbonyl-4-methylpiperidine-4-carboxylate, 5 ml of a 6N aqueous solution of potassium hydroxide was added, followed by reflux under heating for 1 hour. The reaction mixture was cooled to room temperature, adjusted its pH to 4 with 2N hydrochloric acid, and extracted with chloroform, followed by drying over anhydrous magnesium sulfate. Distillation of the solvent under reduced pressure gave 1.3 g of the title compound.

Step 4. Synthesis of 4-benzyloxycarbonylamino-1-t-butoxylcarbonyl-4-methylpiperidine To a solution of 700 mg of N-t-butoxycarbonyl-4-methylpiperidine-4-carboxylic acid in 14 ml of toluene, 0.60 ml of triethylamine and 0.93 ml of diphenylphosphorylazide were added, followed by reflux under heating for 1.5 hours. To the reaction mixture, 0.45 ml of benzylalcohol was added, and the resultant mixture was further refluxed for 27 hours. After being cooled to room temperature, the reaction mixture was diluted with ethyl acetate and, after sequential washing with an aqueous solution of sodium hydrogencarbonate and brine, dried over anhydrous magnesium sulfate. The solvent was distilled off under reduced pressure, and 1.0 g of the crude title compound was obtained by purifying the resulting residue by silica gel column chromatography (eluting solvent: hexane/ethyl acetate=10/1~7/1).

Step 5. Synthesis of 4-benzyloxycarbonylamino-4-methylpiperidine

In 20 ml of 10% HCl-methanol, 1.0 g of 4-benzyloxycarbonylamino-1-t-butoxylcarbonyl-4-methylpiperidine was dissolved, followed by stirring for 12 hours at room temperature. The solvent was distilled off under reduced pressure, and the resulting residue, to which water was added, washed with diethyl ether. After basifying with 4M sodium hydroxide, the aqueous layer was extracted with chloroform, and dried over anhydrous magnesium sulfate. Distilling off the solvent under reduced pressure gave 463 mg of the title compound.

Step 6. Synthesis of 4-benzyloxycarbonylamino-1-{(2R)-2-((1R)-3,3-difluorocyclopentyl)-2-hydroxy-2-phenylacetyl}-4-methylpiperidine The title compound was prepared by a method similar to Step 3 for Example 1, using 4-benzyloxycarbonylamino-4-methylpiperidine.

Step 7. Synthesis of 4-amino-1-{(2R)-2-((1R)-3,3-difluorocyclopentyl)-2-hydroxy-2-phenylacetyl}-4-methylpiperidine To a solution of 568 mg of 4-benzyloxycarbonylamino-1-{(2R)-2-((1R)-3,3-difluorocyclopentyl)-2-hydroxy-2-phenylacetyl}-4-methylpiperidine in a mixture of 10 ml of methanol and 5 ml of ethyl acetate, 200 mg of 10% palladium-carbon catalyst was added, followed by stirring for 18 hours under a hydrogen atmosphere. After filtering the catalyst off, the solvent was distilled off under reduced pressure, and the resulting residue was dissolved in 1M hydrochloric acid and washed with diethyl ether. After basifying with 4N sodium hydroxide, the aqueous layer was extracted with chloroform, and dried over anhydrous magnesium sulfate to give 320 mg of the title compound as a colorless oily substance.

$^1$H-NMR (CDCl$_3$, δ ppm): 1.03 (3H, s), 0.89–1.90 (6H, m), 1.95–2.45(6H, m), 3.10–3.25(1H, m), 3.30–3.59 (2H, m), 7.21–7.42(5H, m); Low resolution FAB-MS (m/e, (C$_{19}$H$_{26}$F$_2$N$_2$O$_2$+H)$^+$: 353.

Alternative Method

Alternative Step 1. Synthesis of 1-t-butoxycarbonyl-4-piperidone

To a solution of 25 g of 4-piperidone monochloride monohydrate in 500 ml of chloroform, 38.5 ml of triethylamine and 36.2 g of di-t-butyl dicarbonate were added sequentially under cooling with ice, followed by stirring for 2 hours at room temperature. The reaction mixture was diluted with ethyl acetate and, after washing with 0.1 N hydrochloric acid, dried over anhydrous sodium sulfate. Distilling off the solvent under reduced pressure gave 31.4 g of the title compound.

Alternative Step 2. Synthesis of 1-t-butoxycarbonyl-4-methylidenepiperidine

To a solution of 2.66 g of methyltriphenylphosphonium bromide in 20 ml of tetrahydrofuran, 1.7 ml of 1.63 M n-butyllithium/hexane was added dropwise under cooling with ice, followed by stirring for 1 hour at room temperature. A solution of 482 mg of 1-t-butoxycarbonyl-4-piperidone in 5 ml of tetrahydrofuran was added dropwise to the mixture, again under cooling with ice, followed by stirring for 1 hour at room temperature. The reaction mixture was diluted with ethyl acetate, washed sequentially with water and brine, and dried over anhydrous sodium sulfate. The solvent was distilled off under reduced pressure, and 445 mg of the title compound was obtained by purifying the resulting residue by silica gel chromatography (eluting solvent: hexane~hexane/ethyl acetate=5/1).

Alternative Step 3. Synthesis of 4-azido-1-t-butoxycarbonyl-4-methylpiperidine

To 10 ml of a 50% tetrahydrofuran aqueous solution of 250 mg of mercury acetate, 150 mg of sodium azide and 139 mg of 1-t-butoxycarbonyl-4-methylidenepiperidine were added, followed by stirring for 17 hours under heating at 90° C. After cooling to room temperature, 0.1 ml of a 15% potassium hydroxide aqueous solution, and further a suspension of 20 mg of sodium borohydride in 0.1 ml of a 15% potassium hydroxide aqueous solution, were added, followed by stirring for 30 minutes at room temperature. The reaction mixture was diluted with diethyl ether, washed sequentially with water and brine, and dried over anhydrous sodium sulfate, followed by distilling off the solvent under reduced pressure to give 165 mg of the title compound.

Alternative Step 4. Synthesis of 4-azido-4-methylpiperidine

To a solution of 19 mg of 4-azido-1-t-butoxycarbonyl-4-methylpiperidine in 1 ml of chloroform, 0.5 ml of trifluoroacetic acid was added, followed by stirring for 30 minutes at room temperature. Distilling off the solvent under reduced pressure gave 20 mg of the title compound.

Alternative Step 5. Synthesis of 4-azido-1-{(2R)-2-((1R)-3,3-difluorocyclopentyl)-2-hydroxy-2-phenylacetyl}-4-methylpiperidine The title compound was prepared by a method similar to Step 3 for Example 1, using 4-azido-4-methylpiperidine.

Alternative Step 6. Synthesis of 4-amino-1-{(2R)-2-((1R)-3,3-difluorocyclopentyl)-2-hydroxy-2-phenylacetyl}-4-methylpiperidine To a solution of 18 mg of 4-azido-1-{(2R)-2-((1R)-3,3-difluorocyclopentyl)-2-hydroxy-2-phenylacetyl}-4-methylpiperidine in 2 ml of methanol, 5 mg of 10% palladium-carbon catalyst was added, followed by stirring for 2 hours in a hydrogen atmosphere. After filtering the catalyst off, the solvent was distilled off under reduced pressure, and the resulting residue was purified by preparative thin-layer chromatography [Kieselgel™ 60F$_{254}$, Art 5744 (Merck); chloroform/methanol=10/1] to provide 16 mg of the title compound.

EXAMPLE 4

4-Amino-1-((2R)-2-cyclopentyl-2-hydroxy-2-phenylacetyl)-4-methylpineridine

The title compound was prepared by procedures similar to those for Example 3 using (2R)-2-cyclopentyl-2-hydroxy-2-phenylacetic acid, and was obtained as a colorless oily substance.

$^1$H-NMR (CDCl$_3$, δ ppm): 0.74–1.90(12H, m), 1.03 (3H, s), 2. 81–2. 99(1H, m), 3.20–3.79(4H, m), 5.20–5.48 (1H, br), 7.10–7.45(5H, m); Low resolution FAB-MS (m/e, (C$_{19}$H$_{28}$N$_2$O$_2$+H)$^+$: 317.

EXAMPLE 5

4-Amino-1-{(2R)-2-((1R)-3,3-difluorocyclopentyl)-2-hydroxy-2-phenylacetyl}4-ethylpiperidine The title compound was prepared by procedures similar to those for Example 3 using ethyl iodide, and was obtained as a colorless oily substance.

$^1$H-NMR (CDCl$_3$, δ ppm): 0.65–1.85(11H, m), 1.95–2.50 (4H, m), 3.10–3.90(5H, m), 7.25–7.40(5H, m); Low resolution FAB-MS (m/e, (C$_{20}$H$_{26}$F$_2$N$_2$O$_2$+H)$^+$: 367.

EXAMPLE 6

4-Amino-1-((2R)-2-cyclopentyl-2-hydroxy-2-phenylacetyl)-4-ethylpiperidine

The title compound was prepared by procedures similar to those for Example 5 using (2R)-2-cyclopentyl-2-hydroxy-2-phenylacetic acid, and was obtained as a colorless oily substance.

$^1$H-NMR (CDCl$_3$, δ ppm): 0.83(3H, t, J=7.0 Hz), 1.20–2.00(14H, m), 2.80–2.95(1H, m), 3.30–3.80(4H, m), 7.20–7.43(5H, m); Low resolution FAB-MS (m/e, (C$_{20}$H$_{30}$N$_2$O$_2$+H)$^+$: 331.

EXAMPLE 7

4-Aminomethyl-1-{(2R)-2-((1R)-3,3-difluorocyclopentyl)-2-hydroxy-2-phenylacetyl}piperidine The title compound was prepared by procedures similar to Steps 5 to 7 for Example 3 using 1-t-butoxycarbonyl-4-azidomethylpiperidine, and was obtained as a colorless foamy substance.

$^1$H-NMR (CDCl$_3$, δ ppm): 0.71–0.98(2H, m), 1.31–1.52 (2H, m), 1.52–1.68(2H, m), 1.68–1.86(4H, m), 1.98–2.49 (5H, m), 2.49–2.75(2H, m)3.09–3.25(1H, m), 7.20–7.41 (5H, m); Low resolution FAB-MS (m/e, (C$_{19}$H$_{26}$F$_2$N$_2$O$_2$+H)$^+$: 353.

EXAMPLE 8

4-Aminomethyl-1-((2R)-2-cyclopentyl-2-hydroxy-2-phenylacetyl)piperidine

The title compound was prepared by procedures similar to those for Example 7 using (2R)-2-cyclopentyl-2-hydroxy-2-phenylacetic acid, and was obtained as a colorless oily substance.

$^1$H-NMR (CDCl$_3$, δ ppm): 0.90–0.97(1H, m), 1.21–2.08 (14H, m), 2.40–2.85(4H, m), 2.85–3.04(1H, m), 4.00–4.62 (2H, br), 7.18–7.45(5H, m); Low resolution FAB-MS (m/e, (C$_{19}$H$_{28}$N$_2$O$_2$+H)$^+$: 317.

EXAMPLE 9

4-Aminomethyl-1-{(2R)-2-((1R)-3,3-difluorocyclopentyl)-2-hydroxy-2-phenylacetyl}-4-methylpiperidine Step 1. Synthesis of N-t-butoxycarbonyl-4-methylpiperidine-4-methanol To a solution of 527 mg of ethyl N-t-butoxycarbonyl-4-methylpiperidine-4-carboxylate in 5 ml of tetrahydrofuran, 90 mg of lithium aluminiumhydride was added under cooling with ice, followed by stirring for 1 hour at the same temperature. Sodium sulfate decahydrate was added to the reaction mixture, which was stirred for 1 hour and filtered with Celite. Distilling off the solvent under reduced pressure gave the title compound.

Step 2. Synthesis of N-t-butoxycarbonyl-4-methylpiperidine-4-carbaldehyde

To a solution of 0.4 ml of dimethyl sulfoxide in 5 ml of chloroform, oxalyl chloride was added dropwise at −60° C., followed by stirring for 5 minutes at the same temperature. To the reaction mixture, the solution of N-t-butoxycarbonyl-4-methylpiperidine-4-methanol, obtained by Step 1, in 1 ml of chloroform was added dropwise and, after stirring for 20 minutes at the same temperature, 2 ml of triethylamine was added, followed by stirring for 0.5 hour while heating the mixture to room temperature. The reaction mixture was diluted with ethyl acetate, washed sequentially with water and brine, and dried over anhydrous sodium sulfate. The solvent was distilled off under reduced pressure, and the resulting residue was purified by silica gel chromatography (eluting solvent: hexane/ethyl acetate=4/1) to give 367 mg of the title compound.

Step 3. Synthesis of 4-aminomethyl-1-t-butoxycarbonyl-4-methylpiperidine

To a solution of 367 mg of N-t-butoxycarbonyl-4-methylpiperidine-4-carbaldehyde in 5 ml of methanol, 1.2 g of ammonium acetate and 130 mg of sodium cyanoborohydride, followed by stirring for 1 hour at room temperature. The reaction mixture was diluted with chloroform, washed sequentially with a 3N sodium hydroxide aqueous solution and brine, and dried over anhydrous sodium sulfate. The solvent was distilled off under reduced pressure to give the title compound.

Step 4. Synthesis of 4-benzyloxycarbonylaminomethyl-1-t-butoxycarbonyl-4-methylpiperidine To 6 ml of a tetrahydrofuran solution of 4-aminomethyl-1-t-butoxycarbonyl-4-methylpiperidine, obtained by Step 3, 1 ml of diisopropylehtylamine and 0.3 ml of benzyloxycarbonyl chloride were added successively, followed by stirring for 1 hour at the same temperature. The reaction mixture was diluted with ethyl acetate, washed successively with water and brine, and dried over anhydrous sodium sulfate. The solvent was distilled off under reduced pressure, and 324 mg of the crude title compound was obtained by purifying the resulting residue by silica gel column chromatography (eluting solvent: hexane/ethyl acetate=5/1~2/1).

Step 5. Synthesis of 4-benzyloxycarbonylaminomethyl-4-methylpiperidine

To a solution of 30 mg of 4-benzyloxycarbonylaminomethyl-1-t-butoxycarbonyl-4-methylpiperidine in 2 ml of chloroform, 1 ml of trifluoroacetic acid was added at room temperature, followed by stirring for 0.5 hour at the same temperature. The solvent was distilled off under reduced pressure, and azeotropically distilled with a mixture of chloroform and toluene to give the title compound.

Step 6. Synthesis of 4-benzyloxycarbonylaminomethyl-1-{(2R)-2-((1R)-3,3-difluorocyclopentyl)-2-hydroxy-2-phenylacetyl}-4-methylpiperidine The title compound was prepared by a method similar to Step 3 for Example 1, using 4-benzyloxycarbonylaminomethyl-4-methylpiperidine.

Step 7. Synthesis of 4-aminomethyl-1-{(2R)-2-((1R)-3,3-difluorocyclopentyl)-2-hydroxy-2-phenylacetyl}-4-methylpiperidine To a solution of 16 mg of 4-benzyloxycarbonylaminomethyl-1-{(2R)-2-((1R)-3,3-difluorocyclopentyl)-2-hydroxy-2-phenylacetyl}-4-methylpiperidine in 2 ml of methanol, 4 mg of 10% palladium-carbon catalyst was added, followed by stirring, for 4 hours under a hydrogen atmosphere. After filtering the catalyst off, the solvent was distilled off under reduced pressure, and the resulting residue was dissolved in 1M hydrochloric acid and washed with diethyl ether. After basifying with 3N sodium hydroxide, the aqueous layer was extracted with chloroform. The organic layer was then dried over anhydrous sodium sulfate, and the solvent was distilled off under reduced pressure to give 3.5 mg of the title compound as a colorless oily substance.

$^1$H-NMR (CDCl$_3$, δ ppm): 0.50–1.40(4H, m), 0.83(3H, s), 1.65–2.50(10H, m), 2.90–3.30 (3H, m), 3.50–4.00 (2H, br), 7.15–7.50(5H, m); Low resolution FAB-MS (m/e, (C$_{20}$H$_{28}$F$_2$N$_2$O$_2$+H)$^+$: 367.

EXAMPLE 10

4-Aminomethyl-1-{(2R)-2-((1R)-3,3-difluorocyclopentyl)-2-hydroxy-2-phenylacetyl{-4-ethylpiperidine Step 1. Synthesis of 1-benzyl-4-ethylpiperidine-4-carbonitrile The title compound was prepared by a method similar to Step 2 for Example 3, using 1-benzylpiperidine-4-carbonitrile and ethyl iodide.

Step 2. Synthesis of 1-benzyl-4-t-butoxycarbonylaminomethyl-4-ethylpiperidine

To a solution of 100 mg of 1-benzyl-4-ethylpiperidine-4-carbonitrile in 2 ml of tetrahydrofuran, 38 mg of lithium aluminumhydride was added under cooling with ice, followed by reflux for 1 hour under heating. The reaction mixture was cooled with ice, to which sodium sulfate decahydrate was added, and filtered with Celite after stirring for 1 hour. The residue obtained by distilling off the solvent under reduced pressure was suspended in a mixture of 5 ml of 0.5 M sodium hydroxide aqueous solution and 5 ml of dioxane, to which 110 mg of dibutyldicarbonate was added, followed by stirring overnight. The reaction mixture was diluted with ethyl acetate and, after washing with brine, dried over anhydrous sodium sulfate. The solvent was distilled off under reduced pressure, and the resulting residue was purified by preparative thin-layer chromatography [Kieselgel™60F$_{254}$, Art 5744 (Merck); chloroform/methanol=20/1]to provide 34 mg of the title compound.

Step 3. Synthesis of 4-t-butoxycarbonylaminomethyl-4-ethylpiperidine

To a solution of 29 mg of 1-benzyl-4-t-butoxycarbonylaminomethyl-4-ethylpiperidine in 2 ml of ethanol, 5 mg of palladium-carbon catalyst was added, followed by stirring for 3 hours under a hydrogen atmosphere. After the catalyst was filtered off, the solvent was distilled under reduced pressure to give the title compound.

Step 4. Synthesis of 4-aminomethyl-1-{(2R)-2-((1R)-3,3-difluorocyclopentyl)-2-hydroxy-2-phenylacetyl}-4-ethylpiperidine The title compound was prepared by a method similar to Steps 3 and 4 for Example 1, using 4-t-butoxycarbonylaminomethyl-4-ethylpiperidine, and obtained as a colorless oily substance.

$^1$H-NMR (CDCl$_3$, δ ppm): 0.72(3H, t, J=7.5 Hz), 0.80–1.50(8H, m), 1.50–2.40 (6H, m), 2.56(2H, s), 2.80–3.80(5H, m), 7.20–7.40(5H, m); Low resolution FAB-MS (m/e, (C$_{21}$H$_{30}$F$_2$N$_2$O$_2$+H)$^+$: 381.

EXAMPLE 11

4-(1-Aminoethyl)1-(2R)-2-((1R)-3,3-difluorocyclopentyl)-2-hydroxy-2-phenylacetyl}piperidine Step 1. Synthesis of N-t-butoxycarbonylisonipecotic acid In 50 ml of 90% methanol aqueous solution, 1.0 g of ethyl N-t-butoxycarbonylisonipecotate was dissolved, and 2 ml of 2N sodium hydroxide aqueous solution was added thereto, followed by reflux for 1.5 hours under heating. The reaction mixture, after cooling to room temperature, was extracted with chloroform, and dried over anhydrous magnesium sulfate. Distilling the solvent off under reduced pressure gave 873 mg of the title compound.

Step 2. Synthesis of N-methoxy-N-methyl-1-t-butoxycarbonylisonipecotamide

The title compound was prepared by a method similar to Step 6 for Example 3, using N-t-butoxycarbonylisonipecotinic acid and N,O-dimethylhydroxylamine.

Step 3. Synthesis of N-t-butoxycarbonylpiperidin-4-yl methyl ketone

To a solution of 88 mg of N-methoxy-N-methyl-1-t-butoxycarbonylisonipecotamide in 3 ml of tetrahydrofuran, 0.7 ml of 1M methylmagnesium bromide/tetrahydrofuran solution was added under cooling with ice, followed by stirring for 2 hours at the same temperature. The reaction mixture was diluted with ethyl acetate, washed sequentially with a saturated aqueous solution of ammonium chloride and brine, and dried over anhydrous sodium sulfate. The solvent was distilled off under reduced pressure, and the resulting residue was purified by silica gel chromatography (eluting solvent: hexane~hexane/ethyl acetate=5/1) to give 38 mg of the title compound.

Step 4. Synthesis of 1-(2R)-2-((1R)-3,3-difluorocyclopentyl)-2-hydroxy-2-phenylacetyl}-4-(1-oxoethyl)piperidine The title compound was prepared by a method similar to Steps 5 and 6 for Example 3, using N-t-butoxycarbonylpiperidin-4-yl methyl ketone.

Step 5. Synthesis of 4-(1-aminoethyl)-1-{(2R)-2-((1R)-3,3-difluorocyclopentyl)-2-hydroxy-2-phenylacetyl}piperidine The title compound was prepared by a method similar to Step 3 for Example 9, using 1-{(2R)-2-((1R)-3,3-difluorocyclopentyl)-2-hydroxy-2-phenylacetyl}-4-(1-oxoethyl)piperidine, as a colorless oily substance.

$^1$H-NMR (CDCl$_3$, δ ppm): 0.95(3/2H, d, J=6.3 Hz), 0.97(3/2H, d, J=6.3 Hz), 0.80–1.10 (2H, m), 1.18–1.38 (2H, m), 3.98(4H, m), 1.98–2.43 (5H, m), 2.43–2.68 (3H, m), 3.08–3.25(1H, m), 7.22–7.40(5H, m); Low resolution FAB-MS (m/e, (C$_{20}$H$_{28}$F$_2$N$_2$O$_2$+H)$^+$: 367.

EXAMPLE 12

4-(1-Aminoethyl)-1-((2R)-2-cyclopentyl-2-hydroxy-2-phenylacetyl)piperidine

The title compound was prepared by procedures similar to those for Example 11 using (2R)-2-cyclopentyl-2-hydroxy-2-phenylacetic acid, and was obtained as a colorless oily substance.

$^1$H-NMR (CDCl$_3$, δ ppm): 0.85–1.05(3H, m), 1.10–1.76 (13H, m), 1.76–1.91(2H, m), 2.35–2.71 (3H, m), 2.81–2.99 (1H, m), 3.98–4.64(2H, br), 4.95–5.50(1H, br), 7.15–7.42 (5H, m);

Low resolution FAB-MS (m/e, (C$_{20}$H$_{30}$N$_2$O$_2$+H)$^+$: 331.

EXAMPLE 13

4-(2-Aminoethyl)-1-{(2R)-2-((1R)-3,3-difluorocyclopentyl)-2-hydroxy-2-phenylacetyl}piperidine Step 1. Synthesis of ethyl N-t-butoxycarbonyl-4-piperidylideneacetate To a solution of 9.1 g of 60% oily sodium hydride in 200 ml of tetrahydrofuran, 38.0 ml of ethyl diethylphosphonoacetate was added dropwise under cooling with ice and, after stirring for 20 minutes, a solution of 31.4 g of 1-t-butoxycarbonyl-4-piperidone in 500 ml of tetrahydrofuran was added dropwise, followed by stirring for 40 minutes at the same temperature. The reaction mixture was diluted with ethyl acetate, washed sequentially with an aqueous solution of ammonium chloride, water and brine, and dried over anhydrous sodium sulfate. The solvent was distilled off under reduced pressure, and 33.5 g of the title compound was obtained by recrystallization of the resulting residual from methanol.

Step 2. Synthesis of ethyl N-t-butoxycarbonylpiperidine-4-acetate

To a solution of 355 mg of ethyl N-t-butoxycarbonyl-4-piperidylideneacetate in 10 ml of methanol, 50 mg of 10% palladium-carbon catalyst was added, followed by stirring for 13 hours under hydrogen atmosphere of 3 atmospheric pressures. Distilling the solvent off under reduced pressure after filtering the catalyst off gave 334 mg of the title compound.

Step 3. Synthesis of N-t-butoxycarbonyl-4-piperidineethanol

To a solution of 263 mg of ethyl N-t-butoxycarbonylpiperidine-4-acetate in 15 ml of tetrahydrofuran, 100 mg of lithium aluminumhydride was added under cooling with ice, followed by stirring for 20 minutes at the same temperature. Sodium sulfate decahydrate was added to the reaction mixture, which was stirred for 30 minutes, followed by filtration with Celite. Distilling off the solvent under reduced pressure gave 207 mg of the title compound.

Step 4. Synthesis of N-t-butoxycarbonyl-4-piperidylethyl methanesulfonate

To a solution of 207 mg of N-t-butoxycarbonyl-4-piperidineethanol in 10 ml of tetrahydrofuran, 0.2 ml of triethylamine and 0.1 ml of methanesulfonyl chloride were added, followed by stirring for 20 minutes at the same temperature. The reaction mixture was diluted with ethyl acetate, washed successively with a saturated aqueous solution of sodium hydrogencarbonate, water and brine, and dried over anhydrous sodium sulfate. The title compound was obtained by distilling the solvent off under reduced pressure.

Step 5. Synthesis of 4-(2-azidoethyl)-1-t-butoxycarbonylpiperidine

To a solution of N-t-butoxycarbonyl-4-piperidylethyl methanesulfonate, obtained by Step 4, in 7 ml of N,N-dimethylformamide, 100 mg of sodium azide was added at room temperature, followed by stirring for 0.5 hours under heating at 90° C. The reaction mixture was diluted with ethyl acetate, washed successively with water and brine, and dried over anhydrous sodium sulfate. Distilling the solvent off under reduced pressure gave 260 mg of the title compound.

Step 6. Synthesis of 4-(2-aminoethyl)-1-{(2R)-2-((1R)-3,3-difluorocyclopentyl)-2-hydroxy-2-phenylacetyl}-piperidine The title compound was prepared by a method similar to Steps 5 to 7 for Example 3, using 4-(2-azidoethyl)-1-t-butoxycarbonylpiperidine, and obtained as a colorless oily substance.

$^1$H-NMR (CDCl$_3$, δ ppm): 1.09–1.87(12H, m), 1.94–2.47 (4H, m), 2.47–2.74(3H, m), 3.08–3.28(1H, m), 3.99–4.44 (2H, br), 5.00–5.50(1H, br), 7.11–7.41(5H, m); Low resolution FAB-MS (m/e, (C$_{20}$H$_{28}$F$_2$N$_2$O$_2$+H)$^+$: 367.

EXAMPLE 14

4-(2-Aminoethyl)-1-((2R)-2-cyclopentyl-2-hydroxy-2-phenylacetyl)-4-piperidine

The title compound was prepared by procedures similar to those for Example 13, using (2R)-2-cyclopentyl-2-hydroxy-2-phenylacetic acid, and was obtained as a colorless oily substance.

¹H-NMR (CDCl₃, δ ppm): 0.83–1.00(1H, m), 1.23–1.80 (14H, m), 1.82–1.88(2H, m), 2.44–2.57(1H, m), 2.60–2.70 (3H, m), 2.85–2.95(1H, m), 7.20–7.42(5H, m); Low resolution FAB-MS (m/e, $(C_{20}H_{30}N_2O_2+H)^+$: 331.

EXAMPLE 15

4-(2-Aminoethyl)-1-{(2R)-2-((1R)-3,3-difluorocyclopentyl)-2-hydroxy-2-phenylacetyl}-4-methylpiperidine Step 1. Synthesis of N-t-butoxycarbonyl-4-methyl-4-vinylpiperidine To a solution of 160 mg of methyltriphenylphosphonium bromide in 5 ml of tetrahydrofuran, 0.32 ml of 1.63 M n-butyllithium/hexane solution was added dropwise under cooling with ice, followed by stirring for 30 minutes at the same temperature. To the reaction mixture, a solution of 93 mg of N-t-butoxycarbonyl-4-methylpiperidine-4-carbaldehyde in 2 ml of tetrahydrofuran was added dropwise, followed by stirring for 1 hour at the same temperature. The reaction mixture was diluted with ethyl acetate, washed with a saturated aqueous solution of ammonium chloride and brine, and dried over anhydrous magnesium sulfate. The solvent was distilled off under reduced pressure, and 15 mg of the title compound was obtained by purifying the resulting residue by silica gel column chromatography (eluting solvent: hexane/ethyl acetate=3/1).

Step 2. Synthesis of N-t-butoxycarbonyl-4-methylpiperidine-4-ethanol

To a solution of 14 mg of N-t-butoxycarbonyl-4-methyl-4-vinylpiperidine in 2 ml of tetrahydrofuran, 0.1 ml of 2.0 M borane dimethylsulfide complex/tetrahydrofuran solution was added dropwise under cooling with ice, followed by warming to room temperature and stirring for 8 hours. The reaction mixture, to which 0.5 ml of 3N sodium hydroxide aqueous solution and 0.5 ml of 35% hydrogen peroxide were added, was stirred for 11 hours at room temperature, diluted with diethyl ether, washed successively with water and brine, and dried over anhydrous magnesium sulfate. The solvent was distilled off under reduced pressure, and 13 mg of the title compound was obtained by purifying the resulting residual by preparative thin-layer chromatography [Kieselgel™60F₁₂₅, Art 5744 (Merck); chloroform/methanol=20/1].

Step 3. Synthesis of 4-(2-aminoethyl)-1-{(2R)-2-((1R)-3,3-difluorocyclopentyl)-2-hydroxy-2-phenylacetyl}-4-methylpiperidine The title compound was prepared by a method similar to Steps 4 to 6 for Example 13, using N-t-butoxycarbonyl-4-methylpiperidine-4-ethanol, and obtained as a colorless oily substance.

¹H-NMR (CDCl₃, δ ppm): 0.65–1.68(6H, m), 0.85(3H, s), 1.68–1.84(2H, m), 1.84–2.43(4H, m), 2.58(2H, dd, J=5.8, 8.4 Hz), 3.02–3.37(3H, m), 3.44–3.79(2H, m), 7.20–7.44 (5H, m); Low resolution FAB-MS (m/e, $(C_{21}H_{30}F_2N_2O_2+H)^+$: 381.

EXAMPLE 16

4-(2-Amino-1-methylethyl)-1-1-{(2R)-2-((1R)-3,3-difluorocyclopentyl)-2-hydroxy-2-phenylacetyl}piperidine The title compound was prepared by a method similar to Steps 2 for Example 3, and then Steps 3 to 6 for Example 13, using N-t-butoxycarbonyl-4-piperidineacetic acid, and was obtained as a colorless solid.

¹H-NMR (CDCl₃, δ ppm): 0.70–0.80(3H, m), 0.82–0.95 (2H, m), 1.20–1.85(1OH, m), 1.97–2.67(6H, m), 3.12–3.24 (1H, m), 7.25–7.40(5H, m) Low resolution FAB-MS (m/e, $(C_{21}H_{30}F_2N_2O_2+H)^+$: 380.

EXAMPLE 17

4-(2-Amino-1-methylethyl)-1-((2R)-2-cyclopentyl-2-hyroxy-2-phenylacetyl)piperidine The title compound was prepared by procedures similar to those for Example 16, using (2R)-2-cyclopenyl-2-hydroxy-2-phenylacetic acid, and was obtained as a colorless oily substance.

¹H-NMR (CDCl₃, δ ppm): 0.70–0.80(3H, m), 0.83–1.15 (2H, m), 1.15–1.80(12H, m), 1.81–1.91(2H, m), 2.38–2.67 (4H, m), 2.85–2.96(1H, m), 7.23–7.43(5H, m); Low resolution FAB-MS (m/e, $(C_{21}H_{32}N_2O_2+H)^+$: 345.

EXAMPLE 18

4-(1-Aminomethylpropyl)-1-{(2R)-2-((1R)-3,3-difluorocyclopentyl)-2-hydroxy-2-phenylacetyl}piperidine The title compound was prepared by procedures similar to those for Example 16, using ethyl iodide, and was obtained as a colorless oily substance.

¹H-NMR (CDCl₃, δ ppm): 0.73–0.90(3H, m), 1.90–1.13 (12H, m), 1.70–1.85 (3H, m), 1.98–2.40(3H, m), 2.40–2.68 (2H, m), 3.08–3.25(1H, m), 7.25–7.41(5H, m); Low resolution FAB-MS (m/e, $(C_{22}H_{32}F_2N_2O_2+H)^+$: 395.

EXAMPLE 19

4-2-Aminopropyl)-1-{(2R)-2-((1R)-3,3-difluorocyclopentyl)-2-hydroxy-2-phenylacetyl)piperidine The title compound was prepared by procedures similar to those for Example 11, using ethyl N-t-butoxycarbonyl-4-piperidineacetate, and was obtained as a colorless solid.

¹H-NMR (CDCl₃, δ ppm): 0.80–1.80(10H, m), 1.03(3H, d, J=6.1 Hz), 1.95–2.45(5H, m), 2.49–2.72(2H, m), 2.80–2.96(1H, m), 3.10–3.43(1H, m), 7.20–7.38(5H, m); Low resolution FAB-MS (m/e, $(C_{21}H_{30}F_2N_2O_2+H)^+$: 381.

EXAMPLE 20

4-(2-Aminopropyl)-1-((2R)-2-cyclopentyl-2-hydroxy-2-phenylacetyl)piperidine

The title compound was prepared by procedures similar to those for Example 19, using (2R)-2-cyclopentyl-2-hydroxy-2-phenylacetic acid, and was obtained as a colorless oily substance.

¹H-NMR (CDCl₃, δ ppm): 0.80–1.79(15H, m), 1.00 (3H, d, J=5.3 Hz), 1.80–1.91(2H, m), 2.45–2.57(1H, m), 2.58–2.72(1H, m), 2.80–2.95(2H, m), 3.70–4.60(2H, br), 5.25–5.60(1H, br), 7.20–7.42(5H, m) Low resolution FAB-MS (m/e, $(C_{21}H_{32}N_2O_2+H)^+$: 345.

EXAMPLE 21

4-(2-aminobutyl)-1-{(2R)-2-((1R)-3,3-difluorocyclopentyl)-2-hydroxy-2-phenylacetyl}piperidine The title compound was prepared by procedures similar to those for Example 19, using ethylmagnesium bromide, and obtained as a colorless oily substance.

¹H-NMR (CDCl₃, δ ppm): 0.55–0.99(5H, m), 0.99–1.92 (11H, m), 1.92–2.81(8H, m), 3.01–3.39(1H, m), 3.82–4.69

(2H, br), 7.14(5H, m); Low resolution FAB-MS (m/e, $(C_{22}H_{32}F_2N_2O_2+H)^+$: 395.

EXAMPLE 22

4-(2-Aminopentyl)-1-{(2R)-2-((1R)-3,3-difluorocyclopentyl)-2-hydroxy-2-phenylacetyl}piperidine The title compound was prepared by procedures similar to Step 7 for Example 3 and to those for Example 19, using allylmagnesium bromide, and was obtained as a colorless oily substance.

$^1$H-NMR (CDCl$_3$, δ ppm): 0.54–1.00(3H, m), 1.00–1.92 (13H, m), 1.92–2.47(5H, m), 2.47–2.84(3H, m), 3.06–3.39 (1H, m), 3.80–4.60(2H, br), 7.21–7.45(5H, m); Low resolution FAB-MS (m/e, $(C_{23}H_{34}F_2N_2O_2+H)^+$: 409.

EXAMPLE 23

4-(2-Amino-2-methylpropyl)-1-{(2R)-2-((1R)-3,3-difluorocyclopentyl)-2-hydroxy-2-phenylacetyl}piperidine The title compound was prepared by procedures similar to Step 2 for Example 9, Steps 1 to 2 for Example 13, Step 2 for Example 3 and Steps 2 to 7 for Example 3 successively, using N-t-butoxycarbonylpiperidine-4-methanol, and was obtained as a colorless oily substance.

$^1$H-NMR (CDCl$_3$, δ ppm): 0.75–1.40(6H, m), 1.09(6H, s), 1.40–1.90(5H, m), 1.90–2.45(4H, m), 2.50–2.80(2H, m), 3.06–3.24(1H, m), 3.80–4.40(2H, br), 7.10–7.45(5H, m); Low resolution FAB-MS (m/e, $(C_{22}H_{32}F_2N_2O_2+H)^+$: 395.

EXAMPLE 24

4-(2-Aminoethylidene)-1-{(2R)-2-((1R)-3,3-difluorocyclopentyl)-2-hydroxy-2-phenylacetyl}piperidine Step 1. Synthesis of N-t-butoxycarbonylpiperidylidene-4-ethanol To a solution of 330 mg of ethyl N-t-butoxycarbonylpiperidylidene-4-acetate in 5 ml of dichloromethane, 3.2 ml of 0.95M diisobutyl aluminumhydride was added at −75° C., followed by stirring for 1 hour at the same temperature. A saturated aqueous solution of ammonium chloride was added to the reaction mixture, which was warmed to room temperature. The reaction mixture was diluted with ethyl acetate, washed successively with water and brine, and dried over anhydrous magnesium sulfate. The title compound was obtained by distilling solvent off under reduced pressure.

Step 2. Synthesis of 4-(2-azidoethylidene)-1-t-butoxycarbonylpiperidine

To a solution of N-t-butoxycarbonylpiperidylidene-4-ethanol, obtained in Step 1, in 5 ml of tetrahydrofuran, 162 mg of triphenylphosphine, 0.13 ml of diisopropyl azodicarboxylate and 175 mg of diphenylphosphoryl azide were added successively under cooling with ice, followed by stirring for 1 hour at room temperature. The title compound was obtained by distilling the solvent off under reduced pressure.

Step 3. Synthesis of 4-(2-Azidoethylidene)-1-{(2R)-2-((1R)-3, 3-difluorocyclopentyl)-2-hydroxy-2-phenylacetyl}piperidine The title compound was prepared by procedures similar to Steps 5 and 6 for Example 3, using 4-(2-azidoethylidene)-1-t-butoxycarbonylpiperidine.

Step 4. Synthesis of 4-(2-aminoethylidene)-1-{(2R)-2-((1R)-3,3-difluorocyclopentyl)-2-hydroxy-2-phenylacetyl}piperidine To a solution of 18 mg of 4-(2-azidoethylidene)-1-{(2R)-2-((1R)-3,3-difluorocyclopentyl)-2-hydroxy-2-phenylacetyl}piperidine in 2.2 ml of 10% aqueous tetrahydrofuran, 15 mg of triphenylphosphine was added at room temperature, followed by reflux for 15 hours under heating. The solvent was distilled off under reduced pressure, and 15 mg of the title compound was obtained as a colorless oily substance by purifying the resulting residue by preparative thin-layer chromatography [Kieselgel™60F$_{654}$, Art 5744 (Merck); chloroform/methanol/aqueous ammonia=20/1].

$^1$H-NMR (CDCl$_3$, δ ppm): 1.10–2.40(12H, m), 3.00–3.28 (3H, m), 3.28–3.80(4H, m), 5.24(1H, t, J=6.6 Hz), 7.20–7.45 (5H, m) Low resolution FAB-MS (m/e, $(C_{20}H_{36}F_2N_2O_2+H)^+$: 365.

EXAMPLE 25

4-(2-Aminoethyl)-1-{(2R)-2-((1R)-3,3-difluorocyclopentyl)-2-hydroxy-2-phenylacetyl}-1,2,3,6-tetrahydropyridine Step 1. Synthesis of ethyl N-t-butoxycarbonyl-1,2,3,6-tetrahydropyridine-4-acetate To a solution of 99 mg of ethyl N-t-butoxycarbonylpiperidylidene-4-acetate in 4 ml of tetrahydrofuran, 0.4 ml of 1.5M lithium diisopropylamide/cyclohexane solution was added at −78° C., and after the mixture was stirred for 10 minutes at the same temperature, 0.05 ml of acetic acid was further added, followed by stirring for 1 hour while the mixture was being warmed to room temperature. The reaction mixture was diluted with ethyl acetate, washed successively with a saturated aqueous solution of sodium hydrogencarbonate and brine, and dried over anhydrous magnesium sulfate. The title compound was obtained by distilling the solvent off under reduced pressure.

Step 2. Synthesis of 4-(2-aminoethyl)-1-{(2R)-2-((1R)-3,3-difluorocyclopentyl)-2-hydroxy-2-phenylacetyl}-1,2,3,6-tetrahydropyridine The title compound was prepared by procedures similar to Steps 3 to 5 for Example 13 and Steps 3 and 4 for Example 24 successively, using ethyl N-t-butoxycarbonyl-1,2,3,6-tetrahydropyridine-4-acetate, and was obtained as a colorless oily substance.

$^1$H-NMR (CDCl$_3$, δ ppm): 1.20–1.92(6H, m), 1.92–2.45 (6H, m), 2.67(2H, t, J=6.7 Hz), 3.05–3.24(1H, m), 3.45–3.64 (1H, m), 3.70–3.90(1H, m), 3.90–4.40(2H, br), 5.45(1H, br), 7.20–7.45(5H, m); Low resolution FAB-MS (m/e, $(C_{20}H_{26}F_2N_2O_2+H)^+$: 365.

EXAMPLE 26

8-{(2R)-2-((1R)-3,3-difluorocyclopentyl)-2-hydroxy-2-phenylacetyl}-2,8-diazaspiro[4.5]decane Step 1. Synthesis of ethyl 4-allyl-N-t-butoxycarbonylpiperidine-4-carboxylate The title compound was prepared by a method similar to Step 2 for Example 3, using allyl bromide.

Step 2. Synthesis of 4-allyl-N-t-butoxycarbonylpiperidine-4-methanol

The title compound was prepared by a method similar to Step 1 for Example 9, using ethyl 4-allyl-N-t-butoxycarbonylpiperidine-4-carboxylate.

Step 3. Synthesis of 8-t-butoxycarbonyl-3-hydroxy-2-oxa-8-azaspiro[4.5]decane

To 89 mg of 4-allyl-N-t-butoxycarbonylpiperidine-4-methanol in a mixture of 2 ml of tetrahydrofuran and 4 ml of water, 240 mg of sodium periodate and 0.1 ml of 4% aqueous solution of osmium tetraoxide were added sequentially under cooling with ice, followed by stirring for 1 hour at the same temperature. An aqueous solution of sodium sulfite was added to the reaction mixture, which, after stirring for 30 minutes, was diluted with ethyl acetate and, after successive washing with water, a saturated aqueous solution of sodium hydrogencarbonate and brine, dried over anhydrous magnesium sulfate. Distilling the solvent off under reduced pressure gave 82 mg of the title compound.

Step 4. Synthesis of N-t-butoxycarbonyl-4-(2-hydroxyethyl)-4-hydroxymethylpiperidine To a solution of 61 mg of 8-t-butoxycarbonyl-3-hydroxy-2-oxa-8-azaspiro[4.5]decane in of 2 ml of methanol, 40 mg of sodium borohydride was added under cooling with ice, followed by stirring for 1 hour at the same temperature. Acetone was added to the reaction mixture, which was diluted with ethyl acetate and, after successive washing with water and brine, dried over anhydrous magnesium sulfate. Distilling the solvent off under reduced pressure gave 53 mg of the title compound.

Step 5. Synthesis of 8-t-butoxycarbonyl-2,8-diazaspiro[4.5]decane

The title compound was prepared by procedures similar to Steps 4 and 5 for Example 13 and Step 4 for Example 24, using N-t-butoxycarbonyl-4-(2-hydroxyethyl)-4-hydroxymethylpiperidine.

Step 6. Synthesis of 2-benzyl-8-t-butoxycarbonyl-2,8-diazaspiro[4.5]decane

To a solution of 10 mg of 8-t-butoxycarbonyl-2,8-diazaspiro[4.5]decane in 1 ml of tetrahydrofuran, 0.01 ml of acetic acid, 0.02 ml of benzaldehyde and 30 mg of sodium triacetoxyborohydride were added successively at room temperature, followed by stirring for 2 hours at the same temperature. The reaction mixture was diluted with ethyl acetate and, after successive washing with a saturated aqueous solution of sodium hydrogen-carbonate, water and brine, dried over anhydrous sodium sulfate. The solvent was distilled off under reduced pressure, and 9 mg of the title compound was obtained by purifying the resulting residue by preparative thin-layer chromatography [Kieselgel™60F$_{254}$, Art 5744 (Merck); chloroform/methanol=15/1].

Step 7. Synthesis of 8-{(2R)-2-((1R)-3,3-difluorocyclopentyl)-2-hydroxy-2-phenylacetyl}-2,8-diazaspiro[4.5]-decane The title compound was prepared by procedures similar to Steps 5 to 7 for Example 3, using 2-benzyl-8-t-butoxycarbonyl-2,8-diazaspiro[4.5]decane, and was obtained as a pale yellow oily substance.

$^1$H-NMR (CDCl$_3$, δ ppm): 0.79–1.83(6H, m), 1.47(2H, t, J=7.1 Hz), 1.92–2.55(4H, m), 2.60(2H, s), 2.91(2H, t, J=7.1 Hz), 3.08–3.22(1H, m), 3.22–3.56(4H, m), 7.69(5H, m); Low resolution FAB-MS (m/e, (C$_{21}$H$_{28}$F$_2$N$_2$O$_2$+H)$^+$: 379.

EXAMPLE 27

1-Aminomethyl-6-{(2R)-2-((1R)-3,3-difluorocyclopentyl)-2-hydroxy-2-phenylacetyl}-6-azaspiro[2.5]octane Step 1. Synthesis of 6-t-butoxycarbonyl-6-azaspiro-[2.5]oct-1-ylmethanol To a solution of 42 mg of N-t-butoxycarbonylpiperidylidene-4-ethanol in 3 ml of diethyl ether, 0.5 ml of 1.0 M diethyl zinc/hexane solution was added under cooling with ice and, after stirring for 5 minutes, a solution of 0.05 ml of diiodomethane in 2 ml of diethyl ether was added dropwise to the reaction mixture, which was warmed to room temperature, followed by stirring for 3 hours. The reaction mixture was diluted with diethyl ether and, after successive washing with water and brine, dried over anhydrous magnesium sulfate. Distilling the solvent off under reduced pressure gave the title compound.

Step 2. Synthesis of 1-aminomethyl-6-{(2R)-2-((1R)-3,3-difluorocyclopentyl)-2-hydroxy-2-phenylacetyl}-6-azaspiro[2.5]octane The title compound was prepared by procedures similar to Steps 2 to 4 for Example 24, using 6-t-butoxycarbonyl-6-azaspiro[2.5]oct-1-ylmethanol, and was obtained as a pale yellow oily substance.

$^1$H-NMR (CDCl$_3$, δ ppm): 0.14–0.09(1H, m), 0.35–0.48 (1H, m), 0.54–1.37(5H, m), 1.50–2.43(8H, m), 2.52–2.69 (2H, m), 3.00–3.41(3H, m), 7.18–7.43(5H, m); Low resolution FAB-MS (m/e, (C$_{21}$H$_{28}$F$_2$N$_2$O$_2$+H)$^+$: 379.

EXAMPLE 28

2-{(2R)-2-((1R)-3,3-difluorocyclopentyl)-2-hydroxy-2-phenylacetyl}-2,8-diazaspiro[4.5]decane The title compound was prepared by procedures similar to Steps 3 and 4 for Example 1, using 8-t-butoxycarbonyl-2,8-diazaspiro[4.5]decane, and was obtained as a colorless oily substance.

$^1$H-NMR (CDCl$_3$, δ ppm): 0.81–0.95(1H, m), 1.02–1.85 (9H, m), 1.95–2.47(6H, m), 2.64–2.88(1H, m), 2.88–3.11 (1H, m), 3.13–3.42(2H, m) 3.47–3.60(1H, m), 5.05–5.27 (1H, m), 7.21–7.45(5H, m) Low resolution FAB-MS (m/e, (C$_{21}$H$_{28}$F$_2$N$_2$O$_2$+H)$^+$: 379.

EXAMPLE 29

9-{(2R)-2-((1R)-3,3-difluorocyclopentyl)-2-hydroxy-2-phenylacetyl}-cis-4,9-diazabicyclo[5.3.0]decane Step 1. Synthesis of cis-N-t-butoxycarbonyl-3,4-bis(2-hydroxyethyl)pyrrolidine The title compound was prepared by procedures similar to Step 1 for Example 1 and Steps 3 and 4 for Example 26, using cis-8-azabicyclo[4.3.0]non-3-ene.

Step 2. Synthesis of 4-benzyl-9-t-butoxycarbonyl-cis-4,9-diazabicyclo[5.3.0]decane To a solution of 9.7 g of cis-N-t-butoxycarbonyl-3,4-bis (2-hydroxyethyl)pyrrolidine in 200 ml of chloroform, 21 ml of triethylamine and 7 ml of methanesulfonyl chloride were added under cooling with ice, followed by stirring for 1 hour at the same temperature. The reaction mixture was diluted with chloroform, washed sequentially with a saturated aqueous solution of sodium hydrogencarbonate and brine, dried over anhydrous magnesium sulfate. The solvent was distilled off under reduced pressure, the resulting residue was dissolved in 200 ml of toluene, and 21 g of potassium carbonate and 7 ml of benzylamine were added thereto, followed by reflux for 12 hours under heating. The reaction mixture was diluted with ethyl acetate, washed with water and brine, and dried over anhydrous magnesium sulfate. The solvent was distilled off under reduced pressure, and 5.6 g of the title compound was obtained by purifying the resulting residue by silica gel column chromatography (eluting solvent: chloroform/methanol=40/1).

Step 3. Synthesis of 9-{(2R)-2-((1R)-3,3-difluorocyclopentyl)-2-hydroxy-2-phenylacetyl}-cis-4,9-diazabicyclo[5.3.0]decane The title compound was prepared by procedures similar to Steps 5 to 7 for Example 3 using 4-benzyl-9-t- butoxycarbonyl-cis-4,9-diazabicyclo[5.3.0]decane, and was obtained as a colorless foamy substance.

$^1$H-NMR (CDCl$_3$, δ ppm): 1.10–1.98(8H, m), 1.98–2.70 (8H, m), 2.70–3.60(5H, m), 3.60–3.86(1H, brs), 7.20–7.50 (5H, m); Low resolution FAB-MS (m/e, (C$_{21}$H$_{28}$F$_2$N$_2$O$_2$+H)$^+$: 379.

EXAMPLE 30

3-{(2R)-2-((1R)-3,3-difluorocyclopentyl)-2-hydroxy-2-phenylacetyl}-3,7-diazabicyclo[3.3.0]octane monohydrochloride The title compound was prepared by procedures similar to Steps 3 and 4 for Example 1, using 3-t-butoxycarbonyl-3,7-diazabicyclo[3.3.0]octane, and was obtained as a white solid.

$^1$H-NMR (CD$_3$OD, δ ppm): 1.75–2.13(8H, m), 2.77–3.23 (5H, m), 3.40–3.73(4H, m), 7.26–7.50(5H, m); Low resolution FAB-MS (m/e, (C$_{19}$H$_{24}$F$_2$N$_2$O$_2$+H)$^+$: 351.

EXAMPLE 31

7-{(2R)-2-((1R)-3,3-difluorocyclopentyl)-2-hydroxy-2-phenylacetyl}-2,7-diazaspiro[4.5]decane The title compound was prepared by procedures similar to Steps 5 to 7 for Example 3, using 2-benzyl-7-t-butoxycarbonyl-2,7-diazaspiro[4.5]decane, and was obtained as a colorless oily substance.

$^1$H-NMR (CDCl$_3$, δ ppm): 1.10–2.40(12H, m), 2.97–3.82 (9H, m), 5.05–5.36(1H, m), 7.20–7.50(5H, m); Low resolution FAB-MS (m/e, (C$_{21}$H$_{28}$F$_2$N$_2$O$_2$+H)$^+$: 379.

EXAMPLE 32

3-{(2R)-2-((1R)-3,3-difluorocyclopentyl)-2-hydroxy-2-phenylacetyl}-3,9-diazaspiro[5.5]undecane monohydrochloride The title compound was prepared by procedures similar to Steps 3 and 4 for Example 1, using 3-t-butoxycarbonyl-3,9-diazaspiro[5.5]undecane, and was obtained as a white solid.

$^1$H-NMR (CDCl$_3$, δ ppm): 0.60–2.40(14H, m), 2.90–3.70 (9H, m), 4.77(1H, s), 7.20–7.45(5H, m), 9.40(1H, brs); Low resolution FAB-MS (m/e, (C$_{22}$H$_{30}$F$_2$N$_2$O$_2$+H)$^+$: 393.

EXAMPLE 33

9-{(2R)-2-((1R)-3,3-difluorocyclopentyl)-2-hydroxy-2-phenylacetyl}-2.9-diazaspiro[5.5]undecane The title compound was prepared by procedures similar to Steps 5 to 7 for Example 3, using 2-benzyl-9-t-butoxycarbonyl-2, 9-diazaspiro[5.5]undecane, and was obtained as a color less oily substance.

$^1$H-NMR (CDCl$_3$, δ ppm): 0.70–1.69(7H, m), 1.69–1.94 (2H, m), 1.94–2.49(6H, m), 2.53(2H, s), 2.69–2.91(2H, m), 3.05–3.88(5H, m), 4.82–5.73(1H, brs), 7.33–7.46(5H, m); Low resolution FAB-MS (m/e, (C$_{22}$H$_{30}$F$_2$N$_2$O$_2$+H)$^+$: 393.

EXAMPLE 34

(5R*)- and (5S*)-2-{(2R)-2-((R)-3,3-difluorocyclopentyl)-2-hydroxy-2-phenylacetyl}-2,7-diazaspiro[4.4]nonane After carrying out reactions similar to those of Steps 3 and 4 for Example 1, using 2-t-butoxycarbonyl-2,7-diazaspiro[4.4]nonane, diastereomers were separated by preparative thin-layer chromatography [Kieselgel™60F$_{254}$, Art 5744 (Merck); chloroform/methanol/ammonia water=50/10/1]. A title compound that was named a (5R*)-substance expediently as a low polar substance and another that was named a (5S*)-substance expediently as a high polar substance were obtained both as colorless oily substances.

(5R*)-substance;

$^1$H-NMR (CDCl$_3$, δ ppm): 0.80–2.45(12H, m), 2.45–3.70 (8H, m), 7.15–7.50(5H, m); Low resolution FAB-MS (m/e, (C$_{20}$H$_{26}$F$_2$N$_2$O$_2$+H)$^+$: 365; (5S*)-substance; $^1$H-NMR (CDCl$_3$, δ ppm): 0.80–2.65(12H, m), 2.65–3.80(8H, m), 7.15–7.70(5H, m); Low resolution FAB-MS (m/e, (C$_{20}$H$_{26}$F$_2$N$_2$O$_2$+H)$^+$: 365.

EXAMPLE 35

3-{(2R)-2-((1R)-3,3-difluorocyclopentyl)-2-hydroxy-2-phenylacetyl}-3,7-diazabicyclo[3.3.0]oct-1(5)-ene The title compound was prepared by a method similar to Step 6 for Example 3, using 3,7-diazabicyclo[3.3.0]oct-1(5)-ene dihydrobromide, and was obtained as a white solid.

$^1$H-NMR (CDCl$_3$, δ ppm): 1.67–2.50(6H, m), 3.20–3.35 (1H, m), 3.35–4.36 (8H, m), 7.29–7.48(5H, m); Low resolution FAB-MS (m/e, (C$_{19}$H$_{22}$F$_2$N$_2$O$_2$+H)$^+$: 349.

EXAMPLE 36

2-{(2R)-2-((1R)-3,3-difluorocyclopentyl)-2-hydroxy-2-phenylacetyl}-4-methyl-2,8-diazaspiro[4.5]decane The title compound was prepared by procedures similar to Steps 3 and 4 for Example 1, using 8-t-butoxycarbonyl-4-methyl-2,8-diazaspiro[4.5]decane, and was obtained as a colorless oily substance.

$^1$H-NMR (CDCl$_3$, δ ppm): 0.52–2.56(14H, m), 2.56–3.03 (4H, m), 3.03–3.82(5H, m), 7.18–7.47(5H, m); Low resolution FAB-MS (m/e, (C$_{22}$H$_{30}$F$_2$N$_2$O$_2$+H)$^+$: 393.

EXAMPLE 37

8-{(2R)-2-((1R)-3,3-difluorocyclopentyl)-2-hydroxy-2-phenylacetyl}-3-methyl-2,8-diazaspiro[4.5]decane The title compound was prepared by procedures similar to Steps 5 to 7 for Example 3, using 2-benzyl-8-t-butoxycarbonyl-3-methyl-2,8-diazaspiro[4.5]decane, and was obtained as a colorless oily substance.

$^1$H-NMR (CDCl$_3$, δ ppm): 0.85–1.87(8H, m), 1.95–2.42 (4H, m), 1.11(3H, d, J=6.2 Hz), 2.57(1H, d, J=1 Hz), 2.75(1H, d, J=11 Hz), 3.05–3.79(6H, m), 5.12–5.40 (1H, m), 7.20–7.41(5H, m); Low resolution FAB-MS (m/e, (C$_{22}$H$_{30}$F$_2$N$_2$O$_2$+H)$^+$: 393.

EXAMPLE 38

8-{(2R)-2-((1R)-3,3-difluorocyclopentyl)-2-hydroxy-2-phenylacetyl}-4-methyl-2,8-diazaspiro[4.5]decane The title compound was prepared by procedures similar to Steps 5 to 7 for Example 3, using 2-benzyl-8-t-butoxycarbonyl-4-methyl-2,8-diazaspiro[4.5]decane, and was obtained as a colorless oily substance.

$^1$H-NMR (CDCl$_3$, δ ppm): 0.56–1.92(14H, m), 1.92–2.54 (6H, m), 2.54–2.93(2H, m), 2.93–3.23(1H, m), 7.10–7.40 (5H, m); Low resolution FAB-MS (m/e, (C$_{22}$H$_{30}$F$_2$N$_2$O$_2$+H)$^+$: 393.

EXAMPLE 39

7-{(2R)-2-((1R)-3,3-difluorocyclopentyl)-2-hydroxy-2-phenylacetyl}-2,7-diazaspiro[3.5]nonane monohydrochloride The title compound was prepared by procedures similar to Steps 3 to 4 for Example 1, using 2-t-butoxycarbonyl-2,7-diazaspiro[3.5]nonane, and was obtained as a white solid.

$^1$H-NMR (CD$_3$OD, δ ppm): 1.20–2.11(10H, m), 2.95–3.12(1H, m), 3.12–4.00(8H, m), 7.20–7.45(5H, m); Low resolution FAB-MS (m/e, (C$_{20}$H$_{26}$F$_2$N$_2$O$_2$+H)$^+$: 365.

EXAMPLE 40

(1R*, 6S*)- and (1S*, 6R*)-3-{(2R)-2-((1R)-3,3-difluorocyclopentyl)-2-hydroxy-2-phenylacetyl}-3,8-diazaspiro[4.3.0]nonane monohydrochloride After carrying out a reaction similar to that of Step 3 for Example 1, using 8-t-butoxycarbonyl-cis-3,8-diazabicyclo[4.3.0]nonane, diastereomers were separated by preparative thin-layer chromatography[Kieselgel™ 60F$_{254}$, Art 5744 (Merck); hexane/ethyl acetate=½]. A t-butoxycarbonyl protector for a title compound, named a (1R*, 6S*)-substance expediently as a low polar substance, and a t-butoxycarbonyl protector for another title compound, named a (1S*, 6R*)-substance expediently as a high polar substance, were obtained, followed by treatment of both by a method similar to Step 4 for Example 1 to prepare title compounds, both obtained as colorless oily substances.

(1R*, 6S*)-substance; $^1$H-NMR (CD$_3$OD, δ ppm): 1.20–2.43(12H, m), 2.70–3.68(6H, m), 4.15–4.35(1H, m), 7.25–7.55(5H, m); Low resolution FAB-MS (m/e, (C$_{20}$H$_{26}$F$_2$N$_2$O$_2$+H)$^+$: 365; (1S*, 6R*)-substance; $^1$H-NMR (CD$_3$OD, δ ppm): 0.80–2.10(11H, m), 2.30–2.50(1H, m), 2.70–3.80(6H, m), 4.05–4.32(1H, m); 7.27–7.44(5H, m); Low resolution FAB-MS (m/e, (C$_{20}$H$_{26}$F$_2$N$_2$O$_2$+H)$^+$: 365.

EXAMPLE 41

(1R*, 6R*)- and (1S*, 6S*)-8-{(2R)-2-((R)-3,3-difuorocyclopentyl)-2-hydroxy-2-phenylacetyl}-3,8-diazabicyclo[4.3.0]nonane monohydrochloride After carrying out a reaction similar to that of Step 6 for Example 3, using 3-benzyl-cis-3,8-diazabicyclo[4.3.0]nonane, diastereomers were separated by silica gel chromatography (eluting solvent: ethyl acetate). A benzyl protector for a title compound, named a (1R*, 6R*)-substance expediently as an earlier eluted substance, and a benzyl protector for another title compound, named a (1S*, 6S*)-substance expediently as a high polar substance, were obtained, followed by treatment of both by procedures similar to Step 7 for Example 3 and Step 4 for Example 1 to prepare title compounds, both obtained as colorless solids.

(1R*, 6R*)-substance; $^1$H-NMR (CD$_3$OD, δ ppm): 0.85–1.05(1H, m), 1.20–1.55(1H, m), 1.70–2.55 (7H, m), 2.81–2.88(1H, m), 2.90–3.24(5H, m), 3.25–3.90(4H, m), 7.25–7.50(5H, m); Low resolution FAB-MS (m/e, (C$_{20}$H$_{26}$F$_2$N$_2$O$_2$+H)$^+$: 365; (1S*, 6S*)-substance; $^1$H-NMR (CD$_3$OD, δ ppm): 1.20–2.12(7H, m), 2.18–2.70 (2H, m), 2.90–3.20(6H, m), 3.20–3.81(4H, m), 7.22–7.47(5H, m); Low resolution FAB-MS (m/e, (C$_{20}$H$_{26}$F$_2$N$_2$O$_2$+H)$^+$: 365.

EXAMPLE 42

(1R*, 7R*)- and (1S*, 7S*)-9-{(2R)-2-((R)-3,3-difuorocyclolpentyl)-2-hydroxy-2-phenylacetyl}-3,9-diazabicyclo[5.3.0]decane After carrying out reaction similar to those of Steps 5 and 6 for Example 3, using 3-benzyl-9-t-butoxycarbonyl-cis-3,9-diazabicyclo[5.3.0]decane, diastereomers were separated by preparative thin-layer chromatography[Kieselgel™ 60F$_{254}$, Art 5744 (Merck); chloroform/methanol=20/1]. A benzyl protector for a title compound, named a (1R*, 7R*)-substance expediently as a low polar substance, and a benzyl protector for another title compound, named a (1S*, 7S*)-substance expediently as a high polar substance, were obtained, followed by treatment of both by a method similar to Step 7 for Example 3 to prepare title compounds, both obtained as colorless oily substances.

(1R*, 7R*)-substance; $^1$H-NMR (CDCl$_3$, δ ppm): 1.20–2.28(14H, m), 2.40–2.98(2H, m), 3.10–3.77 (5H, m), 7.26–7.39(5H, m); Low resolution FAB-MS (m/e, (C$_{21}$H$_{28}$F$_2$N$_2$O$_2$+H)$^+$: 379; (1S*, 7S*)-substance; $^1$H-NMR (CDCl$_3$, δ ppm): 1.20–1.87(6H, m), 1.96–2.63 (10H, m), 2.82–3.77(5H, m), 7.22–7.42(5H, m); Low resolution FAB-MS (m/e, (C$_{21}$H$_{28}$F$_2$N$_2$O$_2$+H)$^+$: 379.

EXAMPLE 43

(1R*)- and (1S*)-8-{(2R)-2-((1R)-3,3-difluorocyclopentyl)-2-hydroxy-2-phenylacetyl}-1-methyl-2,8-diazaspiro[4.5]decane After carrying out reactions similar to those of Steps 5 and 6 for Example 3, using 2-benzyloxycarbonyl-8-t-butoxycarbonyl-1-methyl-2,8-diazaspiro[4.5]decane, diastereomers were separated by high performance liquid chromatography (Chiralpak AD, solvent: hexane/2-propanol=9/1). A benzyloxycarbonyl protector for a title compound, named a (1R*)-substance expediently as an earlier eluted substance, and a benzyloxycarbonyl protector for another title compound, named a (1S*)-substance expediently as a high polar substance, were obtained, followed by treatment of both by a method similar to Step 7 for Example 3 to prepare title compounds, both obtained as colorless oily substances.

(1R*)-substance; $^1$H-NMR (CDCl$_3$, δ ppm): 0.76–1.88 (3H, m), 1.43–1.83 (10H, m), 1.96–2.43(4H, m), 2.56(1H, q, J=6.9 Hz), 2.64–3.00(4H, m), 3.12–3.25(1H, m), 7.25–7.40 (5H, m); Low resolution FAB-MS (m/e, (C$_{22}$H$_{30}$F$_2$N$_2$O$_2$+H)$^+$: 393; (1S*)-substance; $^1$H-NMR$^{(CDCl_3)}$, δ ppm): 1.19–2.34(15H, m), 2.45–3.39(8H, m), 7.25–7.38(5H, m); Low resolution FAB-MS (m/e, (C$_{22}$H$_{30}$F$_2$N$_2$O$_2$+H)$^+$: 393.

EXAMPLE 44

2-{(2R)-2-((1R)-3,3-difluorocyclopentyl)-2-hydroxy-2-phenylacetyl}-2,7-diazaspiro[4.5]decane The title compound was prepared by procedures similar to Steps 3 to 4 for Example 1, using 7-t-butoxycarbonyl-2,7-diazaspiro[4.5]decane, and was obtained as a colorless oily substance.

$^1$H-NMR (CDCl$_3$, δ ppm): 0.72–2.95(16H, m), 3.14–3.37 (3H, m), 3.42–3.60(2H, m), 5.04–5.40(1H, m), 7.00–7.46 (5H, m); Low resolution FAB-MS (m/e, (C$_{21}$H$_{28}$F$_2$N$_2$O$_2$+H)$^+$: 379.

EXAMPLE 45

(1R*, 7R*)- and (1S*, 7S*)-9-{(2R)-2-((1R)-3,3-difluorocyclopentyl)-2-hydroxy-2-phenylacetyl}-4,9-diazabicyclo[5.3.0]decane After carrying out reactions similar to those of Step 5 and 6 for Example 3, using 4-benzyl-9-t-butoxycarbonyl-trans-4,9-diazabicyclo[5.3.0]decane, diastereomers were separated by preparative thin-layer chromatography

[Kieselgel™ 60F$_{254}$, Art 5744 (Merck); chloroform/methanol=20/1]. A benzyl protector for a title compound, named a (1R*, 7R*)-substance expediently as a low polar substance, and a benzyl protector for another title compound, named a (1S*, 7S*)-substance expediently as a high polar substance, were obtained, followed by treatment of both by a method similar to Step 7 for Example 3 to prepare title compounds, both obtained as colorless oily substances.

(1R*, 7R*)-substance; $^1$H-NMR (CDCl$_3$, δ ppm): 1.18–2.39(12H, m), 2.65–2.80(1H, m), 2.92–3.25(4H, m), 2.25–3.40(2H, m), 3.50–3.65(1H, m), 3.83–3.98(1H, m), 5.02(1H, s), 7.20–7.45(5H, m); Low resolution FAB-MS (m/e, (C$_{21}$H$_{28}$F$_2$N$_2$O$_2$+H)$^+$: 379; (1S*, 7S*)-substance; $^1$H-NMR (CDCl$_3$, δ ppm): 0.79–2.40(12H, m), 2.60–2.81 (1H, m), 2.81–3.66(6H, m), 3.66–3.93(2H, m), 7.20–7.45 (5H, m); Low resolution FAB-MS (m/e, (C$_{21}$H$_{28}$F$_2$N$_2$O$_2$+H)$^+$: 379.

EXAMPLE 46

8-{(2R)-2-((1R)-3,3-difluorocyclopentyl)-2-hydroxy-2-phenylacetyl}-1-ethyl-2,8-diazaspiro[4.5]decane The title compound was prepared by procedures similar to Steps 5 to 7 for Example 3, using 2-benzyloxycarbonyl-8-t-butoxycarbonyl-1-ethyl-2,8-diazaspiro[4.5]decane, and was obtained as a colorless oily substance.

$^1$H-NMR (CDCl$_3$, δ ppm): 1.01(3H, t, J=3.0 Hz), 1.10–2.40(16H, m), 2.59–2.79(3H, m), 3.10–3.30(3H, m), 7.24–7.40(5H, m); Low resolution FAB-MS (m/e, (C$_{23}$H$_{32}$F$_2$N$_2$O$_2$+H)$^+$: 407.

EXAMPLE 47

9-{(2R)-2-((1R)-3,3-difluorocyclopentyl)-2-hydroxy-2-phenylacetyl}-3-methyl-cis-4,9-diazabicyclo[5.3.0]decane The title compound was prepared by procedures similar to Steps 5 to 7 for Example 3, using 4-benzyl-t-butoxycarbonyl-3-methyl-cis-4,9-diazabicyclo[5.3.0] decane, and was obtained as a colorless oily substance.

$^1$H-NMR (CDCl$_3$, δ ppm): 1.07(3H, d, J=6.6 Hz), 1.40–2.40(13H, m), 2.59–3.80(7H, m), 7.27–7.40(5H, m); Low resolution FAB-MS (m/e, (C$_{22}$H$_{30}$F$_2$N$_2$O$_2$+H)$^+$: 393.

EXAMPLE 48

4-Aminomethyl-1-{(2R)-2-((1R)-3,3-difluorocyclopentyl)-2-hydroxy-2-phenylacetyl}-1,2,3,6-tetrahydropyridine The title compound was prepared by procedures similar to Steps 3 to 4 for Example 1, using 4-t-butoxycarbonylaminomethyl-1,2,3,6-tetrahydropyridine, and was obtained as a colorless oily substance.

$^1$H-NMR (CDCl$_3$, δ ppm): 1.50–2.80(9H, m), 3.05–3.30 (4H, m), 3.50–3.70(2H, m), 3.80–3.94(2H, m), 3.94–4.38 (1H, br), 5.40–5.58(1H, br), 7.15–7.46(5H, m); Low resolution FAB-MS (m/e, (C$_{19}$H$_{24}$F$_2$N$_2$O$_2$+H)$^+$: 351.

EXAMPLE 49

(5R*)- and (5S*)-2-{(2R)-2-((1R)-3,3-difluorocyclopentyl)-2-hydroxy-2-phenylacetyl}-2,7-diazaspiro[4.5]decane After carrying out a reaction similar to that of Step 3 for Example 1, using 7-t-butoxycarbonyl-2,7-diazaspiro[4.5] decane, diastereomers were separated by preparative thin-layer chromatography [Kieselgel™ 60F$_{254}$, Art 5744 (Merck); hexane/ethyl acetate=1/1]. A t-butoxycarbonyl protector for a title compound, named a (5R*)-substance expediently as a low polar substance, and a t-butoxycarbonyl protector for another title compound, named a (5S*)-substance expediently as a high polar substance, were obtained, followed by treatment of both by a method similar to Step 4 for Example 1 to prepare title compounds, both obtained as colorless oily substances.

(5R*)-substance; $^1$H-NMR (CDCl$_3$, δ ppm): 0.75–1.92 (8H, m), 1.92–2.62 (5H, m), 2.42(2H, s), 2.62–2.80(2H, m), 3.13–3.42 (3H, m), 3.42–3.64(2H, m), 5.10–5.38(1H, m), 7.18–7.50(5H, m); Low resolution FAB-MS (m/e, (C$_{21}$H$_{28}$F$_2$N$_2$O$_2$+H)$^+$: 379; (5S*)-substance; $^1$H-NMR (CDCl$_3$, δ ppm): 1.00–1.61(6H, m), 1.61–1.95 (3H, m), 1.95–2.48(4H, m), 2.48–3.11(4H, m), 3.11–3.40(3H, m), 3.40–3.65(2H, m), 5.10–5.50(1H, m), 7.25–7.52(5H, m); Low resolution FAB-MS (m/e, (C$_{21}$H$_{28}$F$_2$N$_2$O$_2$+H)$^+$: 379.

REFERENTIAL EXAMPLE 1

(2R)-2-((1R)-3,3-difluorocyclopentyl)-2-hydroxy-2-phenylacetic acid

Step 1. Synthesis of (2R,5R)-2-(t-butyl)-5-((1R)-3-oxocyclopentyl)-5-phenyl-1,3-dioxolan-4-one and (2R,5R)-2-(t-butyl)-5-((1S)-3-oxocyclopentyl)-5-phenyl-1,3-dioxolan-4-one To a mixture of 510 mg of (2R,5R)-2-(t-butyl)-5-phenyl-1,3-dioxolan-4-one, synthesized by the method of D. Seebach et al.[*Tetrahedron*, Vol. 40, pp. 1313–1324 (1984)], in 20 ml of tetrahydrofuran and 1 ml of hexamethylphosphoric triamide, 1.7 ml of 1.5M lithium diisopropylamide solution in hexane was added dropwise at −78° C., followed by stirring for 30 minutes. Then a solution of 285 mg of cyclopentenone in 1.5 ml of tetrahydrofuran was added, followed by further stirring for 1.5 hours. The reaction mixture was diluted with ethyl acetate, washed successively with a saturated aqueous solution of ammonium chloride, water and brine, and dried over anhydrous magnesium sulfate. The solvent was distilled off under reduced pressure, and the resulting residue was purified by medium pressure silica gel column chromatography (eluting solvent: hexane/ethyl acetate=15/1~10/1) to give 150 mg and 254 mg, respectively, of the title compounds as oil. The configuration of each of the compounds was determined from NOE of NMR.

Step 2. Synthesis of (2R,5R)-2-(t-butyl)-5-((1R)-3,3-difluorocyclopentyl)-5-phenyl-1,3-dioxolan-4-one To a solution of 2.8 g of (2R,5R)-2-(t-butyl)-5-((1R)-3-oxocyclopentyl)-5-phenyl-1,3-dioxolan-4-one in 30 ml of chloroform, 4.89 ml of diethylaminosulfur trifluoride was added under cooling with ice, followed by stirring for 20 hours at room temperature. The reaction mixture was diluted with chloroform, washed sequentially with water and brine, and dried over anhydrous magnesium sulfate. The solvent was distilled off under reduced pressure, and 2.4 g of the title compound was obtained by purifying the resulting residue by silica gel column chromatography (eluting solvent: hexane/ethyl acetate=20/1).

Step 3. Synthesis of (2R)-2-((1R)-3,3-difluorocyclopentyl)-2-hydroxy-2-phenylacetic acid To a solution of 2.4 g of (2R,5R)-2-(t-butyl)-5-((1R)-3,3-difluorocyclopentyl)-5-phenyl-1,3-dioxolan-4-one in 30 ml of methanol, 10 ml of a 1N aqueous solution of sodium hydroxide was added, followed by stirring for 3 hours at room temperature. After distilling the methanol off under reduced pressure, the reaction mixture was diluted with water, and washed with diethyl ether. The aqueous layer was acidified with 1N hydrochloric acid and extracted with diethyl ether, while the organic layer was dried over anhydrous magnesium sulfate. Distilling the solvent off under reduced pressure gave 1.66 g of the title compound.

REFERENTIAL EXAMPLE 2

(2R)-2-((1S)-3,3-difluorocyclopentyl)-2-hydroxy-2-phenylacetic acid

The title compound was prepared by a method similar to that of Referential Example 1, using (2R,5R)-2-(t-butyl)-5-((1S)-3-oxocyclopentyl)-5-phenyl-1,3-dioxoian-4-one.

REFERENTIAL EXAMPLE 3

(2R)-2-((1S)-3-fluorocyclopentyl)-2-hydroxy-2-phenylacetic acid

Step 1. Synthesis of (2R,5R)-2-(t-butyl)-5-((1S)-3-hydroxycyclopentyl)-5-phenyl-1,3-dioxolan-4-one To a solution of 169 mg of (2R,5R)-2-(t-butyl)-5-((1S)-3-oxocyclopentyl)-5-phenyl-1,3-dioxo-lan-4-one in 2 ml of methanol, 71 mg of sodium borohydride was added under cooling with ice, followed by stirring for 30 minutes at the same temperature. The reaction mixture was diluted with diethyl ether, washed with water and brine, and dried over anhydrous magnesium sulfate. Distilling the solvent off under reduced pressure gave 157 mg of the title compound as a colorless oily substance.

Step 2. Synthesis of (2R)-2-((1S)-3-fluorocyclopentyl)-2-hydroxy-2-phenylacetic acid The title compound was prepared by procedures similar to those of Steps 2 and 3 for Referential Example 1, using (2R,5R)-2-(t-butyl)-5-((1S)-3-hydroxycyclopentyl)-5-phenyl-1,3-dioxolan-4-one.

REFERENTIAL EXAMPLE 4

(2R)-2-((1R)-3,3-difluorocyclopentyl)-2-hydroxy-2-phenylacetic acid

Step 1. Synthesis of (2R,5R)-2-(t-butyl)-5-((1R,2R,3S,6R,7S)-5-oxotricyclo[5.2.1.0$^{2,6}$]dec-8-en-3-yl)-5-phenyl-1,3-dioxolan-4-one To a solution of 32 g of (2R,5R)-2-(t-butyl)-5-phenyl-1,3-dioxolan-4-one in 1.1 l of tetrahydrofuran, 105 ml of a 1.5M solution of lithium diisopropylamide in hexane was added dropwise and, after stirring for 30 minutes, a solution of 23.4 g of (1S,2R,6R,7R)-tricyclo[5.2.1.0$^{2,6}$]deca-4,8-dien-3-one in 300 ml of tetrahydrofuran was added, followed by further stirring for 1.5 hours. The reaction mixture was diluted with ethyl acetate, washed successively with a saturated aqueous solution of ammonium chloride, water and brine, and dried over anhydrous magnesium sulfate. The solvent was distilled off, and 36.9 g of the title compound was obtained as a white solid by recrystallizing the resulting residue using hexane-ethyl acetate.

Step 2. Synthesis of (2R,5R)-2-(t-butyl)-5-((1S)-4-oxo-2-cyclopentenyl)-5-phenyl-1,3-dioxolan-4-one A solution of 25.6 g of (2R,5R)-2-(t-butyl)-5-((1R,2R,3S,6R,7S)-5-oxotricyclo[5.2.1.0$^{2,6}$]dec-8-en-3-yl)-5-phenyl-1,3-dioxolan-4-one, obtained by Step 1, in 350 ml of 1,2-dichlorobenzene was stirred for 7 hours under heating at 175° C. in a nitrogen atmosphere. The depositing solid was washed with hexane after filtration to give 14 g of the title compound as a white solid.

Step 3. Synthesis of (2R,5R)-2-(t-butyl)-5-((1R)-3-oxo-cyclopentyl)-5-phenyl-1,3-dioxolan-4-one To a solution of 19.1 g of (2R,5R)-2-(t-butyl)-5-((1S)-4-oxo-2-cyclopentenyl)-5-phenyl-1,3-dioxolan-4-one, obtained by Step 2, in 700 ml of ethyl acetate, 2.0 g of 10% palladium-carbon was added, followed by stirring for 2 hours at ambient temperature under a hydrogen atmosphere. After filtering the catalyst off, the solvent was distilled off under reduced pressure, and the resulting residue was recrystallized using hexane-ethyl acetate to give 14 g of the title compound as a white solid.

Step 4. Synthesis of (2R,5R)-2-(t-butyl)-5-((1R)-3-hydroxyiminocyclopentyl)-5-phenyl-1,3-dioxolan-4-one To a solution of 46 mg of (2R,5R)-2-(t-butyl)-5-((1R)-3-oxocyclopentyl)-5-phenyl-1,3-dioxolan-4-one in 1.5 ml of pyridine, 85 mg of hydroxyamine hydrochloride was added at room temperature, followed by stirring for 1 hour at the same temperature. The reaction mixture was diluted with ethyl acetate, washed successively with water and brine, and dried over anhydrous sodium sulfate. Distilling the solvent off gave 55 mg of the title compound.

Step 5. (2R,5R)-2-(t-butyl)-5-((1R)-3,3-difluorocyclopentyl)-5-phenyl-1,3-dioxolan-4-one To a suspension of 20 mg of nitrosonium tetrafluoroborate in 0.5 ml of 70% hydrogen fluoride-pyridine, a solution of 34 mg of (2R,5R)-2-(t-butyl)-5-((1R)-3-hydroxyiminocyclopentyl)-5-phenyl-1,3-dioxolan-4-one in 0.5 ml of dichloromethane was added under cooling with ice, followed by stirring for 10 minutes at 0° C. and for 5 hours at room temperature. Water was added to the reaction mixture under cooling with ice, and extraction was carried out with ethyl acetate. After sequential washing with a saturated aqueous solution of sodium hydrogencarbonate and brine, the organic layer was dried over anhydrous magnesium sulfate. Distilling the solvent off under reduced pressure gave 35 mg of the title compound.

Step 6. Synthesis of (2R)-2-((1R)-3,3-difluorocyclopentyl)-2-hydroxy-2-phenylacetic acid The title compound was prepared by a method similar to Step 3 for Referential Example 1, using (2R,5R)-2-(t-butyl)-5-((1R)-3,3-difluorocyclopentyl)-5-phenyl-1,3-dioxolan-4-one.

REFERENTIAL EXAMPLE 5

(2R)-2-((1R)-3,3-difluorocyclopentyl)-2-hydroxy-2-phenylacetic acid

Step 1. Synthesis of (2R,5R)-2-(t-butyl)-5-(3-trimethylsilyloxy-2-cyclopenten-1-yl)-5-phenyl-1,3-dioxolan-4-one To a solution of 620 mg of (2R,5R)-2-(t-butyl)-5-phenyl-1,3-dioxolan-4-one in 35 ml of tetrahydrofuran, 2.2 ml of 1.5M lithium diisopropylamide solution in hexane was added dropwise at −78° C., followed by stirring for 20 minutes. Then a solution of 295 mg of cyclopentenone in 2 ml of tetrahydrofuran was added, followed by further stirring for 2 hours while the temperature was raised to −60° C. To the reaction mixture, 0.45 ml of trimethylsilyl chloride was added, followed by further stirring for 40 minutes while the temperature was raised to −20° C. The mixture was diluted with ethyl acetate, washed successively with a saturated aqueous solution of ammonium chloride and brine, and dried over anhydrous magnesium sulfate. The solvent was distilled off under reduced pressure to give 1.23 g of the title compound in its crude form.

Step 2. Synthesis of (2R,5S)-2-(t-butyl)-5-(3-oxo-1-cyclopenten-1-yl)-5-phenyl-1,3-dioxolan-4-one To a solution of 800 mg of (2R,5R)-2-(t-butyl)-5-(3-trimethylsilyloxy-2-cyclopenten-1-yl)-5-phenyl-1,3-dioxolan-4-one in 20 ml of acetonitrile, 210 mg of p-quinone and 270 mg of palladium acetate were added successively at room temperature, followed by stirring for 18 hours at the same temperature. The reaction mixture was diluted with diethyl ether, and filtered with Celite. The solvent was distilled off under reduced pressure, and the resulting residue was purified by silica gel column chromatography (eluting solvent: hexane/ethyl acetate=4/1) to give 410 mg of the title compound.

Step 3. Synthesis of (2R,5R)-2-(t-butyl)-5-(3-oxocyclopentyl)-5-phenyl-1,3-dioxolan-4-one To a solution of 18 mg of (2R,5S)-2-(t-butyl)-5-(3-oxo-1-cyclopenten-1-yl)-5-phenyl-1,3-dioxolan-4-one in 2 ml of ethyl acetate, 5 mg of 10% palladium-carbon catalyst was added, followed by stirring for 24 hours in a hydrogen atmosphere. After the catalyst was filtered off, 20 mg of the title compound was obtained by distilling the solvent off under reduced pressure.

Step 4. Synthesis of (2R)-2-((1R)-3,3-difluorocyclopentyl)-2-hydroxy-2-phenylacetic acid The title compound was prepared by a method similar to that for Referential Example 1, using (2R,5R)-2-(t-butyl)-5-(3-oxocyclopentyl)-5-phenyl-1,3-dioxolan-4-one.

REFERENTIAL EXAMPLE 6

(2R)-2-(3,3-difluorocyclobutyl)-2-hydroxy-2-phenylacetic acid

Step 1. Synthesis of (2R,5R)-2-(t-butyl)-5-(3-benzyloxy-1-hydroxycyclobutyl)-5-phenyl-1,3-dioxolan-4-one The title compound was prepared by a method similar to that of Step 1 for Referential Example 1, using 3-benzyloxycyclobutanone.

Step 2. Synthesis of (2R,5R)-2-(t-butyl)-5-(3-benzyloxycyclobutyl)-5-phenyl-1,3-dioxolan-4-one To a solution of 2.82 g of (2R,5R)-2-(t-butyl)-5-(3-benzyloxy-1-hydroxycyclobutyl)-5-phenyl-1,3-dioxolan-4-one, obtained by Step 1, in 80 ml of chloroform, 2.6 g of 4-dimethylaminopyridine was added under cooling with ice, followed by stirring for 1 hour at the same temperature. To the reaction mixture, 1 ml of methyl chloroglyoxylate was added, followed by further stirring for 1 hour. The reaction mixture was diluted with chloroform, washed successively with water and brine, and dried over anhydrous magnesium sulfate. The solvent was distilled off under reduced pressure, and a mixture of the resulting residue and hexane/ethyl acetate=1/1 was filtered with a silica gel column. The solvent of the filtrate was distilled off under reduced pressure, and 56 mg of 2,2'-azobis(isobutyronitrile) and 2.3 ml of tri-n-butyl tin hydride were added to a solution of the resulting residue in 80 ml of toluene at room temperature, followed by stirring for 4 hours under heating at 110° C. The solvent was distilled off under reduced pressure, and 1.82 g of the title compound was obtained as an oily substance by purifying the resulting residue by silica gel column chromatography (eluting solvent: hexane/ethyl acetate=8/1).

Step 3. Synthesis of (2R,5R)-2-(t-butyl)-5-(3-oxocyclobutyl)-5-phenyl-1,3-dioxolan-4-one To a solution of 1.82 g of (2R,5R)-2-(t-butyl)-5-(3-benzyloxycyclobutyl)-5-phenyl-1,3-dioxolan-4-one, obtained by Step 2, in 40 ml of ethanol, 430 mg of palladium hydroxide-carbon catalyst was added, followed by stirring for 6 hours at ambient temperature under a hydrogen atmosphere. The reaction mixture was filtered with Celite, the solvent was distilled off under reduced pressure, and a solution of the resulting residue in 5 ml of dichloromethane was added dropwise at −78° C. to a reaction mixture resulting from the addition of 0.63 ml of oxalyl chloride to a solution of 1.1 ml of dimethylsulfoxide in 50 ml of dichloromethane at −78° C. and stirring for 5 minutes, followed by stirring for 15 minutes at the same temperature. To the reaction mixture, 0.5 ml of triethyl amine was further added, followed by stirring for 30 minutes with warming to room temperature. The reaction mixture was diluted with chloroform, washed successively with water and brine, and dried over anhydrous magnesium sulfate. The solvent was distilled off, and 1.36 g of the title compound was obtained as an oily substance by refining the resulting residue by silica gel column chromatography (eluting solvent: hexane/ethyl acetate=8/1).

Step 4. Synthesis of (2R)-2-(3,3-difluorocyclobutyl)-2-hydroxy-2-phenylacetic acid The title compound was prepared by a method similar to that for Referential Example 1, using (2R,5R)-2-(t-butyl)-5-(3-oxocyclobutyl)-5-phenyl- 1,3-dioxolan-4-one, obtained by Step 3.

REFERENTIAL EXAMPLE 7

(2R)-2-(4,4-difluorocyclohexyl)-2-hydroxy-2-phenylacetic acid

Step 1. Synthesis of (2R,5R)-2-(t-butyl)-5-(1,4-dioxaspiro[4.5]dec-8-yl)-5-phenyl-1,3-dioxolan-4-one The title compound was prepared by a method similar to those of Steps 1 and 2 for Referential Example 6, using 8-oxo-1,4-dioxaspiro[4.5]decane.

Step 2. Synthesis of (2R,5R)-2-(t-butyl)-5-(4-oxocyclohexyl)-5-phenyl-1,3-dioxolan-4-one To a solution of 83 mg of (2R,5R)-2-(t-butyl)-5-(1,4-dioxaspiro[4.5]dec-8-yl)-5-phenyl-1,3-dioxolan-4-one, obtained by Step 1, in a mixture of 4 ml of acetone and 0.4 ml of water, 52 mg of p-toluenesulfonic acid was added at room temperature, followed by stirring for 13 hours at 50° C. Acetone was distilled off under reduced pressure, and the reaction mixture was diluted with ethyl acetate, washed successively with a saturated aqueous solution of sodium hydrogencarbonate and brine, and dried over anhydrous magnesium sulfate. The solvent was distilled off under reduced pressure, and 70 mg of the title compound was obtained as an oily substance.

Step 3. Synthesis of (2R)-2-(4,4-difluorocyclohexyl)-2-hydroxyphenylacetic acid

The title compound was prepared by a method similar to that for Referential Example 1, using (2R,5R)-2-(t-butyl)-5-(4-oxocyclohexyl)-5-phenyl-1,3-dioxolan-4-one, obtained by Step 2.

Example of Pharmaceutical Composition 1

|  | No. of mg per tablet |
|---|---|
| Compound of Example 1 | 5.0 |
| Lactose | 103.8 |
| Crystalline cellulose | 20.0 |
| Partially alpha starch | 20.0 |
| Magnesium stearate | 1.2 |
| Total | 150.0 mg |

After mixing 20.0 g of the compound of Example 1, 415.2 g of lactose, 80 g of crystalline cellulose and 80 g of partially alpha starch with a V-type mixer, 4.8 g of magnesium stearate was further added to the mixture, followed by further mixing. The mixed powder was tableted by a conventional method, resulting in an output of 3,000 tablets each measuring 7.0 mm in diameter and weighing 150 mg.

Example of Pharmaceutical Composition 2

|  | No. of mg per tablet |
| --- | --- |
| Tablets of Composition 1 | 150 |
| Hydroxypropylcellulose 2910 | 3.6 |
| Polyethylene glycol 6000 | 0.7 |
| Titanium dioxide | 0.7 |
| Total | 155 mg |

After 10.8 g of hydroxypropylcellulose 2910 and 2.1 g of polyethylene glycol 6000 were dissolved in 172.5 g of purified water, 2.1 g of titanium dioxide was dispersed in the solution to prepare a coating liquid. Separately prepared 3,000 tablets of Composition 1 were coated with this coating liquid using a High Coater Mini, and film-coated tablets weighing 155 mg each were obtained.

Example of Pharmaceutical Composition 3

In 900 ml of physiological saline, 0.1 g of the compound of Example 1 was dissolved, and in addition physiological saline was added to make the total quantity of the solution 1,000 ml, followed by sterile filtration with a membrane filter of 0.25 μm in pore diameter. This solution was poured into sterilized ampules, at a rate of 1 ml per ampule, to be supplied as inhalant.

Example of Pharmaceutical Composition 4

Ten g of the compound of Example 1 and 70 g of lactose were mixed uniformly, and powder inhalers specially designed for the purpose were filled with the mixed powder at a rate of 100 mg per inhaler, to be supplied as powder inhaler (400 μg to be inhaled at a time).

Industrial Applicability

Compounds of the present invention, since they not only have potent selective antagonistic activity against muscarinic $M_3$ receptors but also exhibit excellent oral activity, durability of action and pharmacokinetics, are very useful as safe and effective remedies against respiratory, urinary and digestive diseases with little adverse side effects.

What is claimed is:

1. A compound represented by the formula (I):

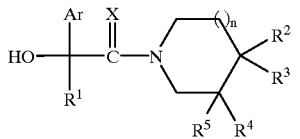

or a pharmaceutically acceptable salt thereof,
wherein
Ar represents an unsubstituted aryl group, an unsubstituted heteroaryl group, a substituted aryl group or a substituted heteroaryl group, wherein the substituent for the aryl group and heteroaryl group is selected from the group consisting of a halogen atom, a lower alkyl group, and a lower alkoxy group;
$R^1$ represents an unsubstituted $C_3$–$C_6$ cycloalkyl group or a fluorine atom substituted $C_3$–$C_6$ cycloalkyl group;
$R^2$ represents a hydrogen atom or a group having the formula —$(A^1)_m$—NH—B or,
$R^2$ combined with $R^3$, is
(i) a group represented by the formula =$A^2$—NH—B, or
(ii) together with the adjoining one of the carbon atoms on the ring, represents a $C_2$–$C_8$ aliphatic nitrogen-containing heterocyclic group containing an imino group, and wherein said nitrogen-containing heterocyclic group is unsubstituted or substituted with a lower alkyl group, or
(iii) together with the adjoining one of the carbon atoms on the ring, represents a $C_3$–$C_8$ aliphatic carbocyclic group having on the ring a group —$(A^1)_m$—NH—B, or having on the ring both said group —$(A^1)_m$—NH—B and a lower alkyl group, or
$R^2$ combined with $R^4$, and the adjoining two carbon atoms to which $R^2$ and $R^4$ are bonded, represents a $C_2$–$C_8$ aliphatic nitrogen-containing heterocyclic group containing an imino group, and wherein said nitrogen-containing heterocyclic group is unsubstituted or substituted with a lower alkyl group;
$R^3$ represents a hydrogen atom, an unsubstituted $C_1$–$C_8$ aliphatic hydrocarbon group or a lower alkyl-substituted $C_1$–$C_8$ aliphatic hydrocarbon group or,
$R^3$ combined with $R^5$ represents a single bond or,
$R^3$ together with an adjoining one of the carbon atoms on the ring, represents
(i) a $C_2$–$C_8$ aliphatic nitrogen-containing heterocyclic group containing an imino group, and wherein said nitrogen-containing heterocyclic group is unsubstituted or substituted with a lower alkyl group, or
(ii) a $C_3$–$C_8$ aliphatic carbocyclic group having on the ring a group —$(A^1)_m$—NH—B, or having on the ring both said group —$(A^1)_m$—NH—B and a lower alkyl group;
$R^4$ represents a hydrogen atom or a group having the formula —$(A^1)_m$—NH—B, or,
$R^4$ combined with $R^5$ is a group represented by the formula =$A^2$—NH—B, or,
$R^4$ together with an adjoining one of the carbon atoms on the ring, represents
(i) a $C_2$–$C_8$ aliphatic nitrogen-containing heterocyclic group containing an imino group, and wherein said nitrogen-containing heterocyclic group is unsubstituted or substituted with a lower alkyl group or,
(ii) a $C_3$–$C_8$ carbocyclic group having on the ring a group —$(A^1)_m$—NH—B, or having on the ring both said group —$(A^1)_m$—NH—B and a lower alkyl group;
$R^5$ represents a hydrogen atom or an unsubstituted $C_1$–$C_6$ aliphatic hydrocarbon group or a lower alkyl group-substituted $C_1$–$C_6$ aliphatic hydrocarbon group, or
$R^5$ together with an adjoining one of the carbon atoms on the ring, represents
(i) a $C_2$–$C_8$ aliphatic nitrogen-containing heterocyclic group containing an imino group, and wherein said nitrogen-containing heterocyclic group is unsubstituted or substituted with a lower alkyl group, or,
(ii) a $C_3$–$C_8$ aliphatic carbocyclic group having on the ring a group —$(A^1)_m$—NH—B, or having on the ring both said group —$(A^1)_m$—NH—B and a lower alkyl group;
$A^1$ represents an unsubstituted $C_1$–$C_8$ bivalent aliphatic hydrocarbon group or a lower alkyl group-substituted $C_1$–$C_8$ bivalent aliphatic hydrocarbon group;

$A^2$ represents an unsubstituted $C_1$–$C_8$ trivalent aliphatic hydrocarbon group or a lower alkyl group-substituted $C_1$–$C_8$ trivalent aliphatic hydrocarbon group;

B represents a hydrogen atom, an unsubstituted $C_1$–$C_6$ aliphatic hydrocarbon group or a substituted $C_1$–$C_6$ aliphatic hydrocarbon group, wherein said substituent is a lower alkyl group or aryl group;

m represents 0 or 1;

n represents 0 or 1; and

X represents an oxygen atom or a sulfur atom, with the provisos that:
(a) $R^2$ and $R^4$ do not simultaneously represent a hydrogen atom;
(b) when either $R^2$ or $R^4$ represents the group —$(A^1)_m$—NH—B, the other represents a hydrogen atom;
(c) when $R^2$ and $R^3$ combine to form said group =$A^2$—NH—B or together with the carbon atom to which they are bonded combine to form said $C_2$–$C_8$ aliphatic nitrogen-containing heterocyclic group or said $C_3$–$C_8$ aliphatic carbocyclic group, $R^4$ represents a hydrogen atom; and
(d) when $R^4$ and $R^5$ combine to form said group =$A^2$—NH—B or together with the carbon atom to which they are bonded combine to form said $C_2$–$C_8$ aliphatic nitrogen-containing heterocyclic group or said $C_3$–$C_8$ aliphatic carbocyclic group, $R^2$ represents a hydrogen atom.

2. Compounds according to claim 1, in which Ar is a phenyl group.

3. Compounds according to claim 1, in which $R^1$ is a $C_3$–$C_6$ cycloalkyl group having a fluorine atom(s) in any substitutable position.

4. Compounds according to claim 1, in which the $C_3$–$C_6$ cycloalkyl group of $R^1$ is a cyclopentyl group.

5. Compounds according to claim 1, in which $R^1$ is a 3,3-difluorocyclopentyl group.

6. Compounds according to claim 1, in which either $R^2$ or $R^4$ is a group represented by —$(A^1)_m$—NH—B.

7. Compounds according to claim 6, in which m is 1 and $A^1$ is an ethylene group substitutable with a lower alkyl group.

8. Compounds according to claim 6, in which B is a hydrogen atom.

9. Compounds according to claim 1, in which $R^2$ and $R^3$ combined, together with the adjoining one of the carbon atoms on the ring, means a $C_2$–$C_8$ aliphatic nitrogen-containing heterocyclic group containing an imino group, which is substitutable with a lower alkyl group.

10. Compounds according to claim 9, in which the $C_2$–$C_8$ aliphatic nitrogen-containing heterocyclic group containing an imino group consists of a pyrrolidine ring.

11. Compounds according to claim 1, in which $R^2$ and $R^4$ combined, together with the adjoining two of the carbon atoms on the ring, means a $C_2$–$C_8$ aliphatic nitrogen-containing heterocyclic group containing an imino group, which is substitutable with a lower alkyl group.

12. Compounds according to claim 11, in which the $C_2$–$C_8$ aliphatic nitrogen-containing heterocyclic group containing an imino group consists of a perhydroazepine ring.

13. Compounds according to claim 1, in which X is an oxygen atom.

14. Compounds according to claim 1, including:

4-amino-1-{(2R)-2-((1R)-3,3-difluorocyclopentyl)-2-hydroxy-2-phenylacetyl}piperidine, 4-amino-1-{(2R)-2-cyclopentyl)-2-hydroxy-2-phenylacetyl}piperidine, 4-amino-1-{(2R)-2-((1R)-3,3-difluorocyclopentyl)-2-hydroxy-2-phenylacetyl}-4-methylpiperidine, 4-amino-1-{(2R)-2-cyclopentyl)-2-hydroxy-2-phenylacetyl}-4-methylpiperidine, 4-amino-1-{(2R)-2-((1R)-3,3-difluorocyclopentyl)-2-hydroxy-2-phenylacetyl}-4-ethylpiperidine, 4-amino-1-((2R)-2-cyclopentyl)-2-hydroxy-2-phenylacetyl)-4-ethylpiperidine, 4-aminomethyl-1-{(2R)-2-((1R)-3,3-difluorocyclopentyl)-2-hydroxy-2-phenylacetyl}piperidine, 4-aminomethyl-1-((2R)-2-cyclopentyl)-2-hydroxy-2-phenylacetyl)piperidine, 4-aminomethyl-1-{(2R)-2-((1R)-3,3-difluorocyclopentyl)-2-hydroxy-2-phenylacetyl}-4-methylpiperidine, 4-aminomethyl-1-{(2R)-2-((1R)-3,3-difluorocyclopentyl)-2-hydroxy-2-phenylacetyl}-4-ethylpiperidine, 4-(1-aminoethyl)-1-{(2R)-2-((1R)-3,3-difluorocyclopentyl)-2-hydroxy-2-phenylacetyl}piperidine, 4-(1-aminoethyl)-1-((2R)-2-cyclopentyl)-2-hydroxy-2-phenylacetyl)piperidine 4-(2-aminoethyl)-1-{(2R)-2-((1R)-3,3-difluorocyclopentyl)-2-hydroxy-2-phenylacetyl}piperidine, 4-(2-aminoethyl)-1-((2R)-2-cyclopentyl)-2-hydroxy-2-phenylacetyl)piperidine, 4-(2-aminoethyl)-1-{(2R)-2-((1R)-3,3-difluorocyclopentyl)-2-hydroxy-2-phenylacetyl}-4-methylpiperidine, 4-(2-amino-1-methylethyl)-1-{(2R)-2-((1R)-3,3-difluorocyclopentyl)-2-hydroxy-2-phenylacetyl}piperidine, 4-(2-amino-1-methylethyl)-1-((2R)-2-cyclopentyl)-2-hydroxy-2-phenylacetyl)piperidine, 4-(1-aminomethylpropyl)-1-{(2R)-2-((1R)-3,3-difluorocyclopentyl)-2-hydroxy-2-phenylacetyl}piperidine, 4-(2-aminopropyl)-1-{(2R)-2-((1R)-3,3-difluorocyclopentyl)-2-hydroxy-2-phenylacetyl}piperidine, 4-(2-aminopropyl)-1-((2R)-2-cyclopentyl)-2-hydroxy-2-phenylacetyl)piperidine, 4-(2-aminobutyl)-1-{(2R)-2-((1R)-3,3-difluorocyclopentyl)-2-hydroxy-2-phenylacetyl}piperidine, 4-(2-aminopentyl)-1-{(2R)-2-((1R)-3,3-difluorocyclopentyl)-2-hydroxy-2-phenylacetyl}piperidine, 4-(2-amino-2-methylpropyl) -1-{(2R)-2-((1R)-3,3-difluorocyclopentyl)-2-hydroxy-2-phenylacetyl}piperidine, 4-(2-aminoethylidene)-1-{(2R)-2-((1 R)-3,3-difluorocyclopentyl)-2-hydroxy-2-phenylacetyl}piperidine, 4-(2-aminoethyl)-1-{(2R)-2-((1R)-3,3-difluorocyclopentyl)-2-hydroxy-2-phenylacetyl}-1,2,3,6-tetrahydropyridine, 8-{(2R)-2-((1R)-3,3-difluorocyclopentyl)-2-hydroxy-2-phenylacetyl}-2,8-diazaspiro[4.5]decane, 1-aminomethyl-6-{(2R)-2-((1R)-3,3-difluorocyclopentyl)-2-hydroxy-2-phenylacetyl}-6-azaspiro[2.5]octane, 2-{(2R)-2-((1R)-3,3-difluorocyclopentyl)-2-hydroxy-2-phenylacetyl}-2,8-diazaspiro[4.5]decane, 9-{(2R)-2-((1R)-3,3-difluorocyclopentyl)-2-hydroxy-2-phenylacetyl}-cis-4,9-diazabicyclo[5.3.01]decane, 3-{(2R)-2-((1R)-3,3-difluorocyclopentyl)-2-hydroxy-2-phenylacetyl}-3,7-diazabicyclo[3.3.0]octane, 7-{(2R)-2-((1R)-3,3-difluorocyclopentyl)-2-hydroxy-2-phenylacetyl}-2,7-diazaspiro[4.5]decane, 3-1{(2R)-2-((1R)-3,3-difluorocyclopentyl)-2-hydroxy-2-phenylacetyl}-3,9-diazaspiro[5.5]undecane, 9-{(2R)-2-((1R)-3,3-difluorocyclopentyl)-2-hydroxy-2-phenylacetyl}-2,9-diazaspiro[5.5]undecane, 2-{(2R)-2-((1R)-3,3-difluorocyclopentyl)-2-hydroxy-2-phenylacetyl}-2,7-diazaspiro[4.4]nonane, 3-{(2R)-2-((1R)-3,3-difluorocyclopentyl)-2-hydroxy-2-phenylacetyl}-3,7-diazabicyclo[3.3.0]oct-1(5)-ene, 2-{(2R)-2-((1R)-3,3-difluorocyclopentyl)-2-hydroxy-2-phenylacetyl}-4-methyl-2,8-diazaspiro[4.5]decane, 8-{(2R)-2-((1R)-3,3-difluorocyclopentyl)-2-hydroxy-2-phenylacetyl}-3-methyl-2,8-diazaspiro[4.5]decane, 8-{(2R)-2-((1R)-3,3-difluorocyclopentyl)-2-hydroxy-2-phenylacetyl}-4-methyl-2,8-diazaspiro[4.5]decane, 7-{(2R)-2-((1R)-3,3-difluorocyclopentyl)-2-hydroxy-2-phenylacetyl}-2,7-diazaspiro[3.5]nonane, 3-{(2R)-2-((1R)-3,3-difluorocyclopentyl)-2-hydroxy-2-phenylacetyl}-3,8-diazabicyclo[4.3.0]nonane, 8-{(2R)-2-((1R)-3,3-difluorocyclopentyl)-2-hydroxy-2-phenylacetyl}-3,8-diazabicyclo[4.3.0]nonane, 9-{(2R)-2-((1R)-3,3-difluorocyclopentyl)-2-hydroxy-2-phenylacetyl}-3,9-diazabicyclo[5.3.0]decane, 8-{(2R)-2-((1R)-3,3-difluorocyclopentyl)-2-hydroxy-2-phenylacetyl}-1-methyl-2,8-diazaspiro[4.5]decane, 2-{(2R)-2-((1R)-3,3-difluorocyclopentyl)-2-hydroxy-2-phenylacetyl}-2,7-diazaspiro[4.5]decane, 9-{(2R)-2-((1R)-3,3-difluorocyclopentyl)-2-hydroxy-2-phenylacetyl}-4,9-diazabicyclo[5.3.0]decane, 8-{(2R)-2-((1R)-3,3-difluorocyclopentyl)-2-hydroxy-2-phenylacetyl}-1-ethyl-2,8-diazaspiro[4.5]decane, 9-{(2R)-2-((1R)-3,3-difluorocyclopentyl)-2-hydroxy-2-phenylacetyl}-3-methyl-cis-4,9-diazabicyclo[5.3.0]decane, 4-aminomethyl-1-{(2R)-2-((1R)-3,3-difluorocyclopentyl)-2-hydroxy-2-phenylacetyl}-1,2,3,6-tetrahydropyridine, and 2-{(2R)-2-((1R)-3,3-difluorocyclopentyl)-2-hydroxy-2-phenylacetyl}-2,7-diazaspiro[4.5]decane.

15. Compounds according to claim 1, including 4-amino-1-{(2R)-2-((1R)-3,3-difluorocyclopentyl)-2-hydroxy-2-phenylacetyl}piperidine.

16. Compounds according to claim 1, including 4-(2-aminoethyl)-1-{(2R)-2-((1R)-3,3-difluorocyclopentyl)-2-hydroxy-2-phenylacetyl}piperidine.

17. Compounds according to claim 1, including 8-{(2R)-2-((1R)-3,3-difluorocyclopentyl)-2-hydroxy-2-phenylacetyl}-2,8-diazaspiro[4.5]decane.

18. Compounds according to claim 1, including 9-{(2R)-2-((1R)-3,3-difluorocyclopentyl)-2-hydroxy-2-phenylacetyl}-cis-4,9-diazabicyclo[5.3.0]decane.

19. Compounds according to claim 1, including 3-{(2R)-2-((1R)-3,3-difluorocyclopentyl)-2-hydroxy-2-phenylacetyl}-3,7-diazabicyclo[3.3.0]oct-1(5)-ene.

20. Compounds according to claim 1, including 8-{(2R)-2-((1R)-3,3-difluorocyclopentyl)-2-hydroxy-2-phenylacetyl}-1-methyl-2,8-diazaspiro[4.5]decane.

21. A process for preparation of a compound represented by the formula (I) as set forth in claim 1, which comprises:

reacting a compound of represented by formula (III)

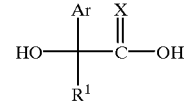

(III)

or a reactive derivative thereof, wherein Ar, X and $R^1$, have the same meanings as defined above, with a compound represented by the formula (IV)

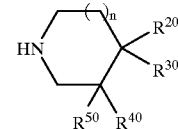

$R^{20}$ represents a hydrogen atom or a group having the formula $—(A^1)_m—NH—B^p$ or, $R^{20}$ combined with $R^{30}$, is
(i) a group represented by the formula $=A^2—N(P^1)—B^P$, or
(ii) together with the adjoining one of the carbon atoms on the ring, represents a $C_2–C_8$ aliphatic nitrogen-containing heterocyclic group containing an imino group, and wherein said nitrogen-containing heterocyclic group is unsubstituted or substituted with a lower alkyl group, or
(iii) together with the adjoining one of the carbon atoms on the ring, represents a $C_3–C_8$ aliphatic carbocyclic group having on the ring a group $—(A^1)_m—N(P^1)—B^P$, or having on the ring both said group $—(A^1)_m—N(P^1)—B^P$ and a lower alkyl group, or $R^{20}$ combined with $R^{40}$, and the adjoining two carbon atoms to which $R^{20}$ and $R^{40}$ are bonded, represents a $C_2–C_8$ aliphatic nitrogen-containing heterocyclic group containing an imino group, and wherein said nitrogen-containing heterocyclic group is unsubstituted or substituted with a lower alkyl group;

$R^{30}$ represents a hydrogen atom, an unsubstituted $C_1–C_8$ aliphatic hydrocarbon group or a lower alkyl-substituted $C_1–C_8$ aliphatic hydrocarbon group or, $R^{30}$ combined with $R^{50}$ represents a single bond or, $R^{30}$ together with an adjoining one of the carbon atoms on the ring, represents
(i) a $C_2–C_8$ aliphatic nitrogen-containing heterocyclic group containing an imino group, and wherein said nitrogen-containing heterocyclic group is unsubstituted or substituted with a lower alkyl group, or
(ii) a $C_3–C_8$ aliphatic carbocyclic group having on the ring a group $—(A^1)_m—N(P^1)—B^P$, or having on the ring both said group $—(A^1)_m—N(P^1)—B^P$ and a lower alkyl group;

$R^{40}$ represents a hydrogen atom or a group having the formula $—(A^1)_m—N(P^1)—B^P$, or, $R^{40}$ combined with $R^{50}$ is a group represented by the formula $=A^2—N(P^1)—B^P$, or, $R^{40}$ together with an adjoining one of the carbon atoms on the ring, represents
  (i) a $C_2$–$C_8$ aliphatic nitrogen-containing heterocyclic group containing an imino group, and wherein said nitrogen-containing heterocyclic group is unsubstituted or substituted with a lower alkyl group or,
  (ii) a $C_3$–$C_8$ carbocyclic group having on the ring a group —$(A^1)_m$—$N(P^1)$—$B^p$, or having on the ring both said group —$(A^1)_m$—$N(P^1)$—$B^p$ and a lower alkyl group;
$R^{50}$ represents a hydrogen atom or an unsubstituted $C_1$–$C_6$ aliphatic hydrocarbon group or a lower alkyl group-substituted $C_1$–$C_6$ aliphatic hydrocarbon group, or
$R^{50}$ together with an adjoining one of the carbon atoms on the ring, represents
  (i) a $C_2$–$C_8$ aliphatic nitrogen-containing heterocyclic group containing an imino group, and wherein said nitrogen-containing heterocyclic group is unsubstituted or substituted with a lower alkyl group, or,
  (ii) a $C_3$–$C_8$ aliphatic carbocyclic group having on the ring a group —$(A^1)_m$—$N(P^1)$—$B^p$, or having on the ring both said group —$(A^1)_m$—$N(P^1)$—$B^p$ and a lower alkyl group;
$A^1$, $A^2$, X, m and n have the same meanings as above;
$B^p$ represents a hydrogen atom, an unsubstituted $C_1$–$C_6$ aliphatic hydrocarbon group or a substituted $C_1$–$C_6$ aliphatic hydrocarbon group, wherein said substituent is a lower alkyl group or aryl group; or $B^p$ combined with $P^1$ represents a protective group for an amino group; and
$P^1$ represents a hydrogen atom or a protective group for an amino group or for an imino group;
with the provisos that:
  (a) $R^{20}$ and $R^{40}$ do not simultaneously represent a hydrogen atom;
  (b) when either $R^{20}$ or $R^{40}$ represents the group —$(A^1)_m$—NH—B, the other represents a hydrogen atom;
  (c) when $R^{20}$ and $R^{30}$ combine to form said group =$A^2$—NH—$B^p$ or together with the carbon atom to which they are bonded combine to form said $C_2$–$C_8$ aliphatic nitrogen-containing heterocyclic group or said $C_3$–$C_8$ aliphatic carbocyclic group, $R^{40}$ represents a hydrogen atom; and
  (d) when $R^{40}$ and $R^{50}$ combine to form said group =$A^2$—NH—$B^p$ or together with the carbon atom to which they are bonded combine to form said $C_2$–$C_8$ aliphatic nitrogen-containing heterocyclic group or said $C_3$–$C_8$ aliphatic carbocyclic group, $R^{20}$ represents a hydrogen atom,
or a salt thereof, to remove a protective group from an amino or imino group; and, is as required, (a) reductive amination with aldehyde or ketone represented by formula (V)

$$O=B^{10},$$

where $B^{10}$ represents a $C_1$–$C_6$ aliphatic hydrocarbon group, which is unsubstituted or substituted by lower alkyl group or aryl group, or removal of any protective group for amino or imino group involved in the reaction while protecting a hydroxyl or oxo group not involved in the reaction, carrying out a reaction, in the presence of a base, with a compound represented by the formula (V') in the presence of a base, $$L\text{—}B \qquad (V')$$

where L represents a leaving group, and B is defined above; and removing, as required, any protective group (s) for amino, imino, hydroxyl or oxo groups.

22. A pharmaceutical composition, effective for treatment or prevention of diseases associated with muscarinic $M^3$ receptors, comprising a compound of formula (I) as set forth in claim 1, or pharmaceutically acceptable salt thereof, exhibiting selective antagonistic activity against muscarinic $M^3$ receptors, and pharmaceutically acceptable adjuvant.

23. The pharmaceutical composition according to claim 22, wherein the compound of formula (I) or the pharmaceutically acceptable salt thereof is present in an amount of from 1.0 to 60 percent by weight of the composition.

24. A method for treatment or prophylaxis of respiratory diseases, urinary disorders, or gastrointestinal system diseases, wherein the disease or disorder is associated with muscarinic $M_3$ receptors, comprising administering to a patient in need thereof, an antagonistic effective amount, selective for muscarinic M3 receptor, of a compound of formula (I) as set forth in claim 1 or a pharmaceutically acceptable salt thereof.

25. The method according to claim 24, wherein the disease or disorder is chronic bronchitis, asthma, chronic respiratory obstruction, pulmonary fibrosis, pulmonary emphysema, rhinitis, irritable bowel syndrome, convulsive colitis, gastric ulcer, duodenal ulcer, convulsion or hyperkinesia of digestive canal, diverticulitis, pain accompanying contraction of smooth muscles of the digestive system, urinary incontinence, urinary urgency, pollakiuria, nervous pollakiuria, neurogenic bladder, nocturnal enuresis, unstable bladder, cystospasm, chronic cystisis, or motion sickness.

26. The method according to claim 24 which comprises orally administering said compound of formula (I) in an amount of from about 0.1 to 100 mg/kg body weight/day.

27. The method according to claim 24 which comprises parenterally administering said compound of formula (I) in an amount of from about 0.001 to 10 mg/kg body weight/day.

* * * * *